United States Patent
Prat et al.

(10) Patent No.: US 10,428,144 B2
(45) Date of Patent: Oct. 1, 2019

(54) DICAM-SPECIFIC ANTIBODIES AND USES THEREOF

(71) Applicant: Centre Hospitalier de L'Université de Montréal, Montréal, Québec (CA)

(72) Inventors: Alexandre Prat, Outremont (CA); Soufiane Ghannam, Montréal (CA)

(73) Assignee: VAL-CHUM, LIMITED PARTNERSHIP, Montreal (CA)

(*) Notice: Subject to any disclaimer, the term of this patent is extended or adjusted under 35 U.S.C. 154(b) by 40 days.

(21) Appl. No.: 15/537,768

(22) PCT Filed: Dec. 17, 2015

(86) PCT No.: PCT/CA2015/051338
§ 371 (c)(1),
(2) Date: Jun. 19, 2017

(87) PCT Pub. No.: WO2016/095046
PCT Pub. Date: Jun. 23, 2016

(65) Prior Publication Data
US 2018/0057590 A1    Mar. 1, 2018

Related U.S. Application Data

(60) Provisional application No. 62/094,590, filed on Dec. 19, 2014, provisional application No. 62/235,781, filed on Oct. 1, 2015.

(51) Int. Cl.
| | |
|---|---|
| *A61K 39/395* | (2006.01) |
| *C07K 16/00* | (2006.01) |
| *C07K 16/28* | (2006.01) |
| *A61P 25/00* | (2006.01) |
| *A61P 37/00* | (2006.01) |
| *A61K 39/00* | (2006.01) |

(52) U.S. Cl.
CPC .......... *C07K 16/2803* (2013.01); *A61P 25/00* (2018.01); *A61P 37/00* (2018.01); *A61K 2039/505* (2013.01); *C07K 2317/24* (2013.01); *C07K 2317/34* (2013.01); *C07K 2317/56* (2013.01); *C07K 2317/565* (2013.01); *C07K 2317/70* (2013.01); *C07K 2317/76* (2013.01)

(58) Field of Classification Search
None
See application file for complete search history.

(56) References Cited

FOREIGN PATENT DOCUMENTS

| KR | 20090124439 | 12/2009 | | |
|---|---|---|---|---|
| WO | WO-2010046443 A2 | * | 4/2010 | ......... G01N 33/6887 |

OTHER PUBLICATIONS

Acharya et al. "alphaV Integrin expression by DCs is required for Th17 cell differentiation and development of experimental autoimmune encephalomyelitis in mice", The Journal of Clinical Investigation 120(12):4445-4452 (2010).
Du et al. "Inflammatory Th17 Cells Express Integrin alphavbeta3 for Pathogenic Function". Cell Rep. 16(5):1339-1351 (2016).
Han et al. "DICAM inhibits angiogenesis via suppression cf AKT and p38 MAP kinase signalling", Cardiovascular Research 98: 73-82 (2013).
Murphy et al. "Infiltration of Th1 and Th17 cells and activation of microglia in the CNS during the course of experimental autoimmune encephalomyelitis", Brain, Behavior, and Immunity 24:641-651 (2010).
Sonobe et al. "ChronolocLcal Changes of CD4+ and CD8+ T Cell Subsets in the Experimental Autoimmune Encephalomyelitis, a Mouse Model of Multiple Sclerosis", Tohoku J. Exp. Med. 213:329-339 (2007).
Extended European Search Report corresponding to European Application No. 15868768.9 dated Jun. 26, 2018.
Yonezawa et al., Limitrin, a Novel Immunoglobulin Superfamily Protein Localized to Glia Lirnitans Formed by Astrocyte Endfeet, Glia, II Aug. 2003 (Nov. 8, 2003) online, vol. 44, No. 3,pp. 190-204.
Jung et al., DICAM, a Novel Dual Immunoglobulin Domain Containing Cell Adhesion Molecule Interacts With avb3Integrin, Journal of Cellular Physiology, Mar. 25, 2008 (Mar. 25, 2008) online, vol. 216, No. 3, pp. 603-614.
Jung et al., DICAM Inhibits Ostoeclast Differentation Through Attentuation of the Integrin aVb3 Pathway, Journal of Bone and Mineral Research, vol. 27, No. 9, Sep. 2012, pp. 2024-2034.
Notification of Transmittal of the International Search Report and the Written Opinion of the International Searching Authority, or the Declaration corresponding to International Application No. PCT/CA2015/051338 dated Feb. 10, 2016.

* cited by examiner

*Primary Examiner* — Maher M Haddad
(74) *Attorney, Agent, or Firm* — Myers Bigel, P.A.

(57) ABSTRACT

Novel antibodies directed against Dual Ig domain containing cell adhesion molecule (DICAM) are described. These anti-DICAM antibodies are capable of detecting DICAM by Western blot and/or flow cytometry, blocking the interaction between DICAM and its ligand αVβ3 integrin, and/or blocking the migration of inflammatory cytokine-secreting $T_H17$ lymphocytes across the blood brain barrier. Uses of these antibodies or compositions comprising same for the diagnosis, prevention and/or treatment of autoimmune/inflammatory conditions, such as neuroinflammatory conditions, and for the targeting, identification and selection of inflammatory cytokine-secreting $T_H17$ lymphocytes or precursor thereof are also disclosed.

17 Claims, 33 Drawing Sheets
Specification includes a Sequence Listing.

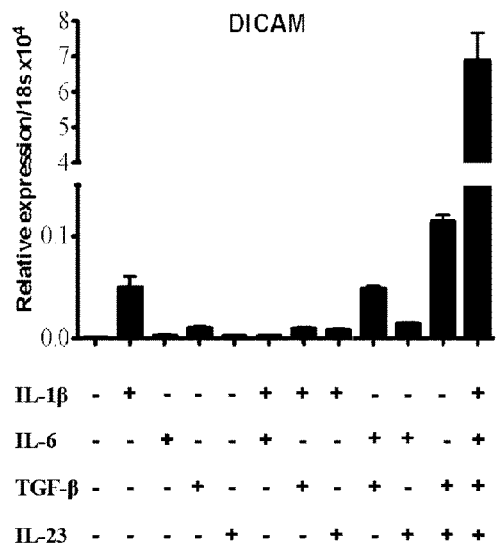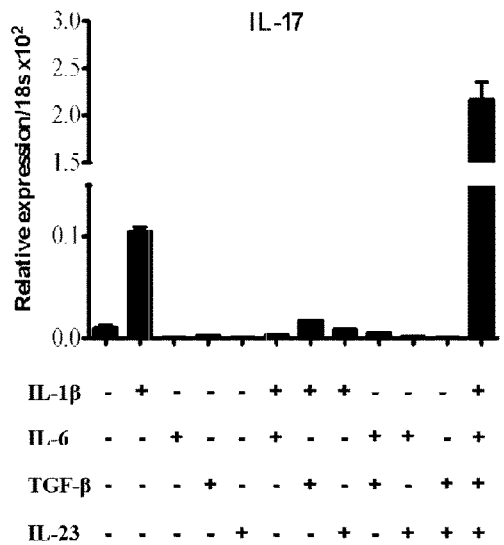
FIG. 6A  FIG. 6B
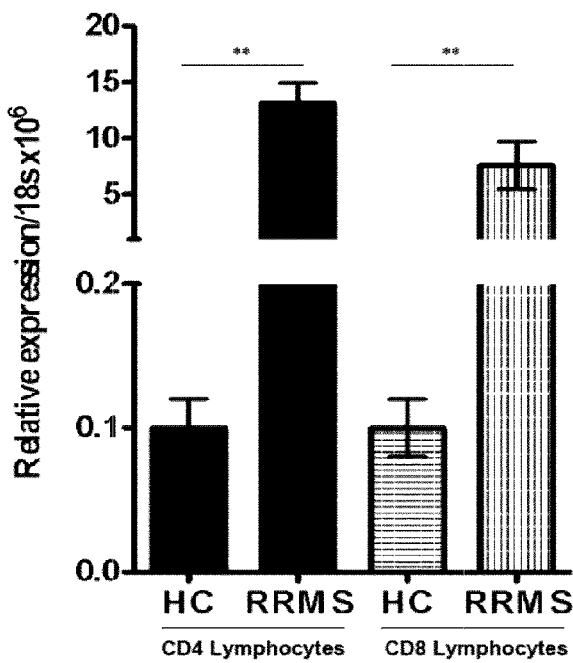
FIG. 7

```
   1 aatagcttga aactggaagg cagagactta gagccgagtg ggacaaagcc tggggctggg
  61 cgggggccat ggcgctgcca tcccgaatcc tgctttggaa acttgtgctt ctgcagagct
 121 ctgctgttct cctgcactca gggtcctcgg tacccgccgc tgctggcagc tccgtggtgt
 181 ccgagtccgc ggtgagctgg gaggcgggcg cccggcggt gctgcgctgc cagagcccgc
 241 gcatggtgtg gacccaggac cggctgcacg accgccagcg cgtgctccac tgggacctgc
 301 gcggccccgg gggtggcccc gcgcggcgcc tgctggactt gtactcggcg ggcgagcagc
 361 gcgtgtacga ggcgcgggac cgcggccgcc tggagctctc ggcctcggcc ttcgacgacg
 421 gcaacttctc gctgctcatc cgcgcggtgg aggagacgga cgcggggctg tacacctgca
 481 acctgcacca tcactactgc cacctctacg agagcctggc cgtccgcctg gaggtcaccg
 541 acggcccccc ggccaccccc gcctactggg acggcgagaa ggaggtgctg gcggtggcgc
 601 gcggcgcacc cgcgcttctg acctgcgtga accgcgggca cgtgtggacc gaccggcacg
 661 tggaggaggc tcaacaggtg gtgcactggg accggcagcc gcccggggtc cgcacgaccc
 721 gcgcggaccg cctgctggac ctctacgcgt cgggcgagcg ccgcgcctac gggccccttt
 781 ttctgcgcga ccgcgtggct gtgggcgcgg atgcctttga gcgcggtgac ttctcactgc
 841 gtatcgagcc gctggaggtc gccgacgagg gcacctactc ctgccacctg caccaccatt
 901 actgtggcct gcacgaacgc cgcgtcttcc acctgacggt cgccgaaccc cacgcggagc
 961 cgccccccg gggctctccg ggcaacggct ccagccacag cggcgcccca ggcccagacc
1021 ccacactggc gcgcggccac aacgtcatca atgtcatcgt ccccgagagc cgagcccact
1081 tcttccagca gctgggctac gtgctggcca cgctgctgct cttcatcctg ctactggtca
1141 ctgtcctcct ggccgcccgc aggcgccgcg gaggctacga atactcggac cagaagtcgg
1201 gaaagtcaaa ggggaaggat gttaacttgg cggagttcgc tgtggctgca ggggaccaga
1261 tgctttacag gagtgaggac atccagctag attacaaaaa caacatcctg aaggagaggg
1321 cggagctggc ccacagcccc ctgcctgcca agtacatcga cctagacaaa gggttccgga
1381 aggagaactg caaatagggg ggccctgggc tcctggctgg ccagcagct gcacctctcc
1441 tgtctgtgct cctcggggca tctcctgatg ctccggggct caccccctt ccagcggctg
1501 gtcccgcttt cctggaattt ggcctgggcg tatgcagagg ccgcctccac cccctctcc
1561 cagggcttg gtggcagcat agccccacc cctgcggcct ttgctcacgg gtggccctgc
1621 ccaccctgg cacaaccaaa atcccactga tgcccatcat gccctcagac ccttctgggc
1681 tctgcccgct ggggggcctga agacattcct ggaggacact cccatcagaa cctggcagcc
1741 ccaaaactgg ggtcagcctc agggcaggag tccactcct caggctct gctcgtccgg
1801 ggctgggaga tgttcctgga ggaggacact cccatcagaa cttggcagcc ttgaagttgg
1861 ggtcagcctc ggcaggagtc ccactcctcc tggggtgctg cctgccaccg agagctcccc
1921 cacctgtacc accatgtggg actccaggca ccatctgttc tccccaggga cctgctgact
1981 tgaatgccag cccttgctcc tctgtgttgc tttgggccac ctggggctgc accccctgcc
2041 cttttctctgc cccatcccta ccctagcctt gctctcagcc accttgatag tcactgggct
2101 ccctgtgact tctgaccctg acacccctcc cttggactct gcctgggctg gagtctaggg
2161 ctggggctac atttggcttc tgtactggct gaggacaggg gagggagtga agttggtttg
2221 gggtggcctg tgttgccact ctcagcaccc cacatttgca tctgctggtg gacctgccac
2281 catcacaata aagtccccat ctgattttta ga
```

FIG. 21A

```
MALPSRILLWKLVLLQSSAVLLHSGSSVPAAAGSSVVSESAVSWEAGARAVLRCQSPRMV
WTQDRLHDRQRVLHWDLRGPGGGPARRLLDLYSAGEQRVYEARDRGRLELSASAFDDGNF
SLLIRAVEETDAGLYTCNLHHYCHLYESLAVRLEVTDGPPATPAYWDGEKEVLAVARGA
PALLTCVNRGHVWTDRHVEEAQQVVHWDRQPPGVPHDRADRLLDLYASGERRAYGPLFLR
DRVAVGADAFERGDFSLRIEPLEVADEGTYSCHLHHHYCGLHERRVFHLTVAEPHAEPPP
RGSPGNGSSHSGAPGPDPTLARGHNVINVIVPESRAHFFQQLGYVLATLLLFILLLVTVL
LAARRRRGGYEYSDQKSGKSKGKDVNLAEFAVAAGDQMLYRSEDIQLDYKNNILKERAEL
AHSPLPAKYIDLDKGFRKENCK
```

FIG. 21B

```
   1 acttagagcc gagtgggaca aagcctgggg ctgggcgggg gccatggcgc tgccatcccg
  61 aatcctgctt tggaaacttg tgcttctgca gagctctgct gttctcctgc actcagggtc
 121 ctcggtaccc gccgctgctg gcagctccgt ggtgtccgag tccgcggtga gctggaggc
 181 gggcgcccgg gcggtgctgc gctgccagag cccgcgcatg gtgtggaccc aggaccggct
 241 gcacgaccgc cagcgcgtgc tccactggga cctgcgcggc cccggggtg gccccgcgcg
 301 gcgcctgctg gacttgtact cggcgggcga gcagcgcgtg tacgaggcg gggaccgcgg
 361 ccgcctggag ctctcggcct cggccttcga cgacggcaac ttctcgctgc tcatccgcgc
 421 ggtggaggag acggacgcgg ggctgtacac ctgcaacctg caccatcact actgccacct
 481 ctacgagagc ctggccgtcc gcctggaggt caccgacggc cccccggcca ccccgccta
 541 ctgggacggc gagaaggagg tgctggcggt ggcgcgcggc gcacccgcgc ttctgacctg
 601 cgtgaaccgc gggcacgtgt ggaccgaccg gcacgtggag gaggctcaac aggtggtgca
 661 ctgggaccgg cagccgcccg ggtccgca cgaccgcgcg gaccgcctgc tggacctcta
 721 cgcgtcgggc gagcgccgcg cctacgggcc cctttttctg cgcgaccgcg tggctgtggg
 781 cgcggatgcc tttgagcgcg gtgacttctc actgcgtatc gagccgctgg aggtcgccga
 841 cgagggcacc tactcctgcc acctgcacca ccattactgt ggcctgcacg aacgccgcgt
 901 cttccacctg acggtcgccg aaccccacgc ggagccgccc cccggggct ctccgggcaa
 961 cggctccagc cacagcggcg ccccaggccc agaccccaca ctggcgcgcg ccacaacgt
1021 catcaatgtc atcgtccccg agagccgagc ccacttcttc agcagctggg gctacgtgct
1081 ggccacgctg ctgctcttca tcctgctact ggtcactgtc ctcctggccg ccgcaggcg
1141 ccgcggaggc tacgaatact cggaccagaa gtcgggaaag tcaaagggga aggatgttaa
1201 cttggcggag ttcgctgtgg ctgcaggga ccagatgctt tacaggagtg aggacatcca
1261 gctagcctcc tctcctccca cagattacaa aacaacatc ctgaaggaga gggcggagct
1321 ggcccacagc cccctgcctg ccaagtacat cgacctagac aaagaccctt ctgggctctg
1381 cccgctgggg gcctgaagac attcctggag gacactccca tcagaacctg cagccccaa
1441 aactggggtc agcctcaggg caggagtccc actcctccag ggctctgctc gtccgggct
1501 gggagatgtt cctggaggag gacactccca tcagaacttg gcagccttga agttggggtc
1561 agcctcggca ggagtcccac tcctcctggg gtgctgcctg ccaccgagag ctcccccacc
1621 tgtaccacca tgtgggactc caggcaccat ctgttctccc cagggacctg ctgacttgaa
1681 tgccagccct tgctcctctg tgttgctttg gccacctgg ggctgcaccc cctgcccttt
1741 ctctgcccca tccctaccct agccttgctc tcagccacct tgatagtcac tgggctccct
1801 gtgacttctg accctgacac ccctcccttg gactctgcct gggctggagt ctagggctgg
1861 ggctacattt ggcttctgta ctggctgagg acaggggagg gagtgaagtt ggtttgggt
1921 ggcctgtgtt gccactctca gcacccaca tttgcatctg ctggtggacc tgccaccatc
1981 acaataaagt ccccatctga tttttaga
```

FIG. 22A

MALPSRILLWKLVLLQSSAVLLHSGSSVPAAAGSSVVSESAVSWEAGARAVLRCQSPRMV
WTQDRLHDRQRVLHWDLRGPGGGPARRLLDLYSAGEQRVYEARDRGRLELSASAFDDGNF
SLLIRAVEETDAGLYTCNLHHHYCHLYESLAVRLEVTDGPPATPAYWDGEKEVLAVARGA
PALLTCVNRGHVWTDRHVEEAQQVVHWDRQPPGVPHDRADRLLDLYASGERRAYGPLFLR
DRVAVGADAFERGDFSLRIEPLEVADEGTYSCHLHHYCGLHERRVFHLTVAEPHAEPPP
RGSPGNGSSHSGAPGPDPTLARGHNVINVIVPESRAHFFQQLGYVLATLLLFILLLVTVL
LAARRRGGYEYSDQKSGKSKGKDVNLAEFAVAAGDQMLYRSEDIQLASSPPTDYKNNIL
KERAELAHSPLPAKYIDLDKDPSGLCPLGA

FIG. 22B

```
   1 aagaaggctg gcggtgtttc ctcttagagg ggagaaactc agcctgggta ggagacccag
  61 ccccacgcag ggaaaactgt gctaacgctt ccgatgtgcg tggcaggtgc ggcggcggcg
 121 aatacggttt gtcctcgagc ctaaccctgt ctgtgttggt gtcagcagtg gccccctac
 181 cacacacaca gggtccctgg cgtcccaaga ccactcctgg cagccccgcc actggctgcg
 241 cctggaagcc gcgtcctcag gcctcgcctg gcatttgctg tcacagaggt tgcttccttg
 301 ggtccgtccg tcctcgcccc tccagcctgg gcgcccccg accctgtct cattccctcc
 361 accacatgca gcacagtcca ggaggctggg gtccaagagg ccatggctg cacccggct
 421 tagtgctgag tccccagtgc ccagcaagcc tggcacccag gaggtggtca gcaaacgctt
 481 ctgaacgaca ggaagtggga ctcttcagcc atcgatgatc cgctgtgcgg ccacaggctc
 541 tgctgttctc ctgcactcag ggtcctcggt acccgccgct gctggcagct ccgtggtgtc
 601 cgagtccgcg gtgagctggg aggcgggcgc ccgggcggtg ctgcgctgcc agagcccgcg
 661 catggtgtgg acccaggacc ggctgcacga ccgccagcgc gtgctccact gggacctgcg
 721 cggccccggg ggtggccccg cgcggcgcct gctggacttg tactcggcgg gcgagcagcg
 781 cgtgtacgag cgcgggacc gcggccgcct ggagctctcg gcctcggcct tcgacgacgg
 841 caacttctcg ctgctcatcc gcgcggtgga ggagacggac gcgggctgt acacctgcaa
 901 cctgcaccat cactactgcc acctctacga gagcctggcc gtccgcctgg aggtcaccga
 961 cggcccccg gccaccccg cctactggga cggcgagaag gaggtgctgg cggtggcgcg
1021 cggcgcaccc gcgcttctga cctgcgtgaa ccgcgggcac gtgtggaccg accggcacgt
1081 ggaggaggct caacaggtgg tgcactggga ccggcagccg cccggggtcc cgcacgaccg
1141 cgcggaccgc ctgctggacc tctacgcgtc gggcgagcgc cgcgcctacg gccccttttt
1201 tctgcgcgac cgcgtggctg tgggcgcgga tgcctttgag cgcggtgact tctcactgcg
1261 tatcgagccg ctggaggtcg ccgacgaggg cacctactcc tgccacctgc accaccatta
1321 ctgtggcctg cacgaacgcc gcgtcttcca cctgacggtc gccgaacccc acgcggagcc
1381 gccccccgg ggctctccgg caacggctc cagccacagc ggcgccccag gcccagaccc
1441 cacactggcg cgcggccaca acgtcatcaa tgtcatcgtc cccgagagcc gagcccactt
1501 cttccagcag ctgggctacg tgctggccac gctgctgctc ttcatcctgc tactggtcac
1561 tgtcctcctg gccgcccgca ggcgccgcgg aggctacgaa tactcggacc agaagtcggg
1621 aaagtcaaag gggaaggatg ttaacttggc ggagttcgct gtggctgcag gggaccagat
1681 gctttacagg agtgaggaca tccagctaga ttacaaaaac aacatcctga aggagagggc
1741 ggagctggcc cacagccccc tgcctgccaa gtacatcgac ctagacaaag ggttccggaa
1801 ggagaactgc aaatagggag gccctgggct cctggctggg ccagcagctg cacctctcct
1861 gtctgtgctc ctcgggcat ctcctgatgc tccggggctc accccccttc cagcggctgg
1921 tcccgctttc ctggaatttg gcctgggcgt atgcagaggc cgcctccaca ccctctccc
1981 aggggcttgg tggcagcata gccccaccc ctgcggcctt tgctcacggg tggccctgcc
2041 cacccctggc acaaccaaaa tcccactgat gcccatcatg ccctcagacc cttctgggct
2101 ctgcccgctg ggggcctgaa gacattcctg gaggacactc ccatcagaac ctggcagccc
2161 caaaactggg gtcagcctca gggcaggagt cccactcctc cagggctctg ctcgtccggg
2221 gctgggagat gttcctggag gaggacactc ccatcagaac ttggcagcct tgaagttggg
2281 gtcagcctcg gcaggagtcc cactcctcct ggggtgctgc ctgccaccga gagctccccc
2341 acctgtacca ccatgtggga ctccaggcac atctgttct ccccagggac ctgctgactt
2401 gaatgccagc ccttgctcct ctgtgttgct ttgggccacc tggggctgca ccccctgccc
2461 tttctctgcc ccatccctac cctagccttg ctctcagcca ccttgatagt cactgggctc
2521 cctgtgactt ctgaccctga cacccctccc ttggactctg cctgggctgg agtctagggc
2581 tggggctaca tttggcttct gtactggctg aggacagggg agggagtgaa gttggtttgg
2641 ggtggcctgt gttgccactc tcagcacccc acatttgcat ctgctggtgg acctgccacc
2701 atcacaataa agtccccatc tgatttttag a
```

FIG. 23A

MIRCAATGSAVLLHSGSSVPAAAGSSVVSESAVSWEAGARAVLRCQSPRMVWTQDRLHDR
QRVLHWDLRGPGGGPARRLLDLYSAGEQRVYEARDRGRLELSASAFDDGNFSLLIRAVEE
TDAGLYTCNLHHHYCHLYESLAVRLEVTDGPPATPAYWDGEKEVLAVARGAPALLTCVNR
GHVWTDRHVEEAQQVVHWDRQPPGVPHDRADRLLDLYASGERRAYGPLFLRDRVAVGADA
FERGDFSLRIEPLEVADEGTYSCHLHHHYCGLHERRVFHLTVAEPHAEPPPRGSPGNGSS
HSGAPGPDPTLARGHNVINVIVPESRAHFFQQLGYVLATLLLFILLLVTVLLAARRRRGG
YEYSDQKSGKSKGKDVNLAEFAVAAGDQMLYRSEDIQLDYKNNILKERAELAHSPLPAKY
IDLDKGFRKENCK

FIG. 23B

```
   1 atgtcctcgg accttcttgt ccctccaagg gtgcggtcac caccctccc caggcctgac
  61 cggtgagggg ctgggcctct gctcccacac tgcccctccc cagcaggcca gcaacgatgg
 121 gggaggccaa ggggcccggc aggagccaga ggggcggtc cccagaccgt agacaggccc
 181 aggcctccgt gatgtcaccg cgggtgctaa ggaggggag ggggtagggc tgtttttctg
 241 gagagagact tagagccgag tgggacaaag cctggggctg ggcggggggcc atggcgctgc
 301 catcccgaat cctgctttgg aaacttgtgc ttctgcagag ctctgctgtt ctcctgcact
 361 cagcggtgga ggagacggac gcggggctgt acacctgcaa cctgcaccat cactactgcc
 421 acctctacga gagcctggcc gtccgcctgg aggtcaccga cggcccccg ccacccccg
 481 cctactggga cggcgagaag gaggtgctgg cggtggcgcg cggcgcaccc gcgcttctga
 541 cctgcgtgaa ccgcgggcac gtgtggaccg accggcacgt ggaggaggct caacaggtgg
 601 tgcactggga ccggcagccg cccggggtcc cgcacgaccg cgcggaccgc tgctggacc
 661 tctacgcgtc gggcgagcgc cgcgcctacg ggccccttt tctgcgcgac cgcgtggctg
 721 tgggcgcgga tgccttttgag cgcggtgact tctcactgcg tatcgagccg ctggaggtcg
 781 ccgacgaggg cacctactcc tgccacctgc accaccatta ctgtggcctg cacgaacgcc
 841 gcgtcttcca cctgacggtc gccgaacccc acgcggagcc gccccccgg ggctctccgg
 901 gcaacggctc cagccacagc ggcgcccag gcccagaccc cacactggcg cgcggccaca
 961 acgtcatcaa tgtcatcgtc cccgagagcc gagcccactt cttccagcag ctgggctacg
1021 tgctggccac gctgctgctc ttcatcctgc tactggtcac tgtcctcctg gccgccgca
1081 ggcgccgcgg aggctacgaa tactcggacc agaagtcggg aaagtcaaag gggaaggatg
1141 ttaacttggc ggagttcgct gtggctgcag ggaccagat gctttacagg agtgaggaca
1201 tccagctaga ttacaaaaac aacatcctga aggagagggc ggagctggcc cacagccccc
1261 tgcctgccaa gtacatcgac ctagacaaag ggttccggaa ggagaactgc aaatagggag
1321 gccctgggct cctggctggg ccagcagctg cacctctcct gtctgtgctc ctcgggcat
1381 ctcctgatgc tccggggctc accccctctc cagcggctgg tcccgctttc ctggaattg
1441 gcctgggcgt atgcagaggc cgcctccaca cccctctccc aggggcttgg tggcagcata
1501 gcccccaccc ctgcggcctt tgctcacggg tggccctgcc caccctggc acaaccaaaa
1561 tcccactgat gcccatcatg ccctcagacc cttctgggct ctgcccgctg ggggcctgaa
1621 gacattcctg gaggacactc ccatcagaac ctggcagccc caaactggg gtcagcctca
1681 gggcaggagt cccactcctc cagggctctg tcgtccggg gctgggagat gttcctggag
1741 gaggacactc ccatcagaac ttggcagcct gaagttgggg gtcagcctcg gcaggagtcc
1801 cactcctcct ggggtgctgc ctgccaccga gctcccccc acctgtacca ccatgtggga
1861 ctccaggcac catctgttct ccccagggac ctgctgactt gaatgccagc ccttgctcct
1921 ctgtgttgct ttgggccacc tggggctgca cccccctgccc tttctctgcc ccatccctac
1981 cctagccttg ctctcagcca ccttgatagt cactgggctc cctgtgactt ctgaccctga
2041 cacccctccc ttggactctg cctgggctgg agtctagggc tggggctaca tttggcttct
2101 gtactggctg aggacagggg agggagtgaa gttggtttgg ggtggcctgt gttgccactc
2161 tcagcacccc acatttgcat ctgctggtgg acctgccacc atcacaataa agtccccatc
2221 tgattttag a
```

FIG. 24A

MALPSRILLWKLVLLQSSAVLLHSAVEETDAGLYTCNLHHHYCHLYESLAVRLEVTDGPP
ATPAYWDGEKEVLAVARGAPALLTCVNRGHVWTDRHVEEAQQVVHWDRQPPGVPHDRADR
LLDLYASGERRAYGPLFLRDRVAVGADAFERGDFSLRIEPLEVADEGTYSCHLHHHYCGL
HERRVFHLTVAEPHAEPPPRGSPGNGSSHSGAPGPDPTLARGHNVINVIVPESRAHFFQQ
LGYVLATLLLFILLLVTVLLAARRRRGGYEYSDQKSGKSKGKDVNLAEFAVAAGDQMLYR
SEDIQLDYKNNILKERAELAHSPLPAKYIDLDKGFRKENCK

FIG. 24B

ATGGATTTTCAGGTGCAGATTTTCAGCTTCCTGCTAATCAGTGCCTCAGTCATAATGTCCAGAGGA
CAAATTGTTCTCACCCAGTCTCCAGCAATCATGTCTGCATTTCTAGGGGAGGAGATCACCCTAACC
TGCAGTGCCAGCTCGAGTGTAAGTTACATGCACTGGTACCAGCAGAAGTCAGGCACTTCTCCCAAA
CTCTTGATTTATAGCACATCCAACCTGGCTTCTGGAGTCCCTTCTCGCTTCAGTGGCAGTGGGTCT
GGGACCTTTTATTCTCTCACAATCAGCAGTGTGGAGGCTGAAGATGCTGCCGATTATTACTGCCAT
CAGTGGAGTAGTTATCGGACGTTCGGTGGAGGCACCAAGCTGGAAATCAAAAGGGCT<u>GATGCTGCA
CCAACTGTA</u>

FIG. 25A

*MDFQVQIFSFLLISASVIMSRG*QIVLTQSPAIMSAFLGEEITLTCSASSSVSYMHWYQQK
SGTSPKLLIYSTSNLASGVPSRFSGSGSGTFYSLTISSVEAEDAADYYCHQWSSYRTFGG
GTKLEIKRA<u>DAAPTV</u>

FIG. 25B

ATGAAC*T*TTGTGCTCAGCCTGATTTTCCTTGCCCTCATTTTAAAAGGTGTCCAGTGTGAAGTGCAG
CTGGTGGAGTCTGGGGGAGGCTTAGTGAAGCCTGGAGGGTCCCTGAAACTCTCCTGTGCAGCCTCT
GGATTCACTTTCATTAGCTATGCCATGTCTTGGGTTCGCCAGACTCCGGAGAAGAGGCTGGAGTGG
GTCGCAACCATTAGTAGTGGTGGTAGTTACACCTACTATCCACACAGTGTGAAGGGTCGATTCACC
ATCTCCAGAGACAATGCCAGGAACACCCTGTACCTGCAAATGAGCAGTCTGAGGTCTGAGGACACG
GCCATGTATTACTGTGCAAGACTGGATGGTCCCTCATATGCTATGGACTACTGGGGTCAAGGAACC
TCAGTCACCGTCTCCTCAG<u>CCAAAACGACACCCCCATCTGTCTATCCACTGGCCCCT</u>

FIG. 25C

*MNFVLSLIFLALILKGVQC*EVQLVESGGGLVKPGGSLKLSCAASGFTFISYAMSWVRQTPEKRLEW
VATISSGGSYTYYPHSVKGRFTISRDNARNTLYLQMSSLRSEDTAMYYCARLDGPSYAMDYWGQGT
SVTVS<u>SAKTTPPSVYPLAP</u>

FIG. 25D

| Query protein sequence | Q | I | V | L | T | Q | S | P | A | I | M | S | A | F | L | G | E | E | I | T |
|---|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |
| Chothia+ numbering | L1 | L2 | L3 | L4 | L5 | L6 | L7 | L8 | L9 | L10 | L11 | L12 | L13 | L14 | L15 | L16 | L17 | L18 | L19 | L20 |
| Kabat numbering | L1 | L2 | L3 | L4 | L5 | L6 | L7 | L8 | L9 | L10 | L11 | L12 | L13 | L14 | L15 | L16 | L17 | L18 | L19 | L20 |

REGIONS: CHOTHIA — LFR1
ABM — LFR1
KABAT — LFR1
CONTACT — LFR1

| L | T | C | S | A | S | S | S | V | S | Y | M | H | W | Y | Q | Q | K | S | G | T | S | P |
|---|---|---|---|---|---|---|---|---|---|---|---|---|---|---|---|---|---|---|---|---|---|---|
| L21 | L22 | L23 | L24 | L25 | L26 | L27 | L28 | L29 | L30 | | L32 | L33 | L34 | L35 | L36 | L37 | L38 | L39 | L40 | L41 | L42 | L43 | L44 |
| L21 | L22 | L23 | L24 | L25 | L26 | L27 | L28 | L29 | | L31 | L32 | L33 | L34 | L35 | L36 | L37 | L38 | L39 | L40 | L41 | L42 | L43 | L44 |
| L21 | L22 | L23 | L24 | L25 | L26 | L27 | | L29 | L30 | L31 | L32 | L33 | L34 | L35 | L36 | L37 | L38 | L39 | L40 | L41 | L42 | L43 | L44 |

CDR-L1 / LFR2

| K | L | L | I | Y | S | T | S | N | L | A | S | G | V | P | S | R | F | S | G | S | G | S |
|---|---|---|---|---|---|---|---|---|---|---|---|---|---|---|---|---|---|---|---|---|---|---|
| L45 | L46 | L47 | L48 | L49 | L50 | L51 | L52 | L53 | L54 | L55 | L56 | L57 | L58 | L59 | L60 | L61 | L62 | L63 | L64 | L65 | L66 | L67 |
| L45 | L46 | L47 | L48 | L49 | L50 | L51 | L52 | L53 | L54 | L55 | L56 | L57 | L58 | L59 | L60 | L61 | L62 | L63 | L64 | L65 | L66 | L67 |
| L45 | L46 | L47 | L48 | L49 | L50 | L51 | L52 | L53 | L54 | L55 | L56 | L57 | L58 | L59 | L60 | L61 | L62 | L63 | L64 | L65 | L66 | L67 |

CDR-L2 / LFR3

| G | T | F | Y | S | L | T | I | S | S | V | E | A | E | D | A | A | D | Y | Y | C | H | Q |
|---|---|---|---|---|---|---|---|---|---|---|---|---|---|---|---|---|---|---|---|---|---|---|
| L68 | L69 | L70 | L71 | L72 | L73 | L74 | L75 | L76 | L77 | L78 | L79 | L80 | L81 | L82 | L83 | L84 | L85 | L86 | L87 | L88 | L89 | L90 |
| L68 | L69 | L70 | L71 | L72 | L73 | L74 | L75 | L76 | L77 | L78 | L79 | L80 | L81 | L82 | L83 | L84 | L85 | L86 | L87 | L88 | L89 | L90 |
| L68 | L69 | L70 | L71 | L72 | L73 | L74 | L75 | L76 | L77 | L78 | L79 | L80 | L81 | L82 | L83 | L84 | L85 | L86 | L87 | L88 | L89 | L90 |

CDR-L3

| W | S | S | Y | R | T | F | G | G | G | T | K | L | E | I | K | R | A |
|---|---|---|---|---|---|---|---|---|---|---|---|---|---|---|---|---|---|
| L91 | L92 | L93 | L94 | L96 | L97 | L98 | L99 | L100 | L101 | L102 | L103 | L104 | L105 | L106 | L107 | L108 | L109 |
| L91 | L92 | L93 | L94 | L96 | L97 | L98 | L99 | L100 | L101 | L102 | L103 | L104 | L105 | L106 | L107 | L108 | L109 |
| L91 | L92 | L93 | L94 | L96 | L97 | L98 | L99 | L100 | L101 | L102 | L103 | L104 | L105 | L106 | L107 | L108 | L109 |

LFR4

FIG. 26A

| Query protein sequence | E | V | Q | L | V | E | S | G | G | G | L | V | K | P | G | G | S | L | K | L |
|---|---|---|---|---|---|---|---|---|---|---|---|---|---|---|---|---|---|---|---|---|
| Chothia numbering | H1 | H2 | H3 | H4 | H5 | H6 | H7 | H8 | H9 | H10 | H11 | H12 | H13 | H14 | H15 | H16 | H17 | H18 | H19 | H20 |
| Chothia+ numbering | H1 | H2 | H3 | H4 | H5 | H6 | H7 | H8 | H9 | H10 | H11 | H12 | H13 | H14 | H15 | H16 | H17 | H18 | H19 | H20 |
| Kabat numbering | H1 | H2 | H3 | H4 | H5 | H6 | H7 | H8 | H9 | H10 | H11 | H12 | H13 | H14 | H15 | H16 | H17 | H18 | H19 | H20 |
| REGIONS: CHOTHIA | | | | | | | | | | | | | | | | | | | | |
| ABM | | | | | | | | | | | HFR1 | | | | | | | | | |
| KABAT | | | | | | | | | | | HFR1 | | | | | | | | | |
| CONTACT | | | | | | | | | | | HFR1 | | | | | | | | | |
| | | | | | | | | | | | HFR1 | | | | | | | | | |

| | S | C | A | A | S | G | F | T | F | I | S | Y | A | M | S | W | V | R | Q | T | P | E | K |
|---|---|---|---|---|---|---|---|---|---|---|---|---|---|---|---|---|---|---|---|---|---|---|---|
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |
| | H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |

CDR-H1 / HFR2 / CDR-H1 / HFR2 / CDR-H1 / HFR2 / CDR-H1 / HFR2

| | R | L | E | W | V | A | T | I | S | S | G | G | S | Y | T | Y | Y | P | H | S | V | K | G |
|---|---|---|---|---|---|---|---|---|---|---|---|---|---|---|---|---|---|---|---|---|---|---|---|
| | H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 |
| | H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 |
| | H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 |

CDR-H2 / HFR3 / CDR-H2 / HFR3 / CDR-H2 / HFR3

| | R | F | T | I | S | R | D | N | A | R | N | T | L | Y | L | Q | M | S | S | L | R | S | E |
|---|---|---|---|---|---|---|---|---|---|---|---|---|---|---|---|---|---|---|---|---|---|---|---|
| | H66 | H67 | H68 | H69 | H70 | H71 | H72 | H73 | H74 | H75 | H76 | H77 | H78 | H79 | H80 | H81 | H82 | H82A | H82B | H82C | H83 | H84 | H85 |
| | H66 | H67 | H68 | H69 | H70 | H71 | H72 | H72A | H72B | H72C | H73 | H74 | H75 | H76 | H77 | H78 | H79 | H80 | H81 | H82 | H83 | H84 | H85 |
| | H66 | H67 | H68 | H69 | H70 | H71 | H72 | H73 | H74 | H75 | H76 | H77 | H78 | H79 | H80 | H81 | H82 | H82A | H82B | H82C | H83 | H84 | H85 |

HFR3

| | D | T | A | M | Y | Y | C | A | R | L | D | G | P | S | Y | A | M | D | Y | W | G | Q | G |
|---|---|---|---|---|---|---|---|---|---|---|---|---|---|---|---|---|---|---|---|---|---|---|---|
| | H86 | H87 | H88 | H89 | H90 | H91 | H92 | H93 | H94 | H95 | H96 | H97 | H98 | H99 | H100 | H100A | H100B | H101 | H102 | H103 | H104 | H105 | H106 |
| | H86 | H87 | H88 | H89 | H90 | H91 | H92 | H93 | H94 | H95 | H96 | H97 | H98 | H99 | H100 | H100A | H100B | H101 | H102 | H103 | H104 | H105 | H106 |
| | H86 | H87 | H88 | H89 | H90 | H91 | H92 | H93 | H94 | H95 | H96 | H97 | H98 | H99 | H100 | H100A | H100B | H101 | H102 | H103 | H104 | H105 | H106 |

CDR-H3 / HFR4 / CDR-H3 / HFR4 / CDR-H3 / HFR4 / CDR-H3 / HFR4

| | T | S | V | T | V | S | S |
|---|---|---|---|---|---|---|---|
| | H107 | H108 | H109 | H110 | H111 | H112 | H113 |
| | H107 | H108 | H109 | H110 | H111 | H112 | H113 |
| | H107 | H108 | H109 | H110 | H111 | H112 | H113 |

FIG. 26B

ATGGAGACAGACACACTCCTGTTATGGGTACTGCTGCTCTGGGTTCCAGGTTCCACTGGTGACATT
GTGCTGACACAGTCTCCTGCTTCCTTAACTGTATCTCTGGGGCAGAGGGCCACCATCTCATGCAGG
GCCAGCAAAAGTGTCAGTACATCTGGCTATAGTTA*T*ATACACTGGTACCAACAGAAACCAGGACAG
CCACCCAAACTCCTCATCTATCTTGCATCCAACCTAGAATCTGGGGTCCCTGCCAGGTTCAGTGGC
AGTGGGTCTGGGACAGACTTCACCCTCAACATCCATCCTGTGGAGGAGGAGGATGCTGCAACCTAT
TACTGTCAGCACAGTAGGGAGCTTCCGCTCACGTTCGGTGCTGGGACCAAGCTGGAGCTGAAACGG
GCT<u>GATGCTGCACCAACTGTA</u>

FIG. 27A

*METDTLLLWVLLLWVPGSTG*DIVLTQSPASLTVSLGQRATISCRASKSVSTSGYSYIHWY
QQKPGQPPKLLIYLASNLESGVPARFSGSGSGTDFTLNIHPVEEEDAATYYCQHSRELPL
TFGAGTKLELKRA<u>DAAPTV</u>

FIG. 27B

ATGGACAGGCTTACTTCCTCATTCCTACTCCTGATTGTTCCTGTCTATGTCCTATCCCAGGTTACT
CTGAAAGAGTCTGGCCCTGGGATATTGCAGCCCTCCCAGACCCTCAGTCTGACTTGTTCTTTCTCT
GGGTTTTCACTGAGCACTTTTGGTGTGGGTGTGAGCTGGATTCGTCAGCCTTCAGGGAATGGTCTG
GAGTGGCTGGCACACATTTTTTGGGATGATGACAAGCACTATAACCCATCCTTGAAGAGCCGGCTC
ACAATCTCCAAGGATACCTCCAACAACCAGGTTTTCCTCAAGATCACGACTGTGGACACTGCAGAT
ACTGCCACATACTACTGTGCTCAAGGGAATTACTACGCTAGTGGTTACTTCTTTGAC*T*ACTGGGGC
CAAGGCACCACTCTCACAGTCTCCTC<u>AGCCAAAACAACACCCCCATCAGTCTATCCACTGGCCCCT</u>

FIG. 27C

*MDRLTSSFLLLIVPVYVLS*QVTLKESGPGILQPSQTLSLTCSFSGFSLSTFGVGVSWIRQ
PSGNGLEWLAHIFWDDDKHYNPSLKSRLTISKDTSNNQVFLKITTVDTADTATYYCAQGN
YYASGYFFD*Y*WGQGTTLTVSS<u>AKTTPPSVYPLAP</u>

DICAM-SPECIFIC ANTIBODIES AND USES THEREOF

CROSS REFERENCE TO RELATED APPLICATIONS

The present application is a National Entry Application of PCT Application No PCT/CA2015/051338, filed on Dec. 17, 2015, which claims the benefits of U.S. Provisional Application Ser. No. 62/094,590, filed on Dec. 19, 2014, and of U.S. Provisional Application Ser. No. 62/235,781, filed on Oct. 1, 2015, which are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9355-7_ST25.txt, 47,378 bytes in size, generated on Jun. 19, 2017 and filed via EFS-Web, is provided in lieu of a paper copy. This Sequence Listing is hereby incorporated by reference into the specification for its disclosures.

FIELD OF THE INVENTION

The present invention generally relates to Dual Ig domain containing cell adhesion molecule (DICAM) (also known as limitrin or Matrix-remodeling-associated protein 8, MXRA8), and more particularly to binding reagents directed against DICAM and uses thereof in the diagnosis, prevention and/or treatment of diseases and conditions associated with inflammation, such as neuroinflammation (e.g., multiple sclerosis).

BACKGROUND OF THE INVENTION

A specific subset of CD4$^+$ T cells, termed $T_H17$ cells (T helper 17 cells), has been implicated in the pathogenesis of a number of inflammatory/autoimmune diseases, including those neuroinflammatory conditions involving CNS infiltration of T cells, such as multiple sclerosis (MS).

MS is a chronic inflammatory/autoimmune demyelinating disease of the central nervous system (CNS) mostly affecting young adults between 20 and 40 years old, characterized by inflammatory attacks to the central nervous system. Clinically, the disease ranges from relapsing-remitting to chronic progressive in nature. To date, MS is the first cause of non-traumatic disability in young people. Pathologically, the disease is characterized by the presence of T lymphocytes, immunoglobulins, activated macrophages and pro-inflammatory cytokines (i.e., IL-12, IL-23, IL-1 and IL-6) within focal CNS lesions, causing myelin loss, oligodendrocyte death and axonal damage.

There are few treatment regimens currently used in MS. Corticosteroids have anti-inflammatory and immunosuppressive effects. However, the responsiveness to corticosteroids declines over time, and extended use may lead to adrenal suppression, cardiovascular collapse and arrhythmias. (C. F. Lacy et al., *Drug information handbook* 8$^{th}$ Edition, 2001, pp. 549-551).

Interferon-β has been used as a therapy for patients with active Relapsing/Remitting Multiple Sclerosis (RRMS) since the 1980's. Recombinant IFN is available in 3 drugs: IFNβ-1b (Betaseron™) and two IFN-β-Ia preparations (Avonex™ and Rebif™). These drugs reduce the rate of clinical relapse. However, neutralizing antibodies develop against these drugs rendering them ineffective with time. Also, flu-like symptoms are a prominent side effect early on in the treatment.

Glatiramer acetate (Copaxone™) is a synthetic co-polymer of tyrosine, glutamate, alanine and lysine, thought to mimic myelin basic protein (MBP) and thus, block T cell recognition of MBP (Karin N. et al., (1994) *J Exp Med.* 180(6): 2227-37). However, treatment with this drug may cause cardiovascular problems such as chest pain, flushing and tachycardia, and respiratory problems such as dyspnea (C. F. Lacy et al., supra).

Another drug that has been approved for the use in RRMS and secondary progressive MS is mitoxantrone, which however has long-term side effects causing cardiac toxicity.

Therefore, while there are a few moderately effective treatments for RRMS and secondary progressive MS, problems still exist in treating MS, and there are still no proven treatments, for example, for primary progressive MS.

Furthermore, there is currently no monoclonal antibodies directed against DICAM that may be used for flow cytometry applications and/or that may be used to block DICAM activity.

Thus, there is a need in the art to identify and use molecules that are involved in the infiltration of inflammatory immune cells such as $T_H17$ cells into inflamed tissues. These molecules can be targets to design therapeutic agents for inflammatory/autoimmune conditions, such as MS and Parkinson's disease (PD), as well as other $T_H17$-mediated inflammatory conditions not associated with the central nervous system. There is also a need to identify novel antibodies that can bind to and/or are capable of reducing, interfering, or otherwise blocking the interaction between DICAM expressed on the surface of $T_H17$ and its identified ligand.

There is also a continued need for novel reagents and methods for detecting DICAM.

The present description refers to a number of documents, the content of which is herein incorporated by reference in their entirety.

SUMMARY OF THE INVENTION

The present invention generally relates to novel binding molecules (e.g., antibodies or antigen-binding fragments thereof) specific for DICAM, and uses thereof such as in the diagnosis, prevention and/or treatment of diseases and conditions associated with autoimmunity/inflammation, such as neuroinflammation (e.g., multiple sclerosis).

The present invention relates to the following items [1] to [45]:

1. An antibody or an antigen-binding fragment thereof that specifically binds to an epitope located within a domain corresponding to residues 57-71 or 372-385 of SEQ ID NO:18.
2. The antibody or antigen-binding fragment thereof according to item 1, which binds to an epitope located within a domain corresponding residues 372-385 of SEQ ID NO:18.
3. The antibody or antigen-binding fragment thereof according to item 1, which binds to an epitope located within a domain corresponding residues 57-71 of SEQ ID NO:18.
4. The antibody or antigen-binding fragment thereof according to any one of items 1 to 3, wherein the antibody or antigen-binding fragment thereof recognizes human Dual Ig domain containing cell adhesion molecule (DICAM) by Western blot.
5. The antibody or antigen-binding fragment thereof according to any one of items 1 to 4, wherein the antibody or antigen-binding fragment thereof recognizes human DICAM at the surface of a cell.

6. The antibody or antigen-binding fragment thereof according to any one of items 1 to 5, wherein the antibody or antigen-binding fragment thereof blocks or inhibits the binding of DICAM to αVβ3 integrin.

7. The antibody or antigen-binding fragment thereof according to any one of items 1 to 6, wherein the antibody or antigen-binding fragment thereof blocks or inhibits the migration of $T_H17$ lymphocytes across a vascular epithelium or endothelium.

8. The antibody or antigen-binding fragment thereof according to item 7, wherein the vascular epithelium or endothelium is the blood-brain barrier.

9. The antibody or antigen-binding fragment thereof according to any one of items 1 to 8, wherein the antibody or antigen-binding fragment thereof comprises the light chain and/or heavy chain complementary determining regions (CDRs) set forth in Table I or Table II:

TABLE I

| Region | Numbering Scheme | Sequence | SEQ ID NO: |
|---|---|---|---|
| CDR-L1 | Kabat | SASSSVSYMH-- | 1 |
|  | Chothia | SASSSVSYMH-- | 1 |
|  | AbM | SASSSVSYMH-- | 1 |
|  | Contact | ------SYMHWY | 2 |
| CDR-L2 | Kabat | ----STSNLAS | 3 |
|  | Chothia | ----STSNLAS | 3 |
|  | AbM | ----STSNLAS | 3 |
|  | Contact | LLIYSTSNLAS | 4 |
| CDR-L3 | Kabat | HQWSSYRT | 5 |
|  | Chothia | HQWSSYRT | 5 |
|  | AbM | HQWSSYRT | 5 |
|  | Contact | HQWSSYR- | 6 |
| CDR-H1 | Kabat | -----SYAMS | 7 |
|  | Chothia | GFTFISY--- | 8 |
|  | AbM | GFTFISYAMS | 9 |
|  | Contact | ----ISYAMS | 10 |
| CDR-H2 | Kabat | ---TISSGGSYTYYPHSVKG | 11 |
|  | Chothia | -----SSGGSY-------- | 12 |
|  | AbM | ---TISSGGSYTY------ | 13 |
|  | Contact | WVATISSGGSYTY------ | 14 |
| CDR-H3 | Kabat | --LDGPSYAMDY | 15 |
|  | Chothia | --LDGPSYAMDY | 15 |
|  | AbM | --LDGPSYAMDY | 15 |
|  | Contact | ARLDGPSYAMD- | 16 |

TABLE II

| Region | Numbering Scheme | Sequence | SEQ ID NO: |
|---|---|---|---|
| CDR-L1 | Kabat | RASKSVSTSGYSYIH-- | 36 |
|  | Chothia | RASKSVSTSGYSYIH-- | 36 |
|  | AbM | RASKSVSTSGYSYIH-- | 36 |
|  | Contact | ------STSGYSYIHWY | 37 |
| CDR-L2 | Kabat | ----LASNLES | 38 |
|  | Chothia | ----LASNLES | 38 |
|  | AbM | ----LASNLES | 38 |
|  | Contact | LLIYLASNLE- | 39 |
| CDR-L3 | Kabat | QHSRELPLT | 40 |
|  | Chothia | QHSRELPLT | 40 |
|  | AbM | QHSRELPLT | 40 |
|  | Contact | QHSRELPL- | 41 |
| CDR-H1 | Kabat | -----TFGVGVS | 42 |
|  | Chothia | GFSLSTFGV--- | 43 |
|  | AbM | GFSLSTFGVS | 44 |
|  | Contact | ----STFGVGVS | 45 |
| CDR-H2 | Kabat | ---HIFWDDDKHYNPSLKS | 46 |
|  | Chothia | -----FWDDD-------- | 47 |
|  | AbM | ---HIFWDDDKH------ | 48 |
|  | Contact | WLAHIFWDDDKH------ | 49 |
| CDR-H3 | Kabat | --GNYYASGYFFDY | 50 |
|  | Chothia | --GNYYASGYFFDY | 50 |
|  | AbM | --GNYYASGYFFDY | 50 |
|  | Contact | AQGNYYASGYFFDY | 51 |

10. The antibody or antigen-binding fragment thereof according to item 9, wherein the antibody or antigen-binding fragment thereof comprises the CDR-L1, CDR-L2, CDR-L3, CDR-H1, CDR-H2 and CDR-H3 set forth in Table I or Table II.

11. The antibody or antigen-binding fragment thereof according to item 10, wherein the antibody or antigen-binding fragment thereof comprises a light chain variable region comprising residues 23 to 129 of SEQ ID NO:26.

12. The antibody or antigen-binding fragment thereof according to item 10 or 11, wherein the antibody or antigen-binding fragment thereof comprises a heavy chain variable region comprising residues 20 to 137 of SEQ ID NO:28.

13. The antibody or antigen-binding fragment thereof according to item 10, wherein the antibody or antigen-binding fragment thereof comprises a light chain variable region comprising residues 21 to 133 of SEQ ID NO:30.

14. The antibody or antigen-binding fragment thereof according to item 10 or 13, wherein the antibody or antigen-binding fragment thereof comprises a heavy chain variable region comprising residues 20 to 141 of SEQ ID NO:32.

15. The antibody or antigen-binding fragment thereof according to any one of items 1 to 14, which is a monoclonal antibody.

16. The antibody or antigen-binding fragment thereof according to any one of items 1 to 14, which is a recombinant antibody.

17. The antibody or antigen-binding fragment thereof according to any one of items 1 to 16, wherein said antibody or antigen-binding fragment thereof comprises a detectable label attached thereto.

18. The antibody or antigen-binding fragment thereof according to item 17, wherein said detectable label is a fluorophore.

19. A composition comprising the antibody or antigen-binding fragment thereof according to any one of items 1 to 18, and an excipient.

20. The composition of item 19, wherein said composition is a pharmaceutical composition, and said excipient is a pharmaceutically-acceptable excipient.

21. The antibody or antigen-binding fragment thereof according to any one of items 6 to 18, or the composition of item 20, for use as a medicament.

22. The antibody or antigen-binding fragment thereof according to any one of items 6 to 18, or the composition of item 20, for use in the treatment of an inflammatory or autoimmune condition in a subject.

23. The antibody or antigen-binding fragment thereof for use according to item 22, wherein said inflammatory condition is a neuroinflammatory condition.

24. The antibody or antigen-binding fragment thereof for use according to item 23, wherein said neuroinflammatory condition is multiple sclerosis (MS).

25. A method for treating an inflammatory or autoimmune condition in a subject in need thereof, said method comprising administering to said subject an effective amount of the antibody or antigen-binding fragment thereof according to any one of items 6 to 18, or the composition of item 20.

26. The method of item 25, wherein said inflammatory condition is a neuroinflammatory condition.
27. The method of item 26, wherein said neuroinflammatory condition is multiple sclerosis (MS).
28. Use of the antibody or antigen-binding fragment thereof according to any one of items 6 to 18, or the composition of item 20, as a medicament.
29. Use of the antibody or antigen-binding fragment thereof according to any one of items 6 to 18, or the composition of item 20, for treating an inflammatory or autoimmune condition in a subject.
30. Use of the antibody or antigen-binding fragment thereof according to any one of items 6 to 18, or the composition of item 20, for the manufacture of a medicament for treating an inflammatory or autoimmune condition in a subject.
31. The use of item 29 or 30, wherein said inflammatory or autoimmune condition is a neuroinflammatory condition.
32. The use of item 31, wherein said neuroinflammatory condition is multiple sclerosis.
33. A method for detecting DICAM at the surface of a cell comprising contacting said cell with the antibody or antigen-binding fragment thereof according to any one of items 1 to 18.
34. The method of item 33, wherein said detecting is by flow cytometry.
35. A method for diagnosing an inflammatory or autoimmune condition in a first subject, said method comprising (a) determining the level of DICAM expression, DICAM activity and/or DICAM-expressing cells in an inflamed tissue sample from said first subject using the antibody or antigen-binding fragment thereof according to any one of items 1 to 18, or the composition of item 19 or 20; (b) comparing said level to a corresponding reference level; and (c) diagnosing the inflammatory or autoimmune condition based on said comparison.
36. The method of item 35, wherein (i) said reference level corresponds to a level determined in a sample from a control subject known to not having an inflammatory condition, and wherein a higher level in said inflamed tissue sample from said first subject is indicative that said first subject has an inflammatory condition; or (ii) said reference level corresponds to a level determined in a sample from a control subject known to have an inflammatory condition, and wherein a comparable or higher level in said inflamed tissue sample from said first subject is indicative that said first subject has an inflammatory condition.
37. The method of item 35 or 36, wherein said inflammatory condition is a neuroinflammatory condition.
38. The method of item 37, wherein said sample is a central nervous system (CNS)-derived sample.
39. Use of the antibody or antigen-binding fragment thereof according to any one of items 1 to 18, or the composition of item 19 or 20, for diagnosing an inflammatory or autoimmune condition in a subject.
40. A method of identifying and/or purifying an inflammatory cytokine-secreting T cell or precursor thereof in a sample, said method comprising (i) contacting said sample with the antibody or antigen-binding fragment thereof according to any one of items 1 to 18, or the composition of item 19 or 20, and (ii) identifying and/or purifying said inflammatory cytokine-secreting T cell or precursor thereof based on the binding to said antibody or antigen-binding fragment thereof.
41. The method of item 39 or 40, wherein said antibody or antigen-binding fragment thereof is bound to a solid support.
42. The method of item 41, wherein said identifying and/or purifying is performed by flow cytometry.
43. The method of any one of items 40 to 42, wherein said inflammatory cytokine-secreting T cell or precursor thereof is an Interleukin-17-secreting T cell ($T_H17$ cell) or a precursor thereof.
44. The method of any one of items 40 to 43, wherein said inflammatory cytokine-secreting T cell or precursor thereof is a $CD4^+$ T cell.
45. Use of the antibody or antigen-binding fragment thereof according to any one of items 1 to 18, or the composition of item 19 or 20, for identifying an inflammatory cytokine-secreting T cell or precursor thereof in a sample, said method comprising (i) contacting said sample with and (ii) identifying and/or purifying said inflammatory cytokine-secreting T cell or precursor thereof based on the binding to said antibody or antigen-binding fragment thereof.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 3F: Protein expression of DICAM was confirmed by Western blot at Day 6. β-actin was used as loading control. Data shown are representative of 5 independent experiments. *, P<0.05, **, P<0.01

FIG. 5A: qPCR analysis of the expression of DICAM in ex vivo human CD4, $CD4^+$ $CD45RA^+$, $CD4^+CD45RO^+$, $CD8^+$, $CD19^+$ lymphocytes and $CD14^+$ monocytes. $CD83^+$ dendritic cells from healthy donors (N=5). CD83 cells were generated in vitro from CD14 monocytes cultivated with IL-4 (20 ng/ml) and GM-CSF (100 ng/ml) during 6 days.

FIGS. 6A and B show that $T_H17$ polarizing cytokines IL-1, TGF-β, IL-6 and IL-23 induce DICAM mRNA expression in human CD4 lymphocytes. QPCR analysis of DICAM (FIG. 6A) and IL-17 (FIG. 6B) mRNA in naïve $CD4^+$ CD45RA T lymphocytes cultivated with IL-1β, (25 ng/ml), IL-6 (25 ng/ml), TGF-β (25 ng/ml) and IL-23 (25 ng/ml) (alone or in combination) and with neutralizing antibodies against IL-4 and IFNγ.

FIG. 7 shows that DICAM mRNA expression is significantly increased in human $CD8^{30}$ and $CD4^+$ lymphocytes in Multiple Sclerosis (MS) patients. qPCR analysis of DICAM mRNA expression by ex vivo peripheral blood $CD4^+$ and $CD8^+$ T lymphocytes of healthy controls (HC; n=4) and untreated relapsing-remitting MS patients (RRMS; n=4) **, P<0.05.

FIG. 11A: Immunofluorescent staining and confocal microscopy analysis of active MS lesions showing expression of DICAM by $CD4^+$ T lymphocytes. Colocalization is seen with TO-PRO-3 as a nuclear stain. High power magnification images of infiltrating cells are shown in the right panels. Photomicrographs shown are representative of immunostainings performed on 4 active plaques obtained from CNS material of 2 MS patients. FIG. 11B: Immunofluorescent staining and confocal microscopy analysis of active MS lesions showing expression of DICAM by IL-17-producing cells. Colocalization is seen with TO-PRO-3 as a nuclear stain. High power magnification images of infiltrating cells are shown in the right panels. Photomicrographs shown are representative of immunostainings performed on 4 active plaques obtained from CNS material of 2 MS patients.

FIG. 18A: DICAM mRNA expression by NIH3T3 cells transfected by DICAM-encoding vector (NIH3T3 $DICAM^+$) and by empty vector (NIH3T3 empty). FIG. 18B: Western Blot analysis of the expression of DICAM, using 3 different supernatants of anti-DICAM hybridoma cells clones, 1D4, 3C2 and 9E9. FIG. 18C: Flow cytometry analysis of NIH3T3 empty (top panel) and $NIH3T3-DICAM^+$ (bottom panel) immunostained with anti-human DICAM monoclonal antibodies (clones 1B2 and 9E9) or with an isotype control antibody (n=4). FIG. 18D: Flow cytometry analysis of NSO cells expressing (right panel) or not (left panel) DICAM using a fluorescently-conjugated mAb clone 9E9. Murine myeloma NSO cells were transfected with a DICAM-encoding vector, using Lipofectamine™ LTX plus. Anti-DICAM (clone 9E9) was labeled with fluorescent dye CF647 (spectrally similar to Alexa Fluor® 647 using the Mix-n-Stain™ CF™ 647 Antibody Labeling kit from Sigma-Aldrich®, according to the manufacturer's instructions. FIG. 18E: detection of DICAM on $T_H17$ lymphocytes using the fluorescently-conjugated mAb clone 9E9. $T_H17$ lymphocytes were differentiated in vitro using memory $CD4^+CD45RO^+$ lymphocytes from healthy donors activated with anti-CD3/anti-CD28 antibodies in the presence of IL-23. After 6 days of culture, the expression of DICAM, IL-17, IFNγ and GM-CSF was determined by flow cytometry. For the detection of IL-17, IFNγ and GM-CSF, cells were stimulated for 5 hours with PMA/Ionomycin. N≥5.

FIGS. 19A and C: Analysis of fluorescence; and FIG. 19B: percentage of adherent $T_H17$ lymphocytes. DICAM blockade with clone 9E9 significantly inhibits the adhesion of $T_H17$ lymphocytes to αVβ3 integrin. Data shown are representative of 5 experiments performed in triplicate. *, P<0.05.

FIG. 20A shows the in vitro model used to assess the migration of immune cells across BBB-ECs. In this modified Boyden chamber assay, human BBB-ECs are grown on the mesh of a porous membrane. Immune cells are added to the upper chamber and allowed to migrate for 18 h. Immune cells that migrated to the bottom chamber are counted and phenotyped by flow cytometry. FIGS. 20B-E: $T_H17$ lymphocytes were allowed to migrate for 18 h across a monolayer of human BBB-ECs pre-treated with isotype control or anti-DICAM mAb Clone 9E9 (5 µg/ml or 20 µg/ml, FIG. 20B, C), anti-DICAM mAb subclones 9E9.1 and 9E9.2 (FIG. 20C), anti-DICAM mAb clone 3C2 (FIG. 20D) or anti-DICAM mAb clones 1B2, 2C11 or 2H12 (FIG. 20E). Data shown are representative of 5 independent experiments performed in triplicate using 2 distinct BBB-EC preparations. *, P<0.05, **, P<0.01.

FIGS. 21A and 21B show the nucleotide (SEQ ID NO:17) and amino acid (SEQ ID NO:18) sequences of human DICAM isoform 1 (UniProt identifier: Q9BRK3-1; NCBI Reference Sequences: NP_001269511.1, NM_001282582.1), which is considered the "canonical" sequence.

FIGS. 22A and 22B show the nucleotide (SEQ ID NO:19) and amino acid (SEQ ID NO:20) sequences of human DICAM isoform 2 (UniProt identifier: Q9BRK3-2; NCBI Reference Sequences: NP_001269514.1, NM_001282585.1).

FIGS. 23A and 23B show the nucleotide (SEQ ID NO:21) and amino acid (SEQ ID NO:22) sequences of human DICAM isoform 3 (UniProt identifier: Q9BRK3-3; NCBI Reference Sequences: NP_001269512.1, NM_001282583.1).

FIGS. 24A and 24B show the nucleotide (SEQ ID NO:23) and amino acid (SEQ ID NO:24) sequences of human DICAM isoform 4 (UniProt identifier: Q9BRK3-4; NCBI Reference Sequences: NP_001269513.1, NM_001282584.1).

FIG. 25A shows the nucleotide sequence of the light chain variable region of hybridoma clone 9E9 (SEQ ID NO:25). The beginning of the murine kappa chain constant region is underlined.

FIG. 25B shows the amino acid sequence of the light chain variable region of hybridoma clone 9E9 (SEQ ID NO:26). The beginning of the murine kappa chain constant region is underlined, and the putative signal/leader peptide sequence is in italics.

FIG. 25C shows the nucleotide sequence of the heavy chain variable region of hybridoma clone 9E9 (SEQ ID NO:27). The beginning of the murine IgG1 chain constant region is underlined.

FIG. 25D shows the amino acid sequence of the heavy chain variable region of hybridoma clone 9E9 (SEQ ID NO:28). The beginning of the murine IgG1 chain constant region is underlined, and the putative signal/leader peptide sequence is in italics.

FIG. 26A shows the numbering and regions of the light chain variable region of hybridoma clone 9E9 (residues 23 to 129 of SEQ ID NO:26) according to different commonly used nomenclatures. The antibody discovery system abYsis was used to identify the regions.

FIG. 26B shows the numbering and regions of the heavy chain variable region of hybridoma clone 9E9 (residues 20 to 137 of SEQ ID NO:28) according to different commonly used nomenclatures. The antibody discovery system abYsis was used to identify the regions.

FIG. 27A shows the nucleotide sequence of the light chain variable region of hybridoma clone 3C2 (SEQ ID NO:29). The beginning of the murine kappa chain constant region is underlined.

FIG. 27B shows the amino acid sequence of the light chain variable region of hybridoma clone 3C2 (SEQ ID NO:30). The beginning of the murine kappa chain constant region is underlined, and the putative signal/leader peptide sequence is in italics.

FIG. 27C shows the nucleotide sequence of the heavy chain variable region of hybridoma clone 3C2 (SEQ ID NO:31). The beginning of the murine IgG2b chain constant region is underlined.

FIG. 27D shows the amino acid sequence of the heavy chain variable region of hybridoma clone 3C2 (SEQ ID NO:32). The beginning of the murine IgG2b chain constant region is underlined, and the putative signal/leader peptide sequence is in italics.

Figure 28A:
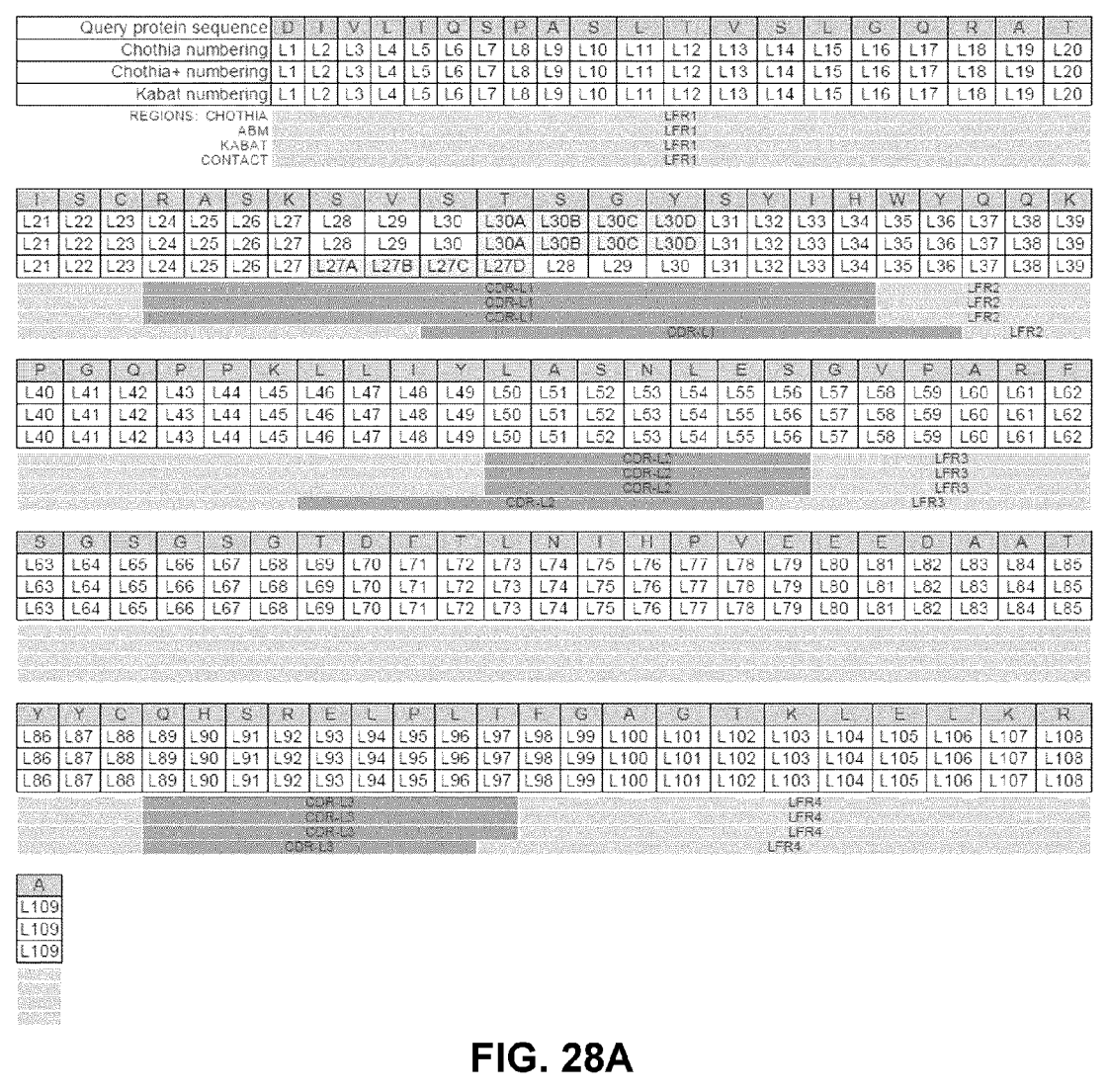
Figure 28B:
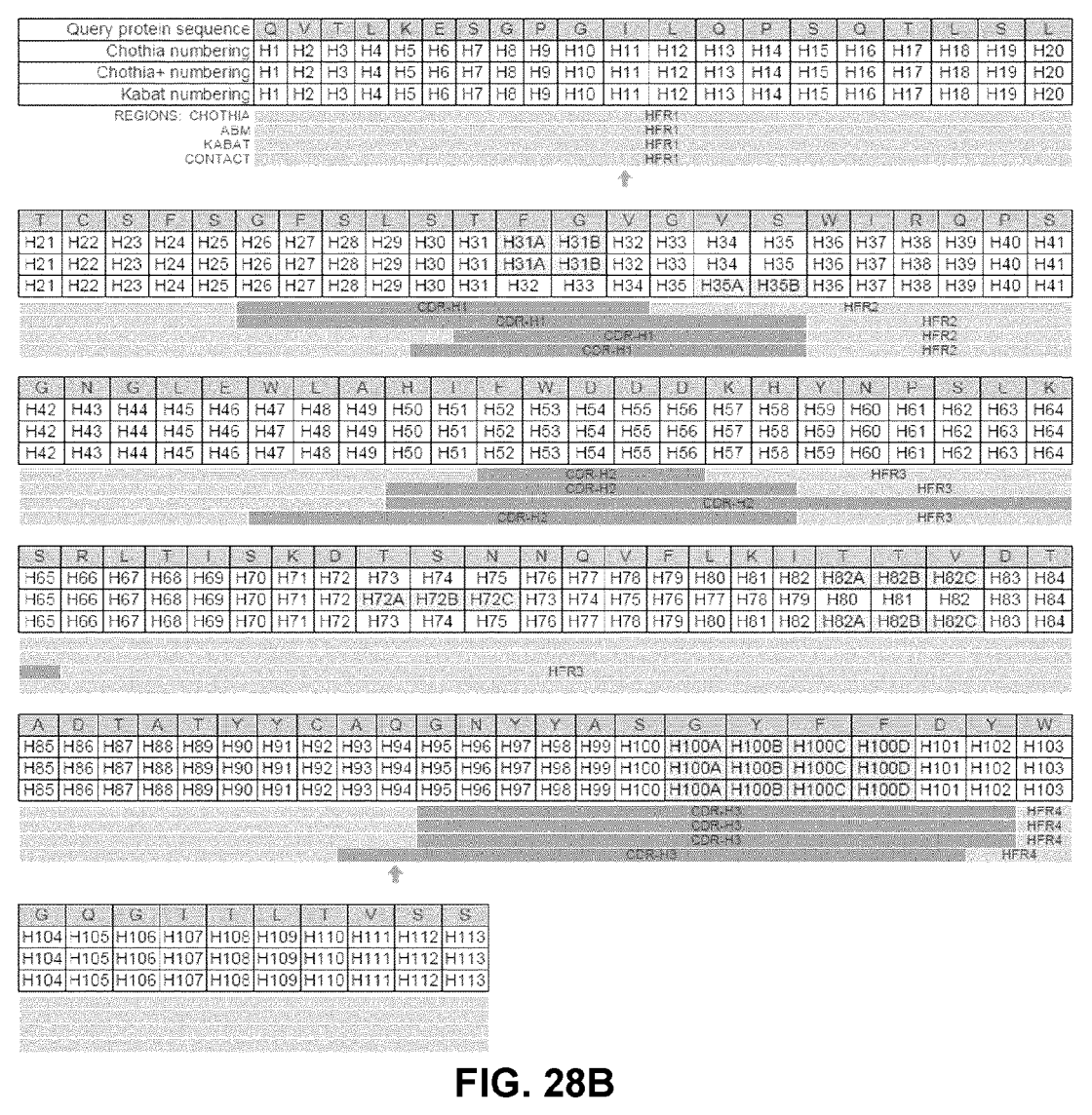

FIG. 28A shows the numbering and regions of the light chain variable region of hybridoma clone 3C2 (residues 21 to 133 of SEQ ID NO:30) according to different commonly used nomenclatures. The antibody discovery system abYsis was used to identify the regions.

FIG. 28B shows the numbering and regions of the heavy chain variable region of hybridoma clone 3C2 (residues 20 to 141 of SEQ ID NO:32) according to different commonly used nomenclatures. The antibody discovery system abYsis was used to identify the regions.

DESCRIPTION OF ILLUSTRATIVE EMBODIMENTS

Figure 1A:
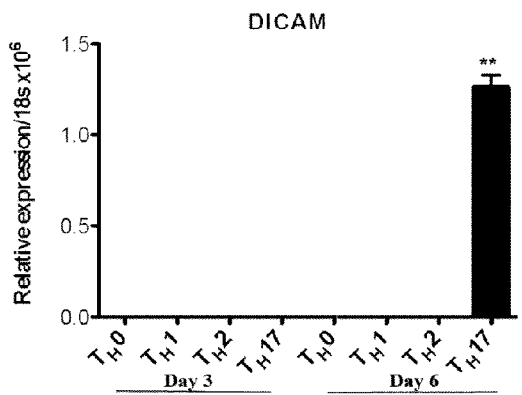
FIGS. 1A-F show the expression of various molecules by human memory lymphocytes $CD4^+CD45RO^+$ from healthy donors activated with anti-CD3/anti-CD28 antibodies cultured under $T_H0$ (no cytokine added), $T_H1$ (in the presence of IL-12), $T_H2$ (in the presence of IL-4) or $T_H17$ (in the presence of IL-23) polarizing conditions. After 3 and 6 days of the culture, the expression of RNA messenger of DICAM (FIG. 1A), IL-17 (FIG. 1B) IFNγ (FIG. 1C), RORγ (FIG. 1D), Tbet (FIG. 1E) and MCAM (FIG. 1E), were determined by quantitative polymerase chain reaction (qPCR) at Day 3 and Day 6. **, P<0.05. n=4.
Figure 1B:
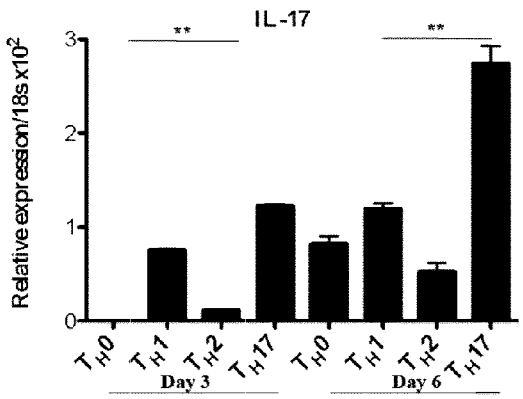
Figure 1C:
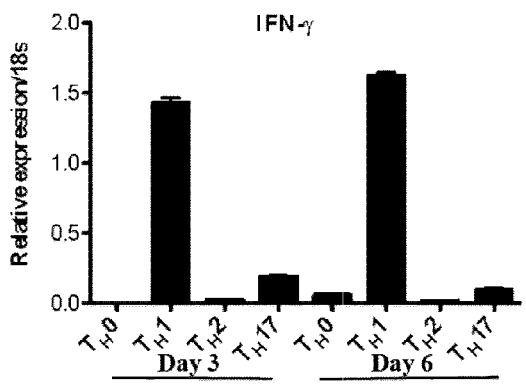
Figure 1D:
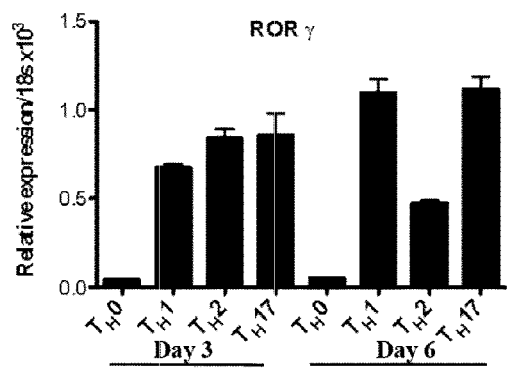
Figure 1E:
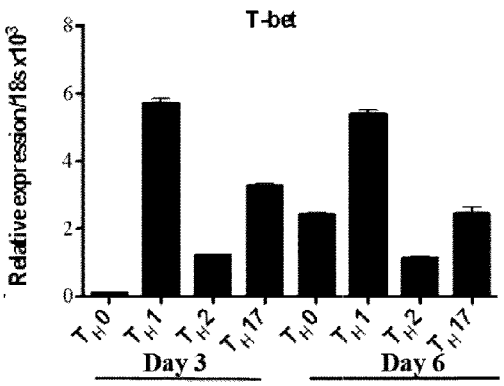
Figure 1F:
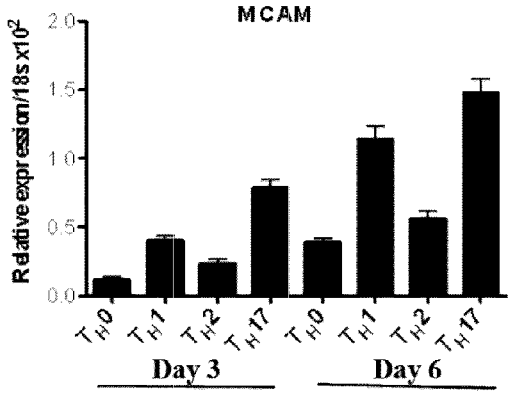

In the studies described herein, it is demonstrated that DICAM is expressed by both BBB-ECs and a subset of inflammatory IL-17-expressing CD4 T lymphocytes (T$_H$17), which are infiltrated in active MS lesions, and that its expression at the BBB is decreased in active MS lesions. The present inventors have identified and characterized anti-DICAM monoclonal antibodies suitable for flow cytometry applications, and/or which block the adhesion of T$_H$17 lymphocytes to αVβ3 integrin and/or their transmigration across the human BBB. It is further shown that administration of anti-DICAM mAb clone E9E described inhibits/reduces the migration/recruitment of inflammatory, IFNγ-producing T$_H$17 lymphocytes into the CNS of EAE mice, an animal model of neuroinflammatory conditions (e.g., multiple sclerosis), and reduces the severity of the disease.

Accordingly, in an aspect, the present invention relates to a binding reagent, e.g., an antibody or an antigen-binding fragment thereof, that specifically recognizes native DICAM, e.g., DICAM expressed at the surface of a cell (e.g., living cells). The term "binding reagent" as used herein refers to a molecule capable of binding to DICAM and having one or more of the features described herein. Examples of binding reagents include peptides (e.g., a peptide that blocks the binding of DICAM to its natural ligand, αVβ3 integrin) or polypeptides, such as antibody or an antigen-binding fragment thereof.

Accordingly, in an aspect, the present invention relates to a binding reagent, e.g., an antibody or an antigen-binding fragment thereof, that specifically recognizes native DICAM, e.g., DICAM expressed at the surface of a cell (e.g., living cells). In another aspect, the present invention relates to a binding reagent, e.g., an antibody or an antigen-binding fragment thereof, that is suitable to detect DICAM by flow cytometry. In another aspect, the present invention relates to a binding reagent, e.g., an antibody or an antigen-binding fragment thereof, that blocks the interaction between DICAM and αVβ3 integrin. In an embodiment, the binding reagent, e.g., an antibody or an antigen-binding fragment thereof, binds to an epitope located within a domain corresponding to residues 57-71 (PRMVWTQDRLHDRQR) or 372-385 (YSDQKSGKSKGKDV) of SEQ ID NO:18, which corresponds to isoform 1 of human Dual Ig domain containing cell adhesion molecule (DICAM). The term "epitope" as used herein refers to an antigenic determinant capable of specific binding to an antibody.

In another aspect, the present invention relates to a binding reagent, e.g., an antibody or an antigen-binding fragment thereof, that blocks the adhesion of inflammatory T lymphocytes (e.g., IL-17-secreting T lymphocytes such as T$_H$17 and/or T$_C$17 lymphocytes, for example IFNγ-producing T$_H$17 lymphocytes) to αVβ3 integrin and/or the transmigration of (e.g., IL-17-secreting T lymphocytes such as T$_H$17 and/or T$_C$17 lymphocytes) across the vascular epithelium, such as human BBB. In an embodiment, the antibody or antigen-binding fragment thereof binds to an epitope located within a domain corresponding to residues 57-71 or 372-385 of isoform 1 of human DICAM.

In another aspect, the present invention relates to a binding reagent, e.g., an antibody or an antigen-binding fragment thereof, that specifically binds to an epitope located within a domain corresponding to residues 57-71 or 372-385 of isoform 1 of DICAM. In an embodiment, the binding reagent, e.g., an antibody or an antigen-binding fragment thereof, specifically binds to an epitope located within a domain corresponding to residues 57-71 of isoform 1 of human DICAM. In another embodiment, the binding reagent, e.g., an antibody or an antigen-binding fragment thereof, specifically binds to an epitope located within a domain corresponding to residues 372-385 of isoform 1 of human DICAM.

In another aspect, the present invention relates to a binding reagent, e.g., an antibody or an antigen-binding fragment thereof, that exhibits the same antigenic specificity as (e.g., which competes for antigen binding with) mAb clones 9E9, 9E9.1, 9E9.2 and/or 3C2 disclosed herein. In another aspect, the present invention relates to an antibody or an antigen-binding fragment thereof that comprises the heavy chain and light chain complementarity-determining regions (CDRs), i.e. CDR1, CDR2 and CDR3 of mAb clones 9E9, 9E9.1, 9E9.2 or 3C2 disclosed herein. In an embodiment, the antibody or an antigen-binding fragment thereof comprises the heavy chain and light chain variable domains of mAb clones 9E9, 9E9.1, 9E9.2 or 3C2 disclosed herein. The amino acid sequences and CDR regions (identified according to different numbering schemes) of the light chain and heavy chain variable domains of mAb clones 9E9 are depicted in FIG. 26A (residues 23-129 of SEQ ID NO:26) and FIG. 26B (residues 20-137 of SEQ ID NO:28), respectively. The sequences and CDR regions (identified according to different numbering schemes) of the light chain and heavy chain variable domains of mAb clones 3C2 are depicted in FIG. 27A and FIG. 27B, respectively. The sequences of the CDR regions of mAb clones 9E9 and 3C2 are set forth in Table I and Table II below, respectively.

TABLE I

Sequences of the CDR regions of mAb clone 9E9

| Region | Numbering Scheme | Sequence | SEQ ID NO: |
|---|---|---|---|
| CDR-L1 | Kabat | SASSSVSYMH-- | 1 |
|  | Chothia | SASSSVSYMH-- | 1 |
|  | AbM | SASSSVSYMH-- | 1 |
|  | Contact | ------SYMHWY | 2 |
| CDR-L2 | Kabat | ----STSNLAS | 3 |
|  | Chothia | ----STSNLAS | 3 |
|  | AbM | ----STSNLAS | 3 |
|  | Contact | LLIYSTSNLAS | 4 |
| CDR-L3 | Kabat | HQWSSYRT | 5 |
|  | Chothia | HQWSSYRT | 5 |
|  | AbM | HQWSSYRT | 5 |
|  | Contact | HQWSSYR- | 6 |
| CDR-H1 | Kabat | -----SYAMS | 7 |
|  | Chothia | GFTFISY--- | 8 |
|  | AbM | GFTFISYAMS | 9 |
|  | Contact | ----ISYAMS | 10 |
| CDR_H2 | Kabat | ---TISSGGSYTYYPHSVKG | 11 |
|  | Chothia | ------SSGGSY-------- | 12 |
|  | AbM | ---TISSGGSYTY------ | 13 |
|  | Contact | WVATISSGGSYTY------ | 14 |
| CDR-H3 | Kabat | --LDGPSYAMDY | 15 |
|  | Chothia | --LDGPSYAMDY | 15 |
|  | AbM | --LDGPSYAMDY | 15 |
|  | Contact | ARLDGPSYAMD- | 16 |

TABLE II

Sequences of the CDR regions of mAb clone 3C2

| Region | Numbering Scheme | Sequence | SEQ ID NO: |
|---|---|---|---|
| CDR-L1 | Kabat | RASKSVSTSGYSYIH-- | 36 |
|  | Chothia | RASKSVSTSGYSYIH-- | 36 |
|  | AbM | RASKSVSTSGYSYIH-- | 36 |
|  | Contact | ------STSGYSYIHWY | 37 |
| CDR-L2 | Kabat | ----LASNLES | 38 |
|  | Chothia | ----LASNLES | 38 |
|  | AbM | ----LASNLES | 38 |
|  | Contact | LLIYLASNLE- | 39 |
| CDR-L3 | Kabat | QHSRELPLT | 40 |
|  | Chothia | QHSRELPLT | 40 |
|  | AbM | QHSRELPLT | 40 |
|  | Contact | QHSRELPL- | 41 |
| CDR-H1 | Kabat | -----TFGVGVS | 42 |
|  | Chothia | GFSLSTFGV--- | 43 |
|  | AbM | GFSLSTFGVS | 44 |
|  | Contact | ----STFGVGVS | 45 |
| CDR-H2 | Kabat | ---HIFWDDDKHYNPSLKS | 46 |
|  | Chothia | -----FWDDD--------- | 47 |
|  | AbM | ---HIFWDDDKH------ | 48 |
|  | Contact | WLAHIFWDDDKH------ | 49 |
| CDR-H3 | Kabat | --GNYYASGYFFDY | 50 |
|  | Chothia | --GNYYASGYFFDY | 50 |
|  | AbM | --GNYYASGYFFDY | 50 |
|  | Contact | AQGNWASGYFFDY | 51 |

CDR-L1=CDR1 region of the light chain variable domain
CDR-L2=CDR2 region of the light chain variable domain
CDR-L3=CDR3 region of the light chain variable domain
CDR-H1=CDR1 region of the heavy chain variable domain
CDR-H2=CDR2 region of the heavy chain variable domain
CDR-H3=CDR3 region of the heavy chain variable domain
Kabat=Kabat numbering scheme (Kabat E. A., Wu, T. T., Perry, H., Gottesman, K. and Foeller, C. (1991) *Sequences of Proteins of Immunological Interest*, Fifth Edition. NIH Publication No. 91-3242.
Chothia=Chothia numbering scheme (Al-Lazikani et al., Standard conformations for the canonical structures of immunoglobulins. *J. Mol. Biol.* 273, 927-948)
AbM=AbM numbering scheme (Martin, A. C. R., Cheetham, J. C. and Rees, A. R. (1989) *Proc. Natl Acad. Sci. USA*, 86,9268-9272).
Contact=Contact numbering scheme (MacCallum, R. M., Martin, A. C. R. and Thornton, J. T. Antibody-antigen interactions: Contact analysis and binding site topography. *J. Mol. Biol.* 262, 732-745)

In another aspect, the present invention provides an antibody or an antigen-binding fragment thereof comprising the sequences of the heavy chain and light chain complementarity-determining regions (CDRs) set forth in Table I or Table II, or an antibody or an antigen-binding fragment thereof competing for antigen binding with an antibody comprising the heavy chain and light chain CDRs set forth in Table I or Table II. In another aspect, the present invention provides an antibody or an antigen-binding fragment thereof comprising the sequences of the light chain and heavy chain variable domains depicted in FIG. 25B (residues 23-129 of SEQ ID NO:26) or FIG. 27B (residues 21-133 of SEQ ID NO:30) and FIG. 25D (residues 20-137 of SEQ ID NO:28) or FIG. 27D (residues 20-141 of SEQ ID NO:32), respectively, or an antibody or an antigen-binding fragment thereof competing for antigen binding with an antibody comprising the sequences of the light chain and heavy chain variable domains defined above. In another aspect, the present invention provides an antibody or an antigen-binding fragment thereof comprising the sequences of the heavy chain and light chain complementarity-determining regions (CDRs) set forth in Table I or Table II, wherein one or two residues within one or more of said CDRs are mutated.

DICAM (also known as also known as limitrin or Matrix-remodeling-associated protein 8, MXRA8), is a member of the immunoglobulin superfamily that comprises two V-type Ig domains in the extracellular region and a short cytoplasmic tail. DICAM is ubiquitously expressed in various organs and cells, including ECs and astrocytes. Functional blocking assays demonstrated that DICAM exerts cell adhesion activity in part through homotypic binding (DICAM-DICAM), or through heterotypic binding with the β3 subunit of the heterodimer αVβ3 integrin (Jung Y K, et al., *J Cell Physiol.* 2008; 216(3): 603-14).

The nucleotide and amino acid sequences of isoform 1 of human DICAM, which are considered the "canonical" sequences, are shown in FIGS. 21A and 21B. The nucleotide and amino acid sequences of the other isoforms of human DICAM are depicted in FIGS. 22A-B (isoform 2), FIGS. 23A-B (isoform 3) and FIGS. 24A-B (isoform 4).

The term "antibody or antigen-binding fragment thereof" as used herein refers to any type of antibody/antibody fragment including monoclonal antibodies (including full-length monoclonal antibodies), polyclonal antibodies, multispecific antibodies, humanized antibodies, CDR-grafted antibodies, chimeric antibodies and antibody fragments so long as they exhibit the desired antigenic specificity/binding activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies.

The term "monoclonal antibody" as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5): 1073-1093 (2004); Fellouse, Proc. Nat. Acad. Sci. USA 101(34): 12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO96/34096, WO96/33735, and WO91/10741, Jakobovits et al., Proc. Natl. Acad. Sci. USA, 90:2551 (1993); Jakobovits et al., Nature, 362:255-258 (1993); Bruggemann et al., Year in Immune, 7:33 (1993); U.S. Pat. Nos. 5,545,806, 5,569,825, 5,591,669 (all of GenPharm); U.S. Pat. No. 5,545,807; WO 97/17852, U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995). Antibodies capable of specifically binding to DICAM can also be produced using phage display technology. Antibody fragments that selectively bind to DICAM can then be isolated. Exemplary methods for producing such antibodies via phage display are disclosed, for example, in U.S. Pat. No. 6,225, 447.

The monoclonal antibodies herein specifically include "chimeric" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g., Old World Monkey, Ape, etc.) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region (e.g., a complementary-determining region, CDR) of the recipient are replaced by residues from a hypervariable region of a non-human species (donor antibody) such as mouse, rat, rabbit or nonhuman primate having the desired specificity, affinity, and capacity, such as the CDRs defined herein (Table I or Table II). In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Human chimeric antibody and human CDR-grafted antibody may be prepared using methods known in the art. A representative method is described below.

(1) Construction of Vector for Recombinant Antibody Expression. A vector for recombinant antibody expression is an expression vector for animal cell into which DNAs encoding $C_H$ and $C_L$ of a human antibody have been inserted, and is constructed by cloning each of DNAs encoding $C_H$ and $C_L$ of a human antibody into an expression vector for animal cell. The constant region (hereinafter, referred to as C region) of a human antibody may be $C_H$ and $C_L$ of any human antibody. Examples include $C_H$ of γ1 subclass and $C_L$ of κ class of human antibody, or the like. As the DNAs encoding $C_H$ and $C_L$ of a human antibody, the cDNA may be generally used and a chromosomal DNA composed of an exon and an intron can be also used. As the expression vector for animal cell, any expression vector can be used, as long as a gene encoding the C region of a human antibody can be inserted thereinto and expressed therein. Examples thereof include pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] or the like. Examples of a promoter and an enhancer used for an expression vector for animal cell include an SV40 early promoter [J. Biochem., 101, 1307 (1987)], a Moloney mouse leukemia virus LTR [Biochem. Biophys. Res. Commun., 149, 960 (1987)], an immunoglobulin H chain promoter [Cell, 41, 479 (1985)], an enhancer [Cell, 33, 717 (1983)] or the like. As the vector for recombinant antibody expression, a type of the vector for recombinant antibody expression in which both of antibody H and L chains exist on the same vector (tandem type) (J. Immunol. Methods, 167, 271 (1994)) may be used, in terms of easiness of construction of a vector for recombinant antibody expression, easiness of introduction into animal cells, and balance between the expression levels of antibody H and L chains in animal cells, and a type in which antibody H and L chains exist on separate vectors may be also used. Examples of the tandem type of the vector for recombinant antibody expression include pKANTEX93 (WO 97/10354), pEE18 (Hybridoma, 17, 559 (1998)), or the like.

(2) Acquisition of cDNA Encoding V Region of Antibody Derived from Non-Human Animal and Analysis of Amino Acid Sequence. mRNA is extracted from hybridoma cells producing a non-human antibody to synthesize cDNA. The synthesized cDNA is cloned into a vector such as a phage or a plasmid, to prepare a cDNA library. Each of a recombinant phage or recombinant plasmid containing cDNA encoding $V_H$ or $V_L$ is isolated from the library using DNA encoding the C region or V region of a mouse antibody as the probe. The full length of the base sequences of $V_H$ and $V_L$ of a mouse antibody of interest on the recombinant phage or recombinant plasmid are determined, and the full length of the amino acid sequences of $V_H$ and $V_L$ are deduced from the base sequences, respectively. Examples of the non-human animal for preparing a hybridoma cell which produces a non-human antibody include mouse, rat, hamster, rabbit or the like. Any animals can be used as long as a hybridoma cell can be produced therefrom. Total RNA can be prepared from a hybridoma cell using a guanidine thiocyanate-cesium trifluoroacetate method (Methods in Enzymol., 154, 3 (1987)), or a kit such as RNA easy kit (manufactured by Qiagen®) or the like. mRNA can be prepared from total RNA using an oligo (dT) immobilized cellulose column method (Molecular Cloning, A Laboratory Manual, Second Edition, Cold Spring Harbor Laboratory Press (1989)), a method using a kit such as Oligotex™-dT30 <Super> mRNA Purification Kit (manufactured by Takara Bio) or the like. In addition, mRNA can be prepared from hybridoma cells using a kit such as a Fast Track® mRNA Isolation kit (manufactured by Invitrogen®), a QuickPrep® mRNA Purification Kit (manufactured by Pharmacia®) or the like. Examples of the method for synthesizing cDNA and preparing a cDNA library include known methods (Molecular Cloning, A Laboratory Manual, Second Edition, Cold Spring Harbor Laboratory Press (1989), Current Protocols in Molecular Biology, Supplement 1, John Wiley & Sons (1987-1997)), a method using a kit such as a Super Script® Plasmid System for cDNA Synthesis and Plasmid Cloning (manufactured by Invitrogen®), a ZAP-cDNA Synthesis Kit (manufactured by Stratagene®), or the like. The vector for preparing a cDNA library, into which cDNA synthesized using mRNA extracted from a hybridoma cell as the template is inserted, may be any vector, as long as the cDNA can be inserted thereto. Examples thereof include ZAP ExPress (Strategies, 5, 58 (1992)), pBluescript II SK(+) [Nucleic Acids Research, 17, 9494 (1989)], AZAPII (manufactured by Stratagene®), λgt10 and λgt11 (DNA Cloning: A Practical Approach, I, 49 (1985)), Lambda BlueMid (manufactured by Clontech®), λExCell, pT7T3-18U (manufactured by Pharmacia®), pcD2 (Mol. Cell. Biol., 3, 280 (1983)), pUC18 (Gene, 33, 103 (1985)), or the like. Any *Escherichia coli* for introducing the cDNA library constructed by a phage or plasmid vector may be used, as long as the cDNA library can be introduced, expressed and maintained. Examples thereof include XL1-Blue MRF (Strategies, 5, 81 (1992)), C600 (Genetics, 39, 440 (1954)), Y1088 and Y1090 (Science, 222: 778 (1983)), NM522 (J. Mol. Biol., 166, 1 (1983)), K802 (J. Mol. Biol., 16, 118 (1966)), JM105 (Gene, 38, 275 (1985)), or the like. A colony hybridization or plaque hybridization method using an isotope- or fluorescence-labeled probe (Molecular Cloning, A Laboratory Manual, Second Edition, Cold Spring Harbor Laboratory Press (1989)) may be used for selecting cDNA clones encoding $V_H$ or $V_L$ of a non-human antibody or the like from the cDNA library. Also, the cDNA encoding $V_H$ or $V_L$ can be prepared through polymerase chain reaction by preparing primers and using cDNA prepared from mRNA or a cDNA library as the template. The base sequence of the cDNA can be determined by digesting the cDNA selected with appropriate restriction enzymes or the like, cloning the fragments into a plasmid such as pBluescript SK(−), carrying out a sequence analyzing method usually used. For example, the sequence analyzing method is carried out by using an automatic nucleotide sequence analyzer such as ABI PRISM3700® (manufactured by PE Biosystems®) or A.L.F. DNA sequencer (manufactured by Pharmacia®) after reaction such as the dideoxy method (Proc. Natl. Acad. Sci. USA, 74, 5463 (1977)). Whether the obtained cDNAs encode the full amino acid sequences of $V_H$ and $V_L$ of the antibody containing a secretory signal sequence can be confirmed by estimating the full length of the amino acid sequences of $V_H$ and $V_L$ from the determined nucleotide sequence and comparing them with the full length of the amino acid sequences of $V_H$ and $V_L$ of known antibodies (A.L.F. DNA sequencer, US Dept. Health and Human Services (1991)), and furthermore the subgroup to which they belong can be determined. In addition, the amino acid sequence of each CDR of $V_H$ and $V_L$ can be determined by comparing them with the amino acid sequences of $V_H$ and $V_L$ of known antibodies.

(3) Construction of Vector for Human Chimeric Antibody Expression. cDNA encoding each of $V_H$ and $V_L$ of antibody of non-human animal is cloned in the upstream of genes encoding $C_H$ or $C_L$ of human antibody of vector for expression of recombinant antibody mentioned above, thereby constructing a vector for human chimeric antibody expression. In order to ligate the 3'-terminus of cDNA encoding $V_H$ or $V_L$ of antibody of non-human animal and the 5'-terminus of $C_H$ or $C_L$ of human antibody, each cDNA encoding $V_H$ and $V_L$ is prepared so as to encodes appropriate amino acids encoded by a base sequence of a linkage portion and designed to have an appropriate recognition sequence of a restriction enzyme. The prepared cDNAs of $V_H$ and $V_L$ are respectively cloned so that each of them is expressed in an appropriate form in the upstream of gene encoding $C_H$ or $C_L$ of the human antibody of the vector for the human CDR-grafted antibody expression mentioned in the above (1) to construct a vector for human chimeric antibody expression. In addition, cDNA encoding $V_H$ or $V_L$ of a non-human animal antibody is amplified by PCR using a synthetic DNA having a recognition sequence of an appropriate restriction enzyme at both ends, and each of them is cloned to the vector obtained in the above (1) for recombinant antibody expression.

(4) Construction of cDNA Encoding V Region of Human CDR-Grafted Antibody. Amino acid sequences of FR in $V_H$ or $V_L$ of a human antibody to which amino acid sequences of CDRs in $V_H$ or $V_L$ of a non-human antibody (e.g., the CDRs of antibody clone E9E described herein) are grafted are selected, respectively. Any amino acid sequences of FR can be used, as long as they are derived from human. Examples thereof include amino acid sequences of FRs of human antibodies registered in database such as Protein Data Bank or the like, or amino acid sequences common to subgroups of FRs of human antibodies [A. L. F. DNA, US Dept. Health and Human Services (1991)] or the like. In order to inhibit the decrease in the binding activity of the antibody, amino acid sequences of FR having high homology (at least 60% or more) with the amino acid sequence of FR in $V_H$ or $V_L$ of the original antibody is selected. Then, amino acid sequences of CDRs of the original antibody are grafted to the selected amino acid sequence of FR in $V_H$ or $V_L$ of the human antibody, respectively, to design each amino acid sequence of $V_H$ or $V_L$ of a human CDR-grafted antibody. The designed amino acid sequences are converted to DNA sequences by considering the frequency of codon usage found in nucleotide sequences of genes of antibodies, and the DNA sequence encoding the amino acid sequence of $V_H$ or $V_L$ of a human CDR-grafted antibody is designed. Based on the designed DNA sequences, several synthetic DNAs having a length of about 100 nucleotides are synthesized, and PCR is carried out using them. In this case, it is preferred that 6 synthetic DNAs per each of the H chain and the L chain are designed in view of the reaction efficiency of PCR and the lengths of DNAs which can be synthesized. Furthermore, the cDNA encoding $V_H$ or $V_L$ of a human CDR-grafted antibody can be easily cloned into the vector for expressing the human CDR-grafted antibody constructed in (1) by introducing the recognition sequence of an appropriate restriction enzyme to the 5' terminal of the synthetic DNAs existing on the both ends. Otherwise, it can be carried out using a synthetic DNA as a single DNA encoding each of the full-length H chain and the full-length L chain based on the designed DNA sequence. After PCR, an amplified product is cloned into a plasmid such as pBluescript SK (−) or the like, and the base sequence is determined according to a method similar to the method described in (2) to obtain a plasmid having a DNA sequence encoding the amino acid sequence of $V_H$ or $V_L$ of a desired human CDR-grafted antibody.

(5) Modification of Amino Acid Sequence of V Region of Human CDR-Grafted Antibody. It is known that when a human CDR-grafted antibody is produced by grafting only CDRs in $V_H$ and $V_L$ of a non-human antibody into FRs of $V_H$ and $V_L$ of a human antibody, its antigen binding activity is sometimes lower than that of the original non-human antibody [BIO/TECHNOLOGY, 9, 266 (1991)]. In human CDR-grafted antibodies, among the amino acid sequences of FRs in $V_H$ and $V_L$ of a human antibody, amino acid residues that are directly involved in the binding to an antigen, amino acid residues that interacts with an amino acid residue in CDR, and amino acid residues that maintain the three-dimensional structure of an antibody and indirectly involved in the binding to an antigen may be identified and replaced with amino acid residues which are found in the original non-human antibody, thereby increasing the antigen binding activity which has been decreased. In order to identify the amino acid residues involved in the antigen binding activity in FR, three-dimensional structure of an antibody can be constructed and analyzed by X-ray crystallography, computer-modeling or the like. In addition, modified human CDR-grafted antibody having sufficient binding activity against antigen can be obtained by producing several modified antibodies of each antibody and examining their antigen binding activities to identify those having improved affinity. The modification of the amino acid sequence of FR in $V_H$ and $V_L$ of a human antibody can be accomplished using various synthetic DNA for modification according to PCR as described in (4). With regard to the amplified product obtained by PCR, the base sequence is determined according to the method as described in (2) so as to examine whether the desired modification has been carried out.

(6) Construction of Vector for Human CDR-Grafted Antibody Expression. A vector for human CDR-grafted antibody expression can be constructed by cloning each cDNA encoding $V_H$ or $V_L$ of a constructed recombinant antibody into upstream of each gene encoding $C_H$ or $C_L$ of the human antibody in the vector for recombinant antibody expression as described in (1). For example, recognizing sequences of an appropriate restriction enzymes are introduced to the 5'-terminal of synthetic DNAs positioned at both ends among synthetic DNAs used in the construction of $V_H$ or $V_L$ of the human CDR-grafted antibody in (4) and (5), and cloning can be carried out so that they are expressed in an appropriate form in the upstream of each gene encoding $C_H$ or $C_L$ of the human antibody in the vector for a human CDR-grafted antibody expression as described in (1).

(7) Transient Expression of Recombinant Antibody. The recombinant antibodies can be expressed transiently using the vector for recombinant antibody expression obtained in (3) and (6) or the modified expression vector thereof so as to efficiently evaluate the antigen binding activity of various human CDR-grafted antibodies. Any cell can be used as a host cell, as long as the host cell is able to express a recombinant antibody. For example, COS-7 cell (ATCC CRL1651) is used. Introduction of the expression vector into COS-7 cell is performed by using a DEAE-dextran method, a lipofection method, or the like. After introduction of the expression vector, the expression level and antigen binding activity of the recombinant antibody in the culture supernatant can be determined by the enzyme immunoassay or the like.

(8) Acquisition of Transformant which Stably Expresses Recombinant Antibody and Preparation of Recombinant Antibody. A transformant which stably expresses a recombinant antibody can be obtained by introducing the vector for recombinant antibody expression obtained in (3) and (6) into an appropriate host cell. Introduction of the expression vector into a host cell is performed by electroporation or the like. As the host cell into which a vector for recombinant antibody expression is introduced, any cell can be used, as long as it is a host cell which is able to produce the recombinant antibody. Examples thereof include CHO-K1 (ATCC CCL-61), DUkXB11 (ATCC CCL-9096), Pro-5 (ATCC CCL-1781), CHO-S (Life Technologies®, Cat #11619), rat myeloma cell YB2/3HL.P2.G11.16Ag.20 (also called YB2/0), mouse myeloma cell NSO, mouse myeloma cell SP2/0-Ag14 (ATCC No. CRL1581), mouse P3-X63-Ag8653 cell (ATCC No. CRL1580), CHO cell in which a dihydrofolate reductase gene is defective, lectin resistance-acquired Lec13, CHO cell in which α1,6-fucosyltransaferse gene is defective, rat YB2/3HL.P2.G11.16Ag.20 cell (ATCC No. CRL1662), or the like. After introduction of the expression vector, transformants which stably express a recombinant antibody are selected by culturing them in a medium for animal cell culture containing an agent such as G418 sulfate or the like. Examples of the medium for animal cell culture include RPM11640 medium (manufactured by Invitrogen®), GIT medium (manufactured by Nihon Pharmaceutical®), EX-CELL301® medium (manufactured by JRH®), IMDM medium (manufactured by Invitrogen®), Hybridoma-SFM medium (manufactured by Invitrogen®), media obtained by adding various additives such as FBS to these media, or the like. The recombinant antibody can be produced and accumulated in a culture supernatant by culturing the obtained transformants in a medium. The expression level and antigen binding activity of the recombinant antibody in the culture supernatant can be measured by ELISA or the like. Also, in the transformant, the expression level of the recombinant antibody can be increased by using DHFR amplification system or the like. The recombinant antibody can be purified from the culture supernatant of the transformant by using a protein A column. In addition, the recombinant antibody can be purified by combining the protein purification methods such as gel filtration, ion-exchange chromatography, ultrafiltration or the like. The molecular weight of the H chain or the L chain of the purified recombinant antibody or the antibody molecule as a whole is determined by polyacrylamide gel electrophoresis, Western blotting, or the like.

An "antibody" (or any other binding molecule) that binds to the same epitope as a reference antibody (or any other binding molecule) refers to an antibody (or any other binding molecule) that blocks binding of the reference antibody (or any other binding molecule) to its antigen in a competition assay by at least 50% (in embodiments by at least 55%, 60%, 65%, 70%, 75%, 80%, 85%, 90% or 95%), and conversely, the reference antibody (or any other binding molecule) blocks binding of the antibody to its antigen in a competition assay by at least 50% (in embodiments by at least 55%, 60%, 65%, 70%, 75%, 80%, 85%, 90% or 95%).

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169: 147-155 (1995); Yelton et al. J. Immunol. 155: 1994-2004 (1995); Jackson et al., J. Immunol. 154(7):3310-9 (1995); and Hawkins et al, J. Mol. Biol. 226:889-896 (1992).

The "light chains" of antibodies from any vertebrate species can be assigned to one of two clearly distinct types, called κ and λ, based on the amino acid sequences of their constant domains. Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgGl, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs are involved in conferring the antigen-binding specificity to the antibody. However, even a single variable domain (or half of an Fv comprising only three CDRs specific for an antigen) has the ability to recognize and bind antigen, although at a lower affinity than the entire binding site.

"Hypervariable region" or "HVR" refers to the amino acid residues of an antibody that are responsible for antigen-binding. The hypervariable region generally comprises amino acid residues from a "complementarity determining region" or "CDR" (Kabat et al., Sequences of Proteins of Immunological Interest, 5$^{th}$ Ed. Public Health Service, National Institutes of Health, Bethesda, Md. (1991)) and/or those residues from a "hypervariable loop" (Chothia and Lesk, J. Mol. Biol. 196: 901-917 (1987)).

The term "complementarity determining regions" or "CDRs" when used herein refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

The term "epitope" is used to refer to binding sites for (monoclonal or polyclonal) antibodies on protein antigens. Typically, an epitope refers to a unit of structure conventionally bound by an immunoglobulin $V_H$-$V_L$ pair. Epitopes define the minimum binding site for an antibody, and thus represent the target of specificity of an antibody. Epitopes can be linear or conformational, and can be as small as three amino acids.

In addition to the anti-DICAM antibodies described herein, it is contemplated that variants of such antibodies can be prepared. Anti-DICAM antibody variants can be prepared by introducing appropriate nucleotide changes into the encoding DNA, and/or by synthesis of the desired antibody. Those skilled in the art will appreciate that amino acid changes may alter post-translational processes of the anti-DICAM antibody, such as changing the number or position of glycosylation sites.

Variations in the anti-DICAM antibodies described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody that results in a change in the amino acid sequence as compared with the native sequence antibody. Optionally the variation is by substitution of at least one amino acid with any other amino acid in one or more of the domains of the DICAM antagonist antibody. Guidance in determining which amino acid residue may be inserted, substituted or deleted without adversely affecting the desired activity may be found by comparing the sequence of the anti-DICAM antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. In embodiment, the variant exhibit at least 60%, preferably at least 65, 70, 75, 80, 90, 95, 96, 97, 98 or 99% sequence identity with the sequence of the anti-DICAM antibodies described herein, and maintain the ability to specifically bind to DICAM.

Covalent modifications of anti-DICAM antibodies are included within the scope of this invention. Covalent modifications include reacting targeted amino acid residues of an anti-DICAM antibody with an organic derivatizing agent that is capable of reacting with selected side chains or the N- or C-terminal residues of the anti-DICAM antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains (T.E. Creighton, Proteins: Structure and Molecular Properties, W.H. Freeman & Co., San Francisco, pp. 79-86 (1983)), acetylation of the N-terminal amine, and amidation of any C-terminal carboxyl group.

In one aspect, the DICAM antibodies of the present invention comprise one or more deamidation mutations in the amino acid sequence. The deamidation of amino acid residues is a common structural modification in recombinant polypeptides, which can lead to the formation of iso-aspartic acid resulting in decreased stability. Deamidation may be associated with glycine (G)-asparginine (N) sequences, including G-N and N-G sequences. In one embodiment, the antibody comprises a deamidation mutation. In another embodiment, the deamidation mutation is the substitution of an N amino acid residue or a G amino acid residue. In some embodiments, the substitution is N→S, N→A, or G→Q. In one embodiment, the deamidation mutation is located at Kabat residue N32 or G33.

Other types of covalent modification of the anti-DICAM antibody included within the scope of this invention include altering the native glycosylation pattern of the antibody or polypeptide (Beck et al., Curr. Pharm. Biotechnol. 9: 482-501, 2008; Walsh, Drug Discov. Today 15: 773-780, 2010), and linking the antibody to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670, 417; 4,791,192 or 4,179,337.

In an embodiment, the anti-DICAM antibody is labelled. The anti-DICAM antibody may be labeled with one or more labels such as a biotin label, a fluorescent label, an enzyme label, a coenzyme label, a chemiluminescent label, or a radioactive isotope label. In an embodiment, the anti-DICAM antibody is labelled with a detectable label, for example a fluorescent moiety (fluorophore). Useful detectable labels include fluorescent compounds (e.g., fluorescein isothiocyanate, Texas red, rhodamine, fluorescein, Alexa Fluor® dyes, and the like), radiolabels, enzymes (e.g., horseradish peroxidase, alkaline phosphatase and others commonly used in an protein detection assays), streptavidin/biotin, and colorimetric labels such as colloidal gold, colored glass or plastic beads (e.g., polystyrene, polypropylene, latex, etc.). Chemiluminescent compounds may also be used. Such labelled antibody may be useful, for example, for the detection of DICAM and/or DICAM-expressing cells in vivo or in vitro, e.g., by flow cytometry. The anti-DICAM antibody can also be conjugated to one or more therapeutic agents may also be used therapeutically to deliver a therapeutic agent (e.g., anti-inflammatory agent or any other agent useful for the treatment of the disease or condition) into an inflamed tissue. Any method known in the art for conjugating the antibody to the label (e.g., detectable moiety) may be employed, including those methods described by Hunter et al. (1962) Nature, 144:945; David et al. (1974) Biochemistry, 13: 1014; Pain et al. (1981) J. Immunol. Meth., 40:219; Nygren, J. Histochem. and Cytochem., 30:407 (1982), and Hermanson, Bioconjugate Techniques 1996, Academic Press, Inc., San Diego.

In an embodiment, the anti-DICAM antibody is a monoclonal antibody. In another embodiment, the anti-DICAM antibody is a recombinant antibody. In a further embodiment, the recombinant antibody is a human chimeric antibody or a humanized antibody.

In another aspect, the present invention provides an antibody or an antigen-binding fragment thereof having one or more of the features described herein, i.e. any combination/sub-combination of the features described herein.

In another aspect, the present invention provides a nucleic acid comprising a sequence encoding the variable region of the heavy chain of the above-mentioned recombinant antibody. In a further embodiment, the nucleic acid further comprises a sequence encoding the constant region of the heavy chain of the above-mentioned recombinant antibody. In another aspect, the present invention provides a nucleic acid comprising a sequence encoding the variable region of the light chain of the above-mentioned recombinant antibody. In a further embodiment, the nucleic acid further comprises a sequence encoding the constant region of the light chain of the above-mentioned recombinant antibody.

In another aspect, the present invention provides a vector comprising one or more of the nucleic acids defined above. In another aspect, the present invention provides a host cell comprising one or more of the nucleic acids or vector defined above.

In another aspect, the present invention provides a composition comprising the above-mentioned anti-DICAM antibody and a carrier or excipient, in a further embodiment a pharmaceutically acceptable carrier or excipient. Such compositions may be prepared in a manner well known in the pharmaceutical art. Supplementary active compounds can also be incorporated into the compositions. As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration (see Remington: The Science and Practice of Pharmacy by Alfonso R. Gennaro, 2003, 21$^{th}$ edition, Mack Publishing Company). Therapeutic formulations are prepared using standard methods known in the art by mixing the active ingredient having the desired degree of purity with optional physiologically acceptable carriers, excipients or stabilizers. Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone (PVP), amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate (Tween®), poloxamer (Pluronics®) or polyethylene glycol (PEG).

Formulations suitable for oral administration may include (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient (anti-DICAM antibody), carriers known in the art.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

For preparing pharmaceutical compositions from the compound(s)/composition(s) of the present invention, pharmaceutically acceptable carriers are either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired. The powders and tablets may typically contain from 5% or 10% to 70% of the active compound/composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution. In an embodiment, the anti-DICAM antibodies described herein are administered to a human subject, in accord with known methods, such as intravenous administration as a bolus or by continuous infusion over a period of time.

Aqueous solutions suitable for oral use are prepared by dissolving the anti-DICAM antibody in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

In an embodiment, the anti-DICAM antibody is formulated/administered such that it comes into contact with neural cells or neural tissue, such as central nervous system (CNS) cells or tissue. Such tissue includes brain and spinal cord (e.g., cervical, thoracic, or lumbar) tissue. As such, in embodiments, the anti-DICAM antibody can be administered to treat neural cells/tissue in vivo via direct intracranial injection or injection into the cerebrospinal fluid (e.g., intrathecal injection). Alternatively, the anti-DICAM antibody can be administered systemically (e.g. intravenously) and may come into contact with the affected neural tissue via lesions (where the blood-brain barrier is compromised), or, in a further embodiment, may be in a form capable of crossing the blood-brain barrier and entering the neural system (e.g., CNS). Further, in an embodiment, a composition of the invention may be formulated for such administration to neural cells/tissue.

Methods of Use

The present invention relates to the use of the anti-DICAM antibodies described herein as therapeutic agents for diseases/conditions (e.g., inflammatory/autoimmune diseases) involving the activity of DICAM-expressing cells, for example DICAM-expressing inflammatory T lymphocytes such as $T_H17$ cells and/or $T_C17$ cells, notably IFNγ-producing $T_H17$ lymphocytes.

IL-17-secreting cells such as $T_H17$ and/or $T_C17$ cells have been implicated in the pathogenesis of a number of autoimmune diseases, particularly those neuroinflammatory conditions involving CNS infiltration of T cells, such as multiple sclerosis and the animal model, experimental autoimmune encephalomyelitis (EAE). (Cua et al., Nature 421: 744-748 (2003); Ivonov et al., Cell 126: 1121-1133 (2006). The pathogenicity of $T_H17$ cells can be partially explained by their unique migration pattern as evidenced by their expression of chemokine receptors. See, e.g., Kim, Inflamm. Allergy Drug Targets 8: 221-228 (2009). It has been established that IL-17-producing cells are enriched within the CCR6$^+$ population of CD4$^+$ T cells, likely conferring a unique migration pattern throughout the vasculature. The implication has been made that the true pathogenic function of $T_H17$ cells lies in their specific recruitment and infiltration of tissue. Thus, blocking the recruitment and infiltration of DICAM-expressing $T_H17$ cells, notably IFNγ-producing $T_H17$ lymphocytes, to tissues, such as the CNS.

Studies have demonstrated the role of pathogenic $T_H17$ and/or $T_C17$ cells in the pathogenesis of inflammatory/autoimmune diseases such as rheumatoid arthritis (RA), psoriasis, type 1 diabetes (T1D) and neuroinflammatory diseases (multiple sclerosis, spinal cord injury, Alzheimer's disease, Parkinson's disease, amyotrophic lateral sclerosis) (Marwaha et al., *Front Immunol.* 2012 Jun. 4; 3:129; Zong et al., Mediators of Inflammation, Volume 2014 (2014), Article ID 786947; Zhang et al., PLoS ONE 8(10): e75786, 2013). Accordingly, the present invention relates to the use of the anti-DICAM antibodies described herein as therapeutic agents for rheumatoid arthritis (RA), psoriasis, type 1 diabetes (T1D) and neuroinflammatory diseases (e.g., multiple sclerosis, spinal cord injury, Alzheimer's disease, Parkinson's disease, amyotrophic lateral sclerosis). In an embodiment, the present invention relates to the use of the anti-DICAM antibodies described herein as therapeutic agents for the treatment of one or more of the conditions noted above.

"Inflammatory or autoimmune condition" as used herein refers to a condition associated with inflammation and/or a dysregulated immune response, and with infiltration/recruitment of immune cells (more particularly $T_H17$ cells such as IFN-y-secreting $T_H17$ lymphocytes) to the injured/inflamed site (e.g., tissue, organ). "Neuroinflammatory condition" as used herein refers to a condition associated with inflammation of the nervous system, in an embodiment the central nervous system (CNS), and which is associated with cell/tissue damage. It is typically characterized by, for example, increased glial activation, increased pro-inflammatory cytokine/chemokine levels (e.g., TNF-α, IFN-γ, IL-1β), increased blood-brain-barrier permeability, and/or increased immune cell (e.g., leukocyte, $T_H17$ cells) recruitment/invasion to the CNS. It refers for example to chronic neuroinflammation, such as an inflammation associated with chronic activation of cells of the immune system (i.e., autoimmune-associated neuroinflammation). Such chronic neuroinflammation is observed, for example, in multiple sclerosis and other diseases. It also refers to inflammation resulting from a neural injury, such as spinal cord injury.

In an embodiment, the above-mentioned neuroinflammatory condition is multiple sclerosis (MS) and clinically isolated syndromes suggestive of MS, in a further embodiment active MS (i.e., relapse).

In another aspect, the present invention provides a method (in vivo or in vitro) for inhibiting or blocking the interaction of DICAM expressed on T cells and αVβ3 integrin, said method comprising contacting/treating the T cells with an anti-DICAM antibody described herein, thereby inhibiting the interaction of DICAM with αVβ3 integrin. In another aspect, the present invention provides a method for inhibiting or preventing extravasation of DICAM-expressing T cells, for example IFN-γ-secreting $T_H17$ lymphocytes, into an inflamed tissue/organ, e.g., the central nervous system (CNS), comprising contacting/treating the T cells with an anti-DICAM antibody (as described herein), thereby inhibiting or preventing the extravasation of DICAM-expressing T cells into the inflamed tissue/organ, e.g., CNS. In one embodiment, the anti-DICAM antibody blocks the interaction of DICAM with αVβ3 integrin. In an embodiment, the αVβ3 integrin is expressed on the surface of a cell, in a further embodiment an endothelial cell (e.g., a cell of the vascular endothelium), for example an endothelial cell of the blood-brain barrier (BBB-EC). In another embodiment, the T cells are $T_H17$ cells, for example pathogenic IFNγ-secreting $T_H17$ lymphocytes. In one other embodiment, the treatment with an anti-DICAM antibody is performed in vivo. In yet another embodiment, the treatment is performed in a mammalian subject. In one embodiment, the mammalian subject is a human.

In another aspect, the invention provides a method for the delaying or slowing down of the progression of a disease/condition (e.g., inflammatory/autoimmune diseases) involving the activity of DICAM-expressing cells, for example DICAM-expressing $T_H17$ cells.

In another aspect, the present invention relates to the use of the anti-DICAM antibodies described herein as therapeutic agents for neuroinflammatory conditions, including neuroinflammatory conditions such as multiple sclerosis. In one embodiment, the method comprises administering to subject diagnosed with the condition or disease, an effective amount of an anti-DICAM antibody (as described herein). In another aspect, the invention provides a method for preventing indicia of a neuroinflammatory condition. In one embodiment, the method comprises administering an effective amount of an anti-DICAM antibody (as described herein) to a subject at risk of the condition or disease, wherein the anti-DICAM antibody is effective against the development of indicia of the condition or disease.

For the prevention, treatment or reduction in the severity of a given disease or condition, the appropriate dosage of the anti-DICAM antibodies will depend on the type of disease or condition to be treated, as defined above, the severity and course of the disease or condition, whether the anti-DICAM antibodies are administered for preventive or therapeutic purposes, previous therapy, the patient's clinical history and response to the anti-DICAM antibodies, and the discretion of the attending physician. The anti-DICAM antibodies are suitably administered to the patient at one time or over a series of treatments. Preferably, it is desirable to determine the dose-response curve in vitro, and then in useful animal models prior to testing in humans. The present invention provides dosages for the anti-DICAM antibodies and compositions comprising same. For example, depending on the type and severity of the disease, about 1 μg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

An "effective amount" refers to an amount effective, at dosages and for periods of time necessary, to achieve the desired prophylactic or therapeutic result. An effective amount refers to the amount of active compound or pharmaceutical agent that elicits the biological or medicinal response in a tissue, system, animal, individual or human that is being sought by a researcher, veterinarian, medical doctor or other clinician, which includes one or more of the following:

(A) Preventing the disease; for example, preventing an inflammatory disease, such as a neuroinflammatory disease, condition or disorder in an individual that may be predisposed to the disease, condition or disorder but does not yet experience or display the pathology or symptomatology of the disease, (B) Inhibiting the disease; for example, inhibiting an inflammatory disease, such as a neuroinflammatory disease, condition or disorder in an individual that is experiencing or displaying the pathology or symptomatology of the disease, condition or disorder (i.e., arresting further development of the pathology and/or symptomatology), and (C) Ameliorating the disease; for example, ameliorating an inflammatory disease, such as a neuroinflammatory disease, condition or disorder in an individual that is experiencing or displaying the pathology or symptomatology of the disease, condition or disorder (i.e., reversing the pathology and/or symptomatology).

The efficacy of the treatment of neuroinflammatory conditions using the anti-DICAM antibodies described herein can be measured by various assessments commonly used in evaluating neuroinflammatory condition. For example, CNS health can be evaluated by testing for MS symptoms including, but not limited to, impaired vision (e.g., blurred or double vision, red-green color distortion, or blindness); muscle weakness in the extremities; impaired coordination and balance; partial or complete paralysis, paresthesias, transitory abnormal sensory feelings (e.g., numbness, prickling, or "pins and needles" sensations); pain; speech impediments; tremors; dizziness; hearing loss; cognitive impairments (e.g., difficulties with concentration, attention, memory, and poor judgment); and depression. MS testing may also include a lumbar puncture (spinal tap) for cerebrospinal fluid (CSF) tests (e.g., CSF oligoclonal banding suggesting inflammation of the CNS); a magnetic resonance imaging (MRI) scan of the head or spine; and a nerve function test (e.g., evoked potential test).

In an embodiment, the above-mentioned treatment comprises the use/administration of more than one (i.e. a combination of) active/therapeutic agent, one of which being the above-mentioned anti-DICAM antibody. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) is used/administered in combination with one or more agent(s) currently used to prevent or treat the disorder in question (e.g., an inflammatory disease, such as a neuroinflammatory disease, such as MS). For instance, an anti-DICAM antibody of the invention may be co-administered with at least one of the following disease-modifying agents: teriflunomide, interferon beta-1a, interferon beta-1b, glatiramer acetate, fingolimod, and mitoxantrone. In another embodiment, an additional therapeutic agent is an agent which treats an acute exacerbation of a disease. In one embodiment, the additional therapeutic agent for acute exacerbation is one or more corticosteroids. In one other embodiment, the one or more corticosteroids is prednisone, methylprednisolone, and/or dexamethasone. In another embodiment, the disease is multiple sclerosis and the acute exacerbation is a relapse or attack (e.g., inflammation of the CNS).

The composition may also contain more than one active compound for the particular indication being treated, preferably those with complementary activities that do not adversely affect each other. It may be desirable to use the above-mentioned anti-DICAM antibody or composition in addition to one or more agents used to prevent or treat the disorder in question. The above-mentioned anti-DICAM antibody may be formulated in a single composition or in several individual compositions which may be co-administered in the course of the treatment.

In another aspect, the present invention relates to a method for detecting DICAM and/or DICAM-expressing cells in a sample, said method comprising contacting the sample with the anti-DICAM antibody described herein. In an embodiment, the anti-DICAM antibody is labelled (with a detectable label such as a fluorescent tag). In an embodiment, the method further comprises contacting the sample with a labelled secondary antibody capable of detecting the anti-DICAM antibody. In an embodiment, the above-mentioned method is flow cytometry, and it further comprises analyzing the sample contacted with the anti-DICAM antibody (and optionally the secondary antibody) using a flow cytometry device to detect DICAM and/or DICAM-expressing cells in a sample.

Articles of Manufacture and Kits

The invention further provides a kit or package comprising the above-mentioned DICAM antibody or the above-mentioned composition, together with instructions for (i) the prevention and/or treatment of an inflammatory or autoimmune condition (e.g., a neuroinflammatory condition) in a subject. The kit may further comprise, for example, containers, buffers, a device (e.g., syringe) for administering the DICAM antibody or a composition comprising same. The instructions included with the kit generally include information as to dosage, dosing schedule, and route of administration for the treatment of the target disorder, such as a neuroinflammatory condition or an autoimmune disease. The containers of DICAM antibody may be unit doses, bulk packages (e.g., multi-dose packages), or subunit doses.

Also provided is an article of manufacture for therapeutic use, comprising a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-DICAM antibody of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another aspect, the invention further provides a kit or package comprising the above-mentioned anti-DICAM antibody, and instructions for detecting DICAM and/or DICAM-expressing cells in sample (by flow cytometry or other assays such as immunocytochemistry, immunohistochemistry, ELISA, Western blot, etc.). The kit may comprise a labelled anti-DICAM antibody, or a labelled secondary antibody capable of detecting the anti-DICAM antibody. The kit may further comprise appropriate buffers, control samples, containers, etc.

The present invention is illustrated in further details by the following non-limiting examples.

EXAMPLE 1

Materials and Methods

Patients and sample collection. All MS patients were observed at the CHUM-Notre-Dame Hosptial MS clinic and diagnosed according to the McDonald criteria. Human peripheral blood (PB) was collected from MS patients and from healthy donors. PB mononuclear cells were obtained from heparinized whole blood using Ficoll™ density gradient separation (Amersham Biosciences®, Baie D'Urfé, Quebec, Canada)

BBB-endothelial cell isolation and culture. BBB-endothelial cells were isolated from non-epileptic material according to a previously published protocol ((Prat et al., *J Neuropathol Exp Neurol.* 2000 59(10):896-906; Biernacki et al., *J Neuropathol Exp Neurol.* 2001 60(12): 1127-36; Prat et al., *Arch Neurol.* 2002 59(3): 391-7; Kebir et al. *Nat Med.* 2007 13(10):1173-5. Epub 2007 Sep. 9; Cayrol et al. *Nat Immunol.* 2008 9(2):137-45. Epub 2007 Dec. 23; Ifergan et al. *Brain.* 2008 131(Pt 3): 785-99. Epub 2007 Dec. 20). BBB-endothelial cells were grown in primary cultures in media composed of Medium 199 (Gibco® Invitrogen, Burlington, ON, Canada) supplemented with 20% clone M3 conditioned media, 10% fetal bovine serum (FBS), 5% normal human serum (HS), 0.2% endothelial cell growth supplement (EGGS) (5 µg/ml) and 0.13% insulin-selenium-transferrin premix on 0.5% gelatin-coated tissue culture plastic plates (all reagents from Sigma, Oakville, ON, Canada). For treatments, the BBB-endothelial cells were grown in culture media in the presence of 40% astrocyte conditioned media (ACM), until they reach confluency. When indicated BBB-endothelial cells were activated for 16 hours with 100 U/ml of Tumor Necrosis Factor (TNF) and 100 U/ml of Interferon (IFN)-γ (Biosource-Invitrogen, Carlsbad, Calif., USA) in the presence of 40% ACM and the absence of ECGS. As previously demonstrated, these cells express factor VIII, von Willebrand factor, Ulex Agglutenens Europaensis-1-binding sites, endothelial antigen HT-7; and are susceptible to tumor necrosis factor (TNF)-induced CD54 and CD106 up-regulation. Immunoreactivity for glial fibrillary acidic protein and α-myosin could not be detected, confirming the absence of contaminating astrocytes and smooth muscle cells, respectively. The absence of monocytes and macrophages was confirmed by immunostaining with anti-CD14 and anti-CD11c antibodies.

EAE mice. Experimental autoimmune encephalomyelitis (EAE) was induced by active immunization of female purchased from Charles River Laboratories® (Montréal, Qc, Canada) and Jackson Laboratory® (Bar Habor, Me., USA). 6 to 8 week old mice were injected subcutaneously with 200 pg of myelin oligodendrocytes glycoprotein $(MOG)_{35-55}$ peptide (Sequence: MEVGWYRSPFSRVVHLYRNGK, SEQ ID NO:33) emulsified in 100 µl complete Freund's Adjuvant supplemented with 400 µg of *Mycobacterium tuberculosis* H37RA (DIFCO Laboratories, Detroit, Mich., USA). On day 0 and 2, mice were injected intraperitoneally with 500 ng of *Pertussis* toxin (List Biological Laboratories, INC., Campbell, Calif., USA). Animals were monitored daily for signs of EAE and the scoring system was as follows: 0=no clinical symptoms; 0.5=partial floppy tail, 1=floppy tail; 2=ataxia; 2.5=weakness in hind limbs, 3=paralysis of one hind limb; 4=paralysis of both hind limbs, 5=moribund. Mice were scored by an investigator blinded to the treatment group.

T cell stimulation. $CD4^+$ $CD45RO^+$ lymphocytes T cells were isolated from peripheral blood (PB) mononuclear cells using the magnetic cell sorting (MACS™) isolation columns, according to manufacturer's protocol (Miltenyi®, Auburn, Calif.). Isolated CD4 T cells (one million cells/ml) were cultured with plate-bound anti-CD3 (2.5 µg/ml incubated 24 h at 4° C.) and soluble anti-CD28 (BD Pharmingen, 2 µg/ml). For $T_H17$ differentiation recombinant human IL-23 (25 ng/ml), anti-human IL-4 antibody (5 µg/ml) and anti-human interferon-gamma (IFNγ) antibody (5 µg/ml) were added, whereas IL-12 (10 ng/ml) in the presence of anti-IL4 was added for $T_H1$ differentiation, IL-4 (200 ng/ml) in the presence of anti-IFNγ and anti-IL12 antibodies (5 µg/ml) for $T_H2$ differentiation and IL-2 (20 U/ml) in the presence of anti-IL4 and anti-IFNγ antibodies was added for non-specific stimulation and cells were harvested at day 3 and day 6, if not specified otherwise (all reagents from R&D Systems®). All cultures and experimental procedures were carried out in X-VIVO™ 15 medium (Lonza®) without serum and supplemented with 2 mM I-glutamine, 100 U/ml penicillin and 100 µg/ml streptomycin (Sigma®). To study the influence of cytokines on DICAM expression assay, human $CD4^+CD45RA^+$ naive T lymphocytes obtained from the peripheral blood of a healthy donor were cultured for 6 days with plate-bound anti-CD3 and soluble anti-CD28 antibodies in the presence of neutralizing antibodies against IL-4 and IFNγ. Cytokines were added (alone or in combination; IL-1b (25 ng/ml), IL-6 (25 ng/ml), TGF-b (25 ng/ml) or IL-23 (25 ng/ml)).

Quantitative real-time PCR analysis of DICAM expression in cultured T lymphocytes. Total RNA was extracted using RNeasyTM Mini kit according to the manufacturer's instruction (Qiagen). RNA samples were transcribed into cDNA using Quantitect™ Reverse Transcription kit according to the manufacturer's instruction (Qiagen®). Relative gene expression levels were determined using primers and TaqMan™ FAM-labeled MGB probes for MXRA8 (DICAM), IL-17, IFN-γ, IL-23R, T-bet, GATA-3 and RORg and ribosomal 18S (VIC-labeled probe) (Applied Biosystems® respective product number:Hs00260584_m1, Hs00174383_m1, Hs00989291_m1, Hs00332759_m1, Hs00203436_m1, Hs00231122_m1 and Hs01076112_m1) and according to the manufacturer's instruction. qPCR cycling was performed according to the default temperature settings (2 min at 50° C., 10 min at 95° C., followed by 40 cycles of 15 s at 95° C., 1 min at 60° C.) in a 7900HT Fast-Real-Time™ PCR System (Applied Biosystems). Gene-specific mRNA was normalized compared to endogenous control (18S) and relative expression quantified by extrapolating from an internal control using cDNA from cells having high expression levels.

Western blot analysis of DICAM expression in cultured T lymphocytes. T lymphocytes cell lysates (30 µg) were separated by standard SDS-PAGE and immunoblots were analyzed with anti-DICAM (Goat; 1:100 dilution; sc-163102; Santa Cruz Biotechnology®); horseradish peroxidase-conjugated anti-goat (1:1,000 dilution; P00448; DakoCytomation) and the ECL system (Amersham Biosciences) were used to detect specific binding, and anti-actin (1:5,000 dilution; AC-15; MP Biomedicals®) served as a loading control. Digital images obtained with the Bio-Rad® Gel Doc system were used for quantification of band intensity with Quantity One® software (Bio-Rad®)

Immunostaining and confocal microscopy analysis of DICAM expression on mouse and human CNS specimens Post-mortem frozen sections (n=20) from brains of three patients with relapsing—remitting multiple sclerosis and four healthy controls (normal brain tissue from non-epileptic surgical human CNS material) were studied as previously described (Kebir et al., 2009). Freshly frozen sections (n=50) from EAE animals (n=10) sacrificed at Day 15 and from age-matched healthy controls (n=6 mice) were studied as previously described (Ifergan et al., 2006; Alvarez and Teale, 2008). Briefly, active multiple sclerosis and EAE lesions were identified by Luxol Fast Blue and haematoxylin and eosin staining and defined as areas of demyelination associated with intense perivascular immune cell infiltration. For immunohistofluorescence, sections were fixed in acetone for 10 min and then transferred to ethanol for 5 min, hydrated in PBS and blocked with 10% serum (from the same species that the fluorochrome-conjugated antibodies were derived) for 30 min at room temperature. Sections were incubated at room temperature for 60 min with primary antibodies diluted in 3% species specific serum. Sections were washed seven times with PBS and 0.05% Tween 20 after antibody incubation. Secondary antibodies were incubated for 40 min at room temperature when necessary. Then, sections were mounted using gelvatol containing TO-PRO®-3 (Invitrogen®, 1:300) when required. Negative controls using secondary antibodies alone were included in each experiment and found to be negative for staining. The following primary antibodies were used: goat anti-human DICAM (polyclonal Goat sc-163102; Santa Cruz Biotechnology®,1/30), rabbit anti-human laminin (polyclonal, DakoCytomation®, 1:500), Mouse anti human PECAM-1 (monoclonal, BD Biosciences® 1/200), Rabbit anti human Occludin (polyclonal, Invitrogen® 1/200), Rabbit anti human Z0-1 (polyclonal, Invitrogen® 1/50), mouse anti-human CD4 (monoclonal, BD Pharmingen®, clone RPA-T4 1/100) and mouse anti-human IL17 (monoclonal, R&D systems®, 1:50), When appropriate, we used the following secondary antibodies, either donkey anti-rabbit Rhodamine Red™-X (RRX) 1:500, goat anti-mouse Alexa Fluor® 488 1:400, donkey anti-mouse A546 1:300, donkey anti-goat Alexa Fluor® 549 or Alexa Fluor® 488 1:500 all from Jackson Immunoresearch®. Nuclei were stained with TOPRO-3 (1:300 in PBS; Molecular Probes®). Control staining was performed with an isotype control antibody. All images were acquired using a Leica SP5 confocal microscope and analyzed using the Leica® LAS AF software (Leica Wetzlar®). Expression of DICAM, IL-17A and IFN-γ was also assessed on $T_H1$ and $T_H17$ lymphocytes cultured in vitro. For that purpose, cytospined TH1 or $T_H17$ cells were permeabilized and fixed with cold acetone (for 10 minutes at −20° C.) and immunostained with anti-DICAM bet (polyclonal Goat sc-163102; Santa Cruz Biotechnology® 1/70) anti-IL17A (R&D Systems® 1/30) antibodies for 60 minutes at rt. Then, donkey anti-mouse A546 1:300, donkey anti-goat Alexa Fluor® 488 1:500 all from Jackson Immunoresearch® was added for 30 minutes at room temperature. All images were acquired using a Leica® SP5 confocal microscope and analyzed using the Leica® LAS AF software (Leica Wetzlar®).

Generation of anti-DICAM antibodies. Monoclonal anti-DICAM antibodies were custom made by ImmunoPrecise Antibodies® with rapid immunization strategy. Antigens (peptides: N-terminal, PRMVWTQDRLHDRQRC (SEQ ID NO: 52) and C-terminal, CYSDQKSGKSKGKDV (SEQ ID NO: 53)) at 0.5mg/L were emulsified in Freund's complete adjuvant and used to immunize 4 female BALM mice intraperitoneally. The booster injections of antigen in Freund's complete adjuvant was performed at 3 weeks intervals. Mouse sera (test bleed) was collected 7-10 days following the second boost and checked for specific antibody titre by ELISA. Responding mice received antigen intravenous boost and be used as spleen donors for cell fusion hybridoma cell line generation. Spleen cells from responding immunized mice were isolated, purified and fused with murine SP2/0 myeloma cells in the presence of poly-ethylene glycol. Fused cells are cultured using ImmunoPrecise Antibodies® proprietary cloning method (HAT selection). Approximately 10 days after the fusion event, up to 948 of the resulting hybridoma clones were transferred to 96-well tissue culture plates and grown in HT containing medium until mid log growth is reached. Up to 948 hybridoma tissue culture supernatants were transferred to antigen coated FiLISA plates from the 96-well culture plates. An indirect ELBA is performed probing with secondary antibody for both IgG and IgM monoclonal antibodies. Positives cultures were retested on immunizing antigen to confirm secretion and on irrelevant antigen to eliminate non specific or "sticky" mAbs and rule out false positives. The hybridoma cell lines were maintained in culture for 32 days post transfer to 96-well plates and subcloned to ensure stability and secretion. This is referred to as the stability period. Subclones 9E9.1 and 9E9.2 were generated by serial dilution and single expansion according to ImmunoPrecise Antibodies® proprietary cloning method. In order to validate anti-DICAM monoclonal antibodies by Western blot and flow cytometry, NIH3T3 cells transfected with human DICAM-encoding vector (pCMV6-neo) or with empty vector (pCMV6-neo) were generated. Stably transfected clones were selected and expanded using Geneticin G418.

Characterization of anti-DICAM antibodies by Western blot THP-1 and NIH3T3 cells transfected with human DICAM-encoding vector (pCMV6-neo) or with empty vector (pCMV6-neo) cell lysate (30 pg) were loaded on 12% SDS-PAGE gel and electrophoresed for 90 min at 100V and transferred to PVDF membranes. Hybridoma from clones 3C2, 2C11, 2H12, 9E9 and 1B2 (directed against the N terminal DICAM epitope) or from clone 7F8, 1 D9, 4B8 and 1 D4 (directed against the C terminal DICAM epitope) were incubated at 4° C. (50 µg/ml) for 12 h. Secondary antibody is goat anti-mouse pan-IgG coupled to HRP (1/2000 dilution). Actin is shown as a loading control. N=4 by standard SDS-PAGE and immunoblots were analyzed with anti-DICAM (Goat; 1:100 dilution; sc-163102; Santa Cruz Biotechnology®); horseradish peroxidase-conjugated anti-goat (1:1,000 dilution; P00448; DakoCytomation®) and the ECL system (Amersham Biosciences®) were used to detect specific binding, and anti-actin (1:5,000 dilution; AC-15; MP Biomedicals®) served as a loading control. Digital images obtained with the Bio-Rad® Gel Doc system were used for quantification of band intensity with Quantity One® software (Bio-Rad®)

Characterization of anti-DICAM antibodies by flow cytometry. Flow cytometry was performed as described in Kebir et al. *Nature Medicine* 2007. Anti-DICAM hybridomas (2H12, 1B2, 2c11, 3C2, 9E9, 1 D4, 7F8, 1 D9, 4B8) were used at 5 µg in 100 µl in FACS buffer. An anti-mouse PE-conjugated antibody was used to detect hybridoma binding. Flow cytometry experiments were performed on a BD LSR II Flow cytometer. Isotype control and secondary Ab-PE were used as negative controls. n=5-6 experiments.

$T_H17$ migration assay for the characterization of anti-DICAM antibodies. BBB-ECs grown in primary cultures were used to generate an in vitro model of the human BBB, as previously described (Cayrol et al., *Nature Immunol* 9(2): 137-45 Epub 2007 Dec. 23). Human BBB-endothelial cells ($25 \times 10^3$ cells/chamber) were grown in primary culture on 3 µm porous membrane (Becton Dickinson® Labware, Franklin Lakes, N.J., USA), coated with 0.5% gelatin (Sigma®), in endothelial cell culture media supplemented with 40% ACM, for 4 days to reach confluency. The BBB-endothelial cells were treated with 20 µg/ml of isotype control or 20 µg/ml of anti-human DICAM antibody one hour prior to the addition of the leukocytes. Human ex vivo lymphocytes were isolated, from consenting healthy donors, as described above. The leukocytes were added to the upper chamber ($1 \times 10^6$ cells/chamber) and were allowed to migrate across human BBB-endothelial cells for 18 h. The cells that migrated through the BBB-endothelial cells, were recovered from the lower chamber and characterized by flow cytometry. All migration data shown represent at least 3 independent experiments performed in triplicate.

Antibody Sequencing. RT-PCR was carried out using 5' RACE and gene specific reverse primers which amplify mouse immunoglobulin heavy chain (IgG1 and IgG2b) and light chain (kappa) variable region sequences. The specific bands were excised and cloned into pCR-Blunt II-TOPO for sequencing, and the constructs were transformed into *E. coli*. 16 colonies of each chain were picked & PCR screened for the presence of amplified regions prior to sequencing; additional colonies were picked as necessary. Selected PCR positive clones (8 heavy chain and 8 kappa chain) were sequenced. DNA sequences were analyzed by BLAST to confirm homology to mouse antibody sequences.

Purification and labeling of antibody clone 9E9. Antibody 9E9, developed by Immunoprecise™ as monoclonal antibody hybridoma cell lines and produced as cell culture supernatant, was fully purified using a Protein G Sepharose™ 4 Fast Flow (Fractionation of Monoclonal Antibodies, without Binding Albumin, Cat-17-0618-01, VWR) according to the manufacturer's instructions. After purification, the anti-DICAM 9E9 was labeled with the red fluorescent dye CF647, which is spectrally similar to Alexa Fluor® 647, using the Mix-n-Stain™ CF™ 647 kit, lot: 14M1222K, according to the manufacturer's instructions.

Flow cytometry and intracellular staining. For lymphocyte intracellular cytokine staining (ICS), cells were activated for 4 h30 unless specified otherwise with 1 µg/mL ionomycin and 20 ng/mL phorbol 12-myristate 13-acetate (PMA) in the presence of 2 µg/mL brefeldin A (all from Sigma®). Cells were stained for surface antigens and fixed/permeabilized using BD Biosciences® Cytofix/Permeabilization kit. Mice immune cells isolated from lymph nodes, spleen and CNS were labelled using antibodies specific for the surface markers CD3 (A700 or PerCpCy5.5), CD4 (FITC), CD8 (PB), CD45 (PerCpCy5.5), (all from BD Biosciences®) and for the intracellular cytokines IL-17 (PE) and IFNγ (APC) (BD Biosciences®). Appropriate fluorochrome-matched isotype antibodies were used as controls to assess nonspecific background staining. All cell staining were acquired on a BD LSR® II (Becton Dickinson®) and analyzed using the BD FACSDiva® software (BD Bioscience®).

Statistical analysis. Statistical analyses were performed using PRISM 4 Graphpad™ Software (San Diego, Calif.) and data are presented as the mean±the standard error of the mean (SEM). One-way analysis of variance (ANOVA) was performed followed by Bonferroni multiple comparison post-test for all experiments except for the migration across the BBB, which was done using two-way ANOVA. Only p values<0.05 were considered significant. The data reported are either from either one representative experiment out of 3 independent experiments or pooled from 3 to 10 experiments. Differences between groups were considered significant when p<0.05.

EXAMPLE 2

Expression of DICAM and Other Molecules by Activated Human Memory Lymphocytes

Figure 2:
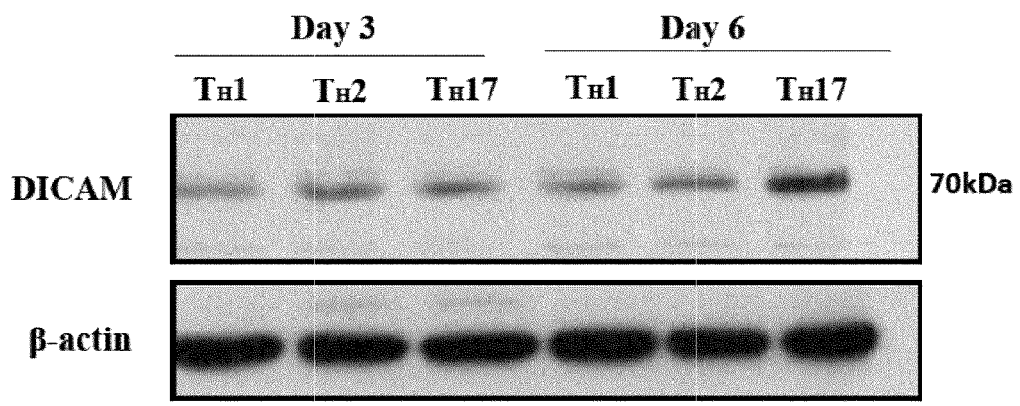
FIG. 2 shows that DICAM protein is specifically increased in $T_H17$ lymphocytes differentiated from human memory lymphocytes $CD4^+CD45RO^+$. Western Blot (WB) analysis of the expression of DICAM in $T_H1$, $T_H2$ and $T_H17$ lymphocytes differentiated in vitro using memory lymphocytes $CD4^+CD45RO^+$ from healthy volunteers activated with anti-CD3/anti-CD28 antibodies under $T_H0$, $T_H1$, $T_H2$ or $T_H17$ polarizing conditions (as described above). After 3 and 6 days of the culture, the expression of DICAM was determined by WB at Day 3 and Day 6. β-actin was used as loading control. Data shown are representative of 5 independent experiments.
Figure 3A:
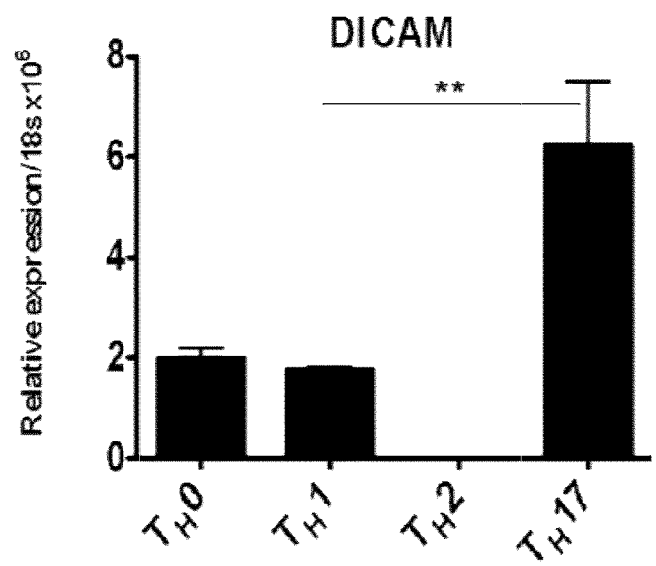
FIGS. 3A to F show that DICAM mRNA and protein are expressed in human $T_H17$ lymphocytes differentiated from naive $CD4^+CD45RA^+$ lymphocytes. $T_H1$, $T_H2$ and $T_H17$ lymphocytes were differentiated in vitro using naive lymphocytes $CD4^+CD45RO^+$ with anti-CD3/anti-CD28 antibodies in the absence of cytokine ($T_H0$), or in the presence of IL-12 ($T_H1$), IL-4 ($T_H2$), or IL-23 ($T_H17$). After 6 days of the culture, the expression of RNA messenger of DICAM (FIG. 3A), IL-17 (FIG. 3B) IFNγ (FIG. 3C), RORγ (FIG. 3D) and Tbet (FIG. 3E) were etermined by QPCR at Day 6.
Figure 3B:
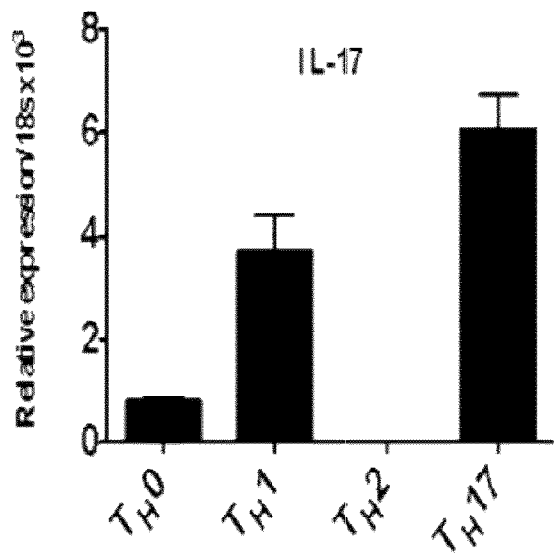
Figure 3C:
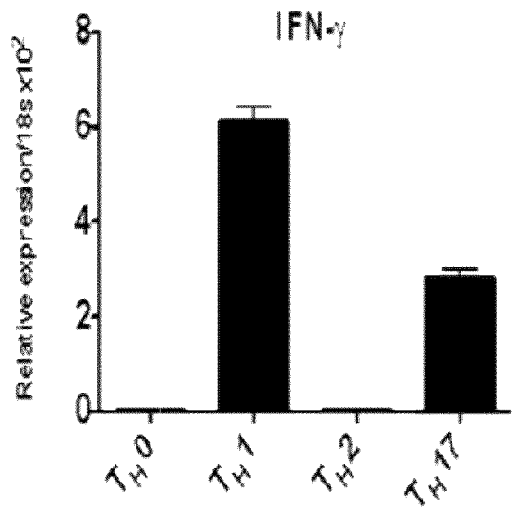
Figure 3D:
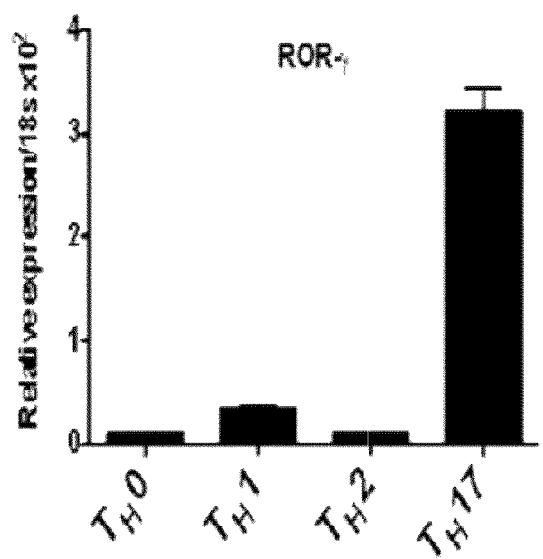
Figure 3E:
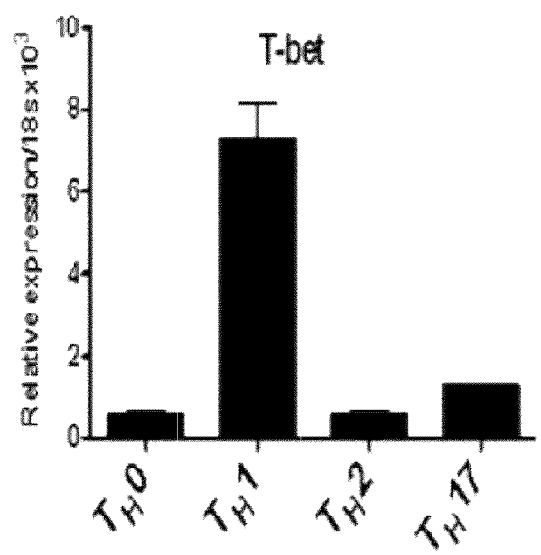
Figure 3F:
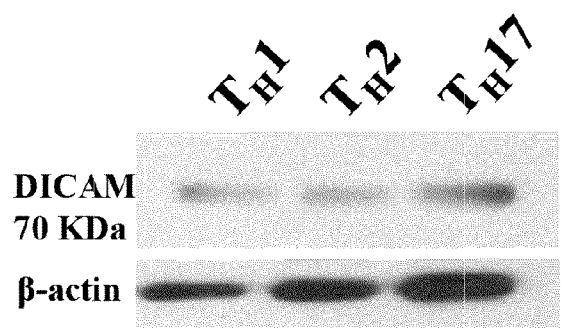
Figure 4A:
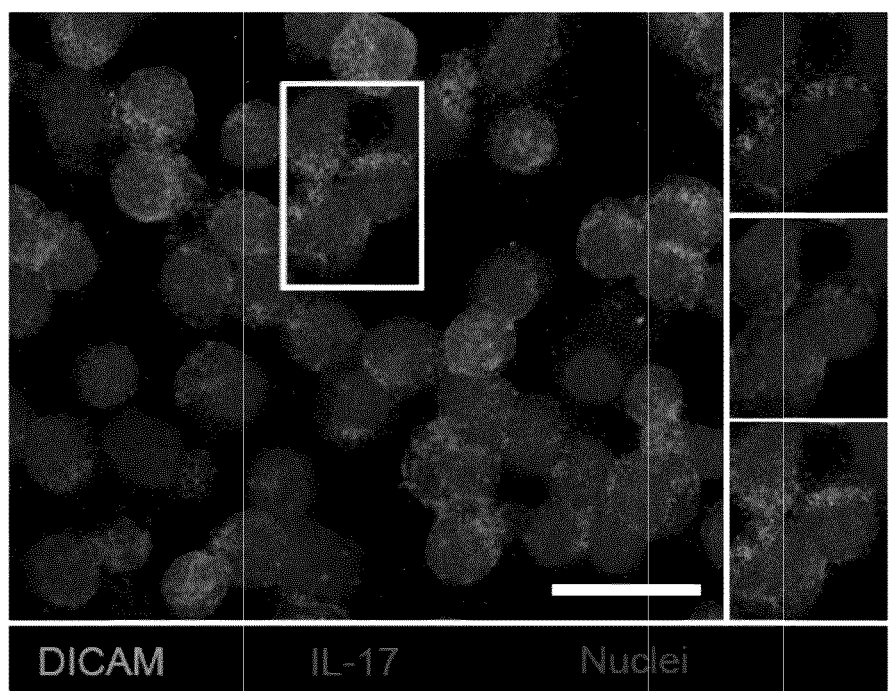
FIGS. 4A and 4B show that DICAM is mostly expressed on human IL-17-producing CD4 T lymphocytes. Human $CD4^+CD45RO^+$ memory lymphocytes obtained from the peripheral blood of a healthy donor were activated for 6 days with anti-CD3 and anti-CD28 antibodies and skewed towards a $T_H17$ (FIG. 4A) or a $T_H1$ (FIG. 4B) phenotype. $T_H17$ and $T_H1$ lymphocytes were then cytospined and immunostained for DICAM and IL-17 (FIG. 4A) or DICAM and IFN-γ (FIG. 4B). Nuclei were stained with TO-PRO-3. Scale bars: 20 μm. Data shown are representative of 4 donors.
Figure 4B:
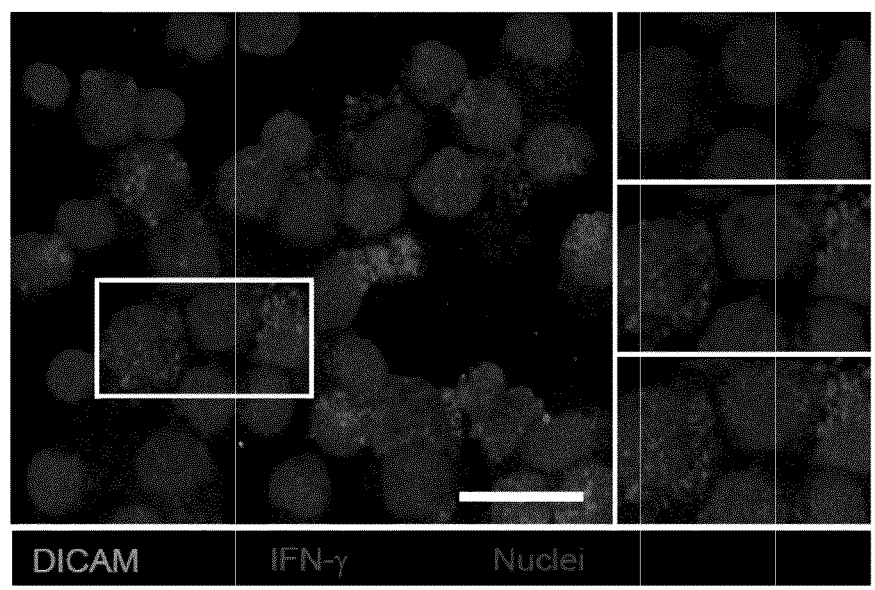
Figure 5A:
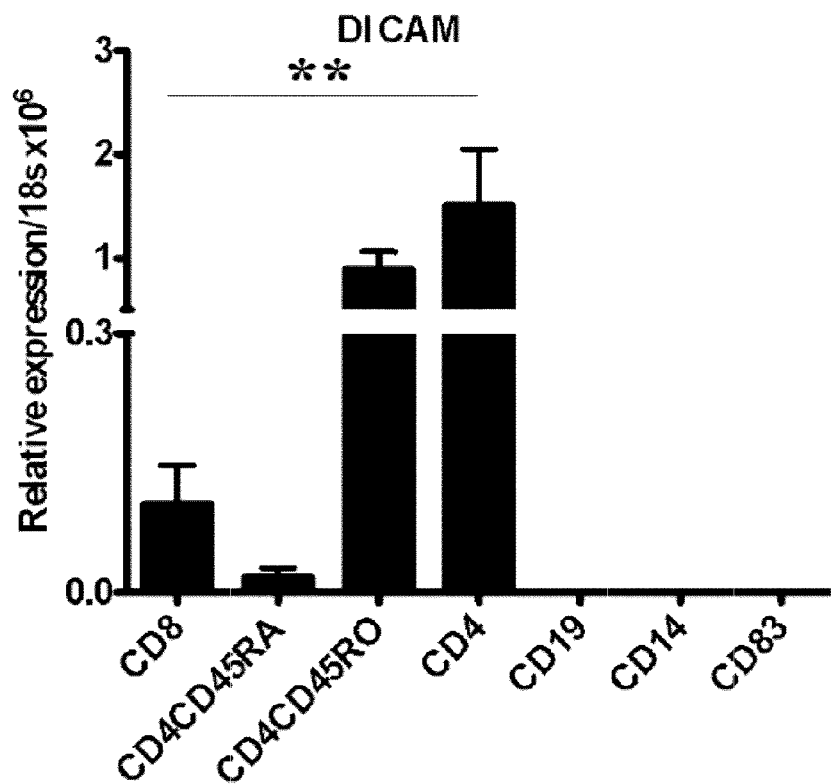
FIGS. 5A and B show that DICAM is expressed in human CD4 and CD8 T lymphocytes.
Figure 5B:
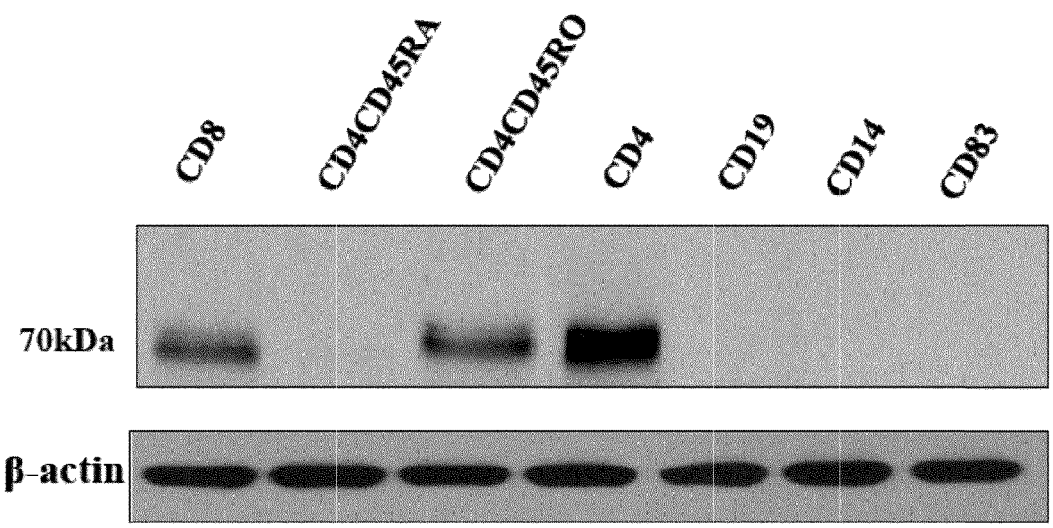
FIG. 5B: Western blot analysis of the expression of DICAM in ex vivo human immune cells abovementioned.**, P<0.05.

FIG. 1A and FIG. 2 show that DICAM is expressed in CD4$^+$CD45RO$^+$ memory lymphocytes from healthy donors activated with anti-CD3/anti-CD28 antibodies and cultured under $T_H17$ polarizing conditions for 6 days, both at the mRNA (FIG. 1A) and protein (FIG. 2) levels. This pattern of expression was also observed in $T_H17$ lymphocytes differentiated from naive CD4$^+$CD45RA$^+$ lymphocytes (FIGS. 3A, 3F). FIGS. 4A and 4B show that DICAM is mostly expressed on human IL-17-producing CD4$^+$CD45RO$^+$ memory T lymphocytes, as assessed by immunostaining. FIGS. 5A and 5B show that DICAM is expressed at low levels in CD8$^+$ and at high levels in CD4$^+$ cells, particularly in the CD4$^+$CD45RO$^+$ memory subset, both at the mRNA (FIG. 5A) and protein (FIG. 5B) levels. FIGS. 6A show that $T_H17$ polarizing cytokines IL-1, TGF-β, IL-6 and IL-23 induce DICAM mRNA expression in human CD4 lymphocytes.

EXAMPLE 3

Expression of DICAM in Lymphocytes from MS Patients

Figure 8A:
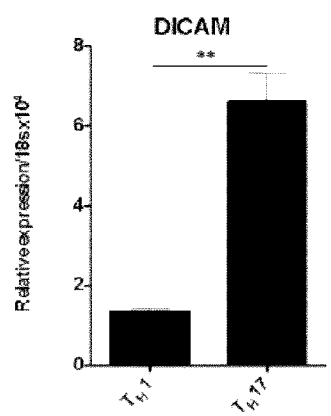
FIGS. 8A to E show that DICAM mRNA expression is increased in $T_H1$ and $T_H17$ lymphocytes differentiated from the blood of MS patients. $T_H1$ and $T_H17$ lymphocytes were differentiated in vitro using memory lymphocytes $CD4^+$ $CD45RO^+$ from untreated relapsing-remitting patients with MS activated with anti-CD3/anti-CD28 antibodies in the presence of IL-12, IL-4 and IL-23. After 6 days of the culture, the expression of RNA messenger for DICAM (FIG. 8A), IL-17 (FIG. 8B), IFNγ (FIG. 8C), RORγ (FIG. 8D) and Tbet (FIG. 8E) were determined by RT-PCR at Day 6. *, P<0.05, **, P<0.01.
Figure 8B:
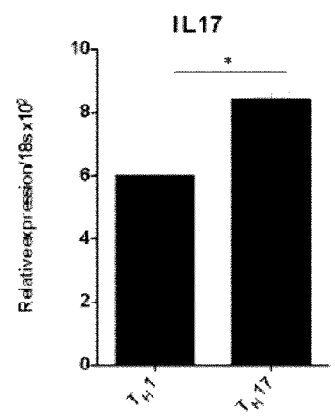
Figure 8C:
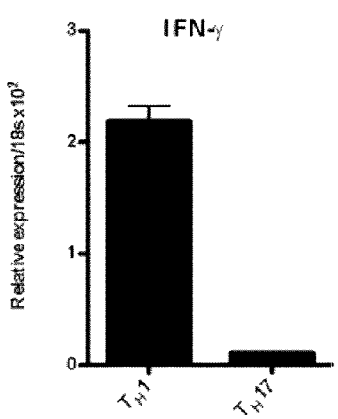
Figure 8D:
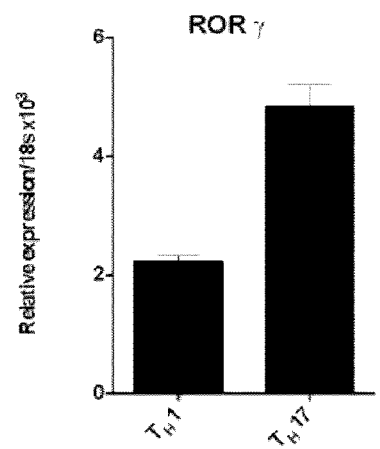
Figure 8E:
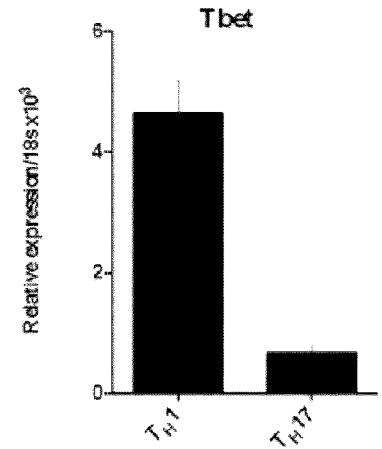

FIG. 7 shows that DICAM mRNA expression is significantly increased in human CD8$^+$ and CD4$^+$ lymphocytes from untreated relapsing-remitting Multiple Sclerosis (RRMS) patients, and FIG. 8A shows that DICAM mRNA expression is strongly increased in $T_H17$ lymphocytes differentiated from the blood of MS patients.

EXAMPLE 4

Expression of DICAM and αVβ3 Integrins at the BBB

Figures 9A, 9B:
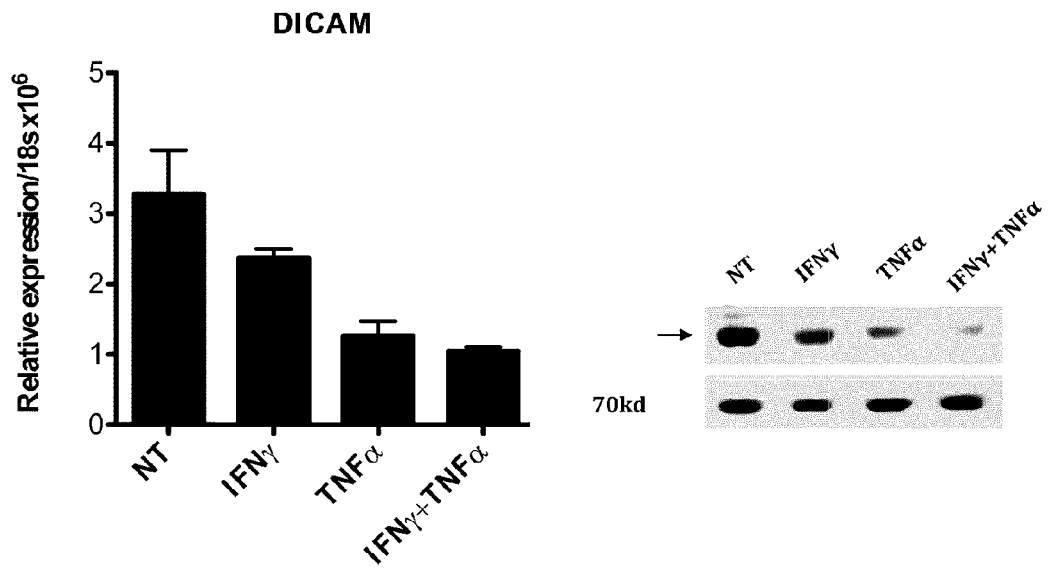
FIGS. 9A and 9B show that under proinflammatory conditions, DICAM expression is decreased in primary cultures of human BBB-ECs. After 48 hours of culture, the expression of DICAM mRNA (FIG. 9A) and protein (FIG. 9B) was assessed. Representative qPCR and Western blots of expression of DICAM from human blood-brain barrier endothelial cells, under resting (NT) and inflammatory (TNFα/IFNγ, 100 U/ml) conditions. All data shown are representative of 3 independent experiments.
Figure 10:
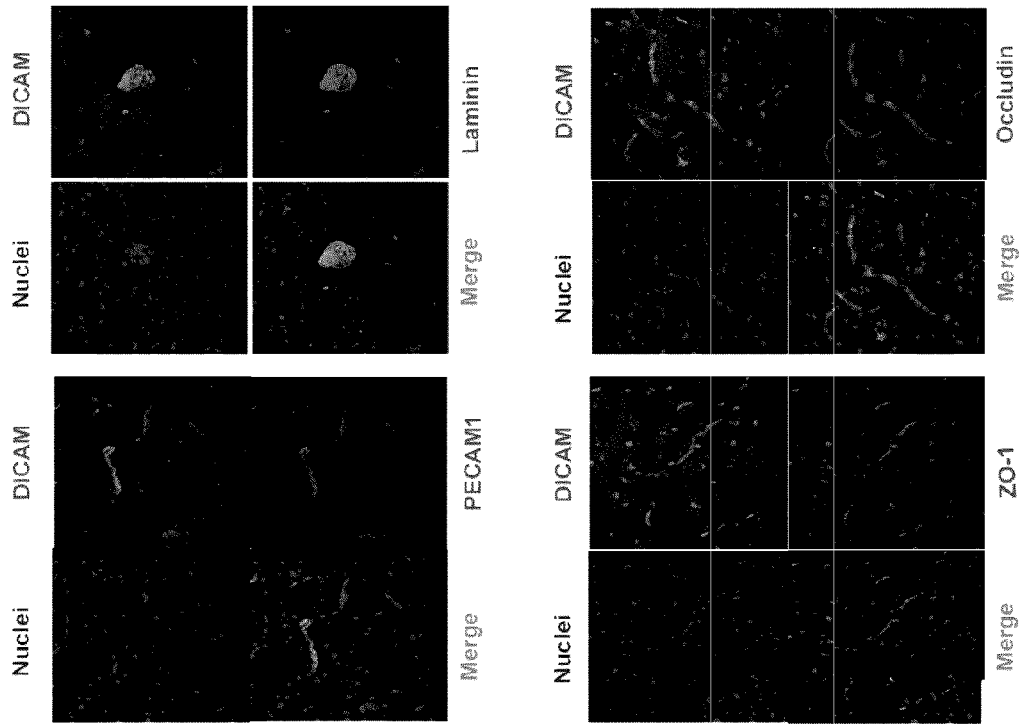
FIG. 10 shows that DICAM is expressed at the BBB in human normal-appearing white matter (NAWM). Confocal microscopy of material from human CNS normal-appearing white matter (NAWM) from patients with MS immunostained with antibodies specific for DICAM and Laminin, Occludin, PECAM1 and ZO-1. Data are representative of five experiments with five patients.

FIGS. 9A and 9B show that under proinflammatory conditions, DICAM mRNA and protein expression are decreased in primary BBB-ECs. FIG. 10 shows that DICAM is expressed at the BBB in human normal-appearing white matter (NAWM) from MS patients.

EXAMPLE 5

Expression of DICAM on Samples from MS Patients

Figure 11A:
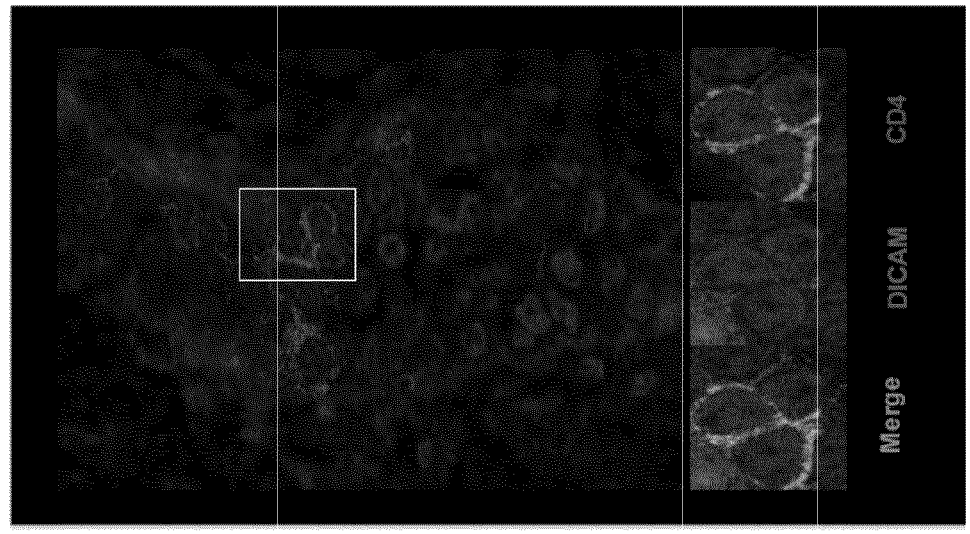
FIGS. 11A and 11B show that DICAM is expressed on IL-17-producing $CD4^+$ infiltrating lymphocytes in active MS lesions.
Figure 11B:
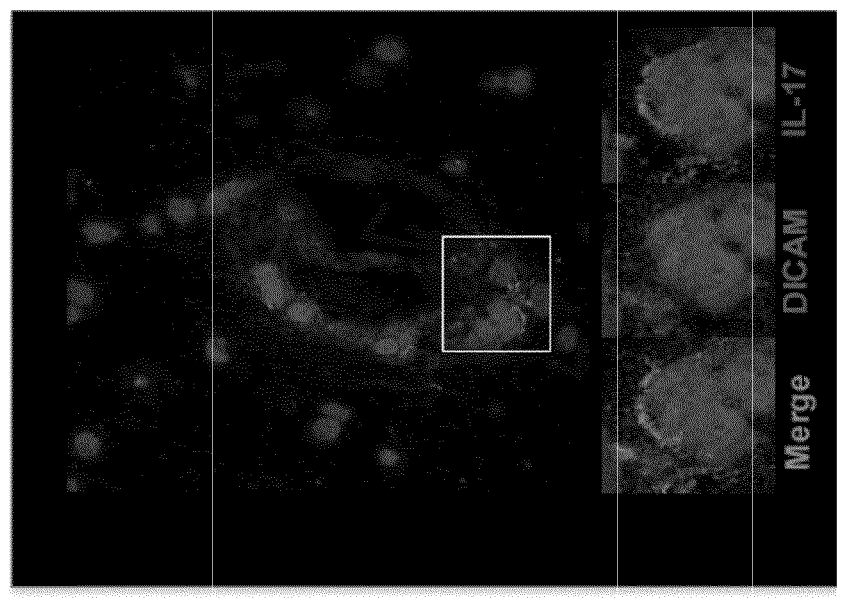
Figure 12:
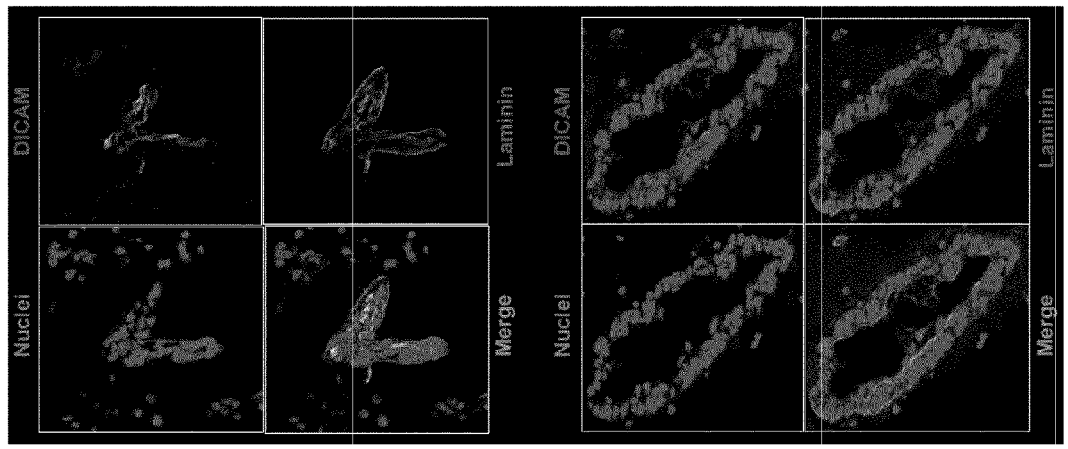
FIG. 12 shows that DICAM expression is decreased at the BBB in active MS lesions. Confocal microscopy of CNS active lesions from patients with MS stained with antibodies specific for DICAM and Laminin. Data are representative of 10 active lesions from five patients with multiple sclerosis.

FIGS. 11A and 11B show that DICAM is expressed on IL-17-producing CD4+ infiltrating lymphocytes in active MS lesions, as determined by immunofluorescent staining and confocal microscopy analysis and FIG. 12 shows that DICAM expression is decreased at the BBB in active MS lesions.

EXAMPLE 6

Expression of DICAM on Samples from Normal and EAE Mice

Figure 13:
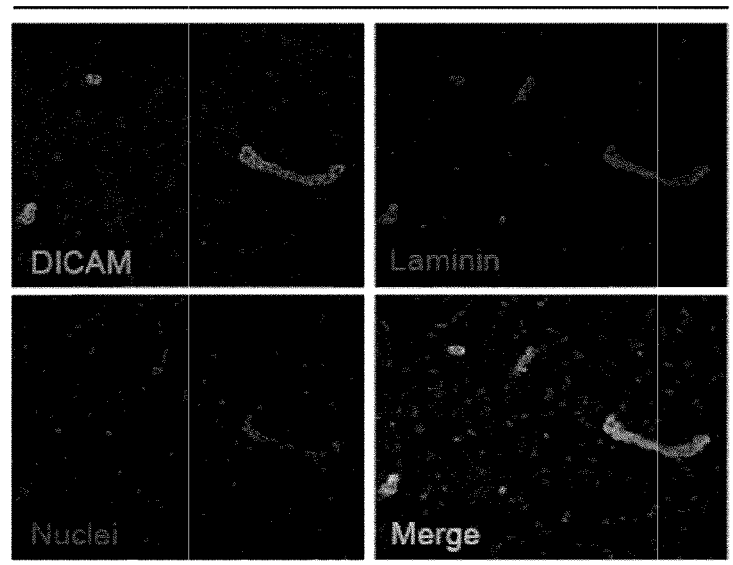
FIG. 13 shows that DICAM is expressed at the BBB in the CNS of naïve C57BL/6 mice. Confocal microscopy of CNS material from naive mice immunostained with antibodies specific for DICAM and Laminin. Data are representative of five experiments with five mice.
Figure 14:
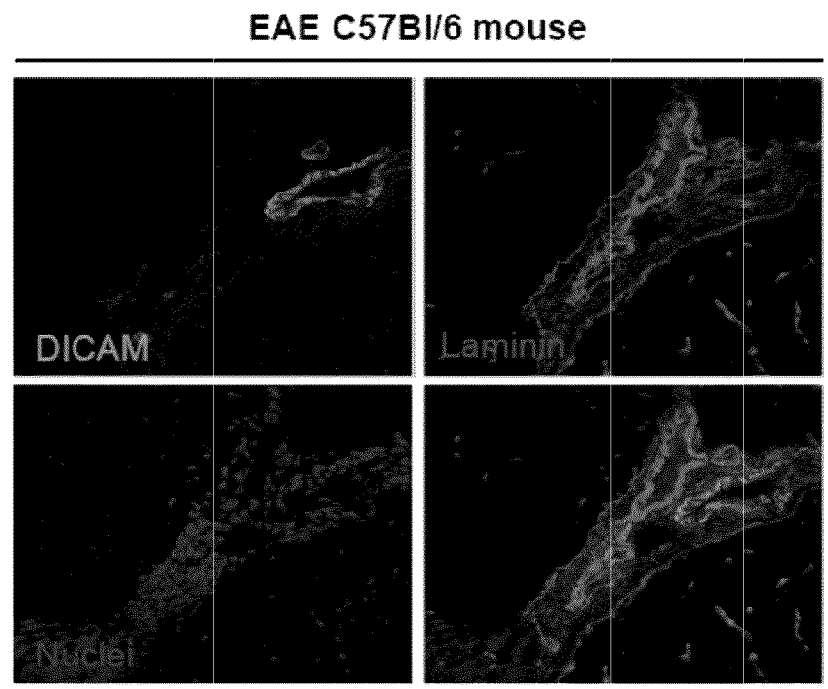
FIG. 14 shows that DICAM is expressed at the BBB in the CNS of C57BL/6 mice with experimental autoimmune encephalomyelitis (EAE). Confocal microscopy of CNS material from mice with EAE immunostained with antibodies specific for DICAM and Laminin. Data are representative of 10 sections from animals with EAE (score: 4,5).

The data presented in FIGS. 13 and 14 demonstrate that DICAM is expressed at the BBB in the CNS of (i) naïve (FIG. 13) and experimental autoimmune encephalomyelitis (EAE) C57BL/6 mice (FIG. 14).

EXAMPLE 7

Screening of Hybridoma Efficacy to Recognize DICAM

Figure 15:
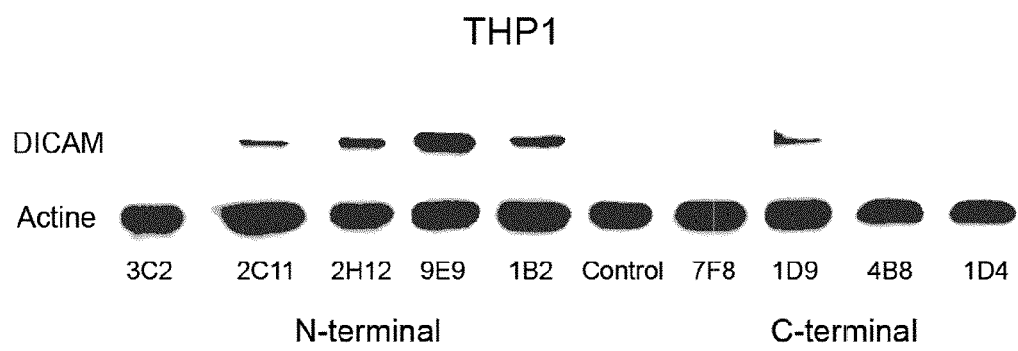
FIG. 15 shows a Western blot screening of hybridoma efficacy to recognize DICAM. THP-1 cells express DICAM as determined by qPCR and confirmed by WB (see Jung et al., *Journal of Bone and Mineral Research*, Vol. 27, No. 9, pp 2024-2034, 2012). THP-1 cell lysate (30 μg) were loaded on 12% SDS-PAGE gel and electrophoresed for 90 min at 100V and transferred to PVDF membranes. Hybridoma from clone 3C2, 2C11, 2H12, 9E9 and 1B2 (N-terminal DICAM epitope 57-71) or from clone 7F8, 1D9, 4B8 and 1D4 (C-terminal DICAM epitope 372-385) were incubated at 4° C. (50 μg/ml) for 12 h. Secondary antibody is goat anti-mouse pan-IgG coupled to HRP (1/2000 dilution). Actin is shown as a loading control. N=4
Figure 16A:
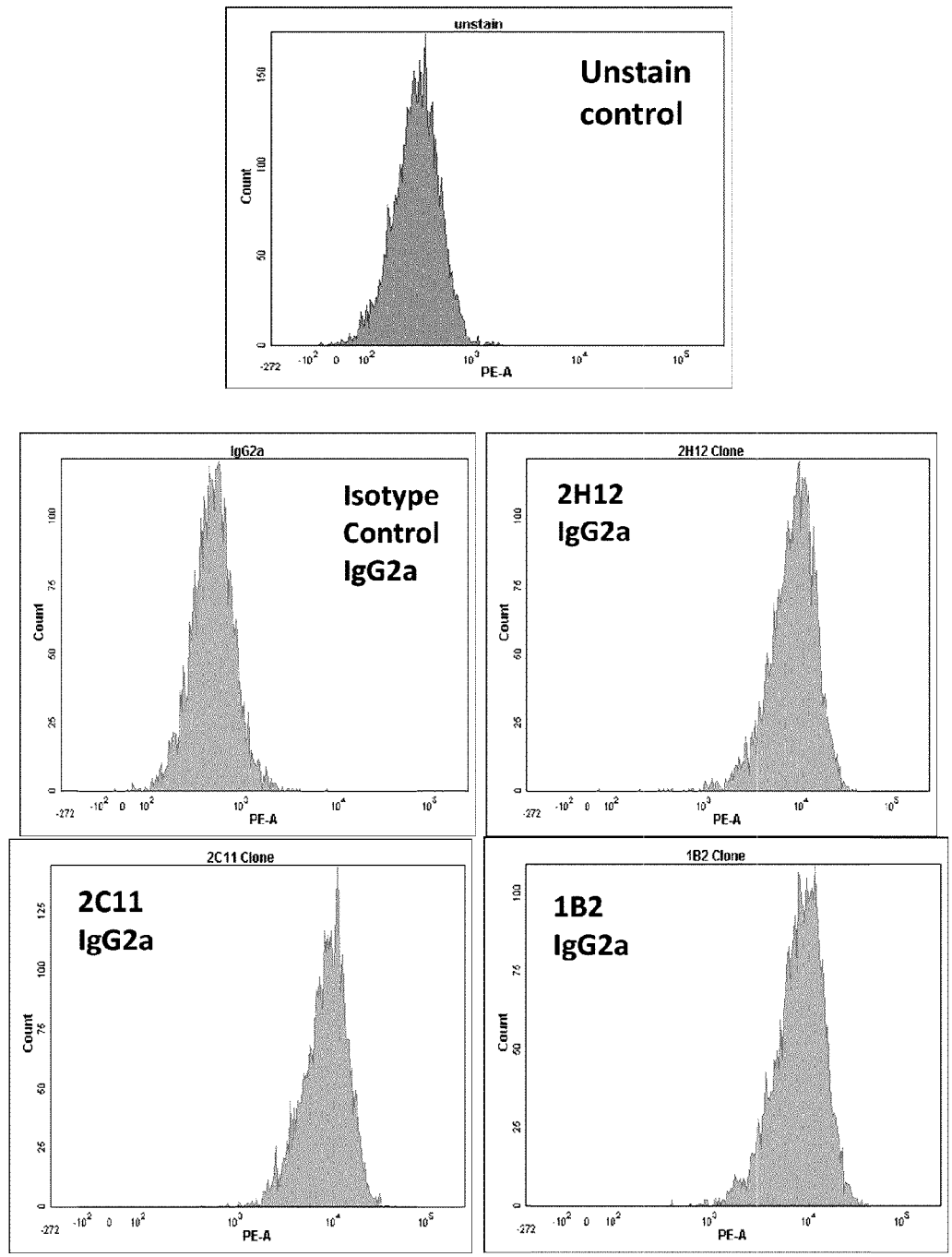
FIGS. 16A and 16B show hybridoma screening by flow cytometry on THP1 cells of anti-DICAM antibodies generated using the N-terminal human DICAM epitope (57-71). THP-1 cells were immunostaining with anti-DICAM clones 2H12, 2C11, 1B2, 9E9 (5 μg in 100 μl) at 4° C. for 45 minutes, counterstained with PE-conjugated anti-IgG2a (FIG. 16A) or anti-IgG1 (FIG. 16B) for 30 min and analyzed by flow cytometry on a BD® LSR II flow cytometer (N=4).
Figure 16B:
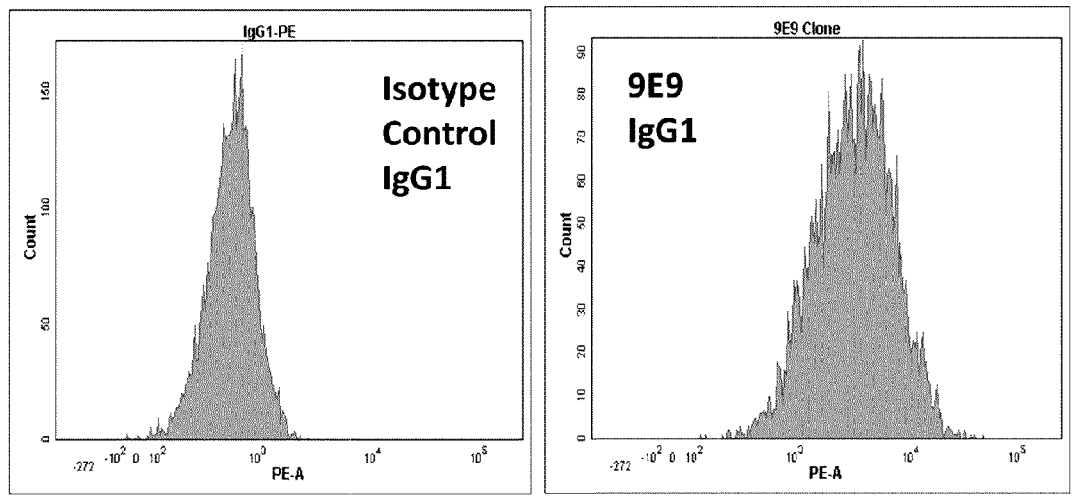
Figure 17A:
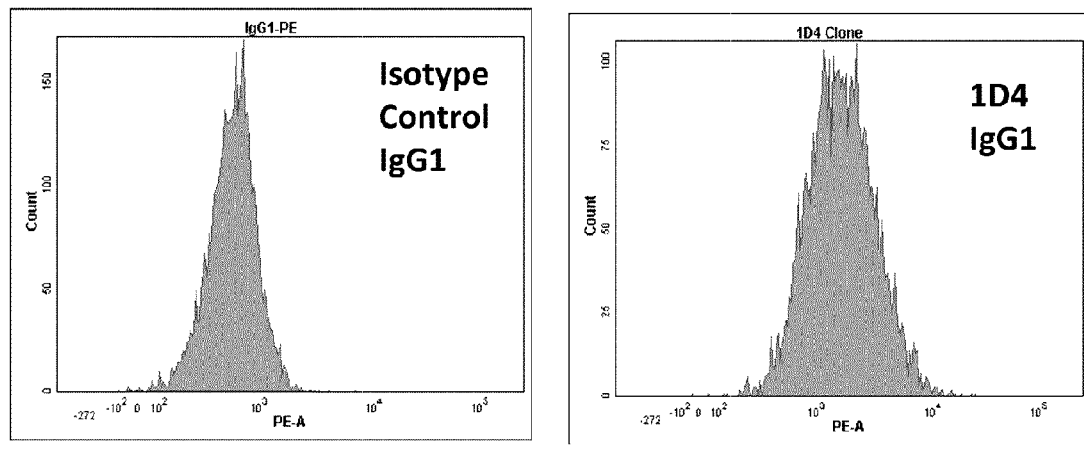
FIGS. 17A to 17C show hybridoma screening by flow cytometry on THP1 cells of anti-DICAM antibodies generated using the C-terminal human DICAM epitope (372-385). THP-1 cells were immunostaining with anti-DICAM clones 1D4, 1D9, 3C2, 7F8 and 4B8 (5 μg in 100 μl) at 4° C. for 45 minutes, counterstained with PE-conjugated anti-IgG2b (FIG. 17A), anti-IgG2a (FIG. 17B) or anti-IgG1 (FIG. 17C) for 30 min and analyzed by flow cytometry on a BD® LSR II flow cytometer (N=4).
Figure 17B:
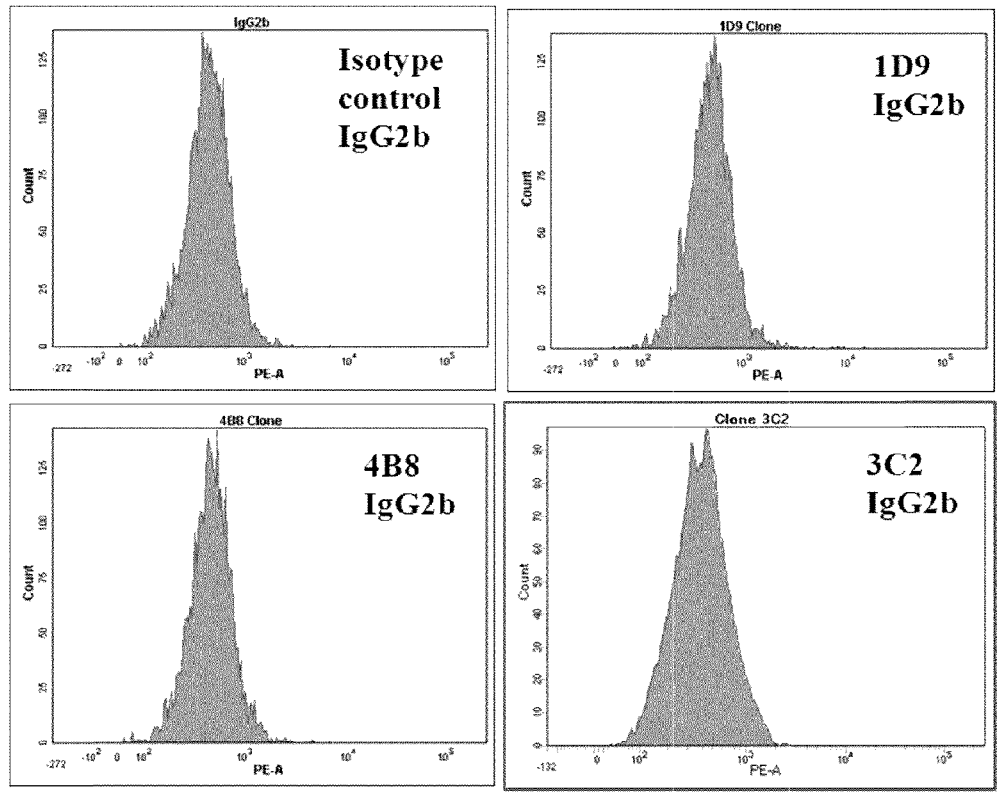
Figure 17C:
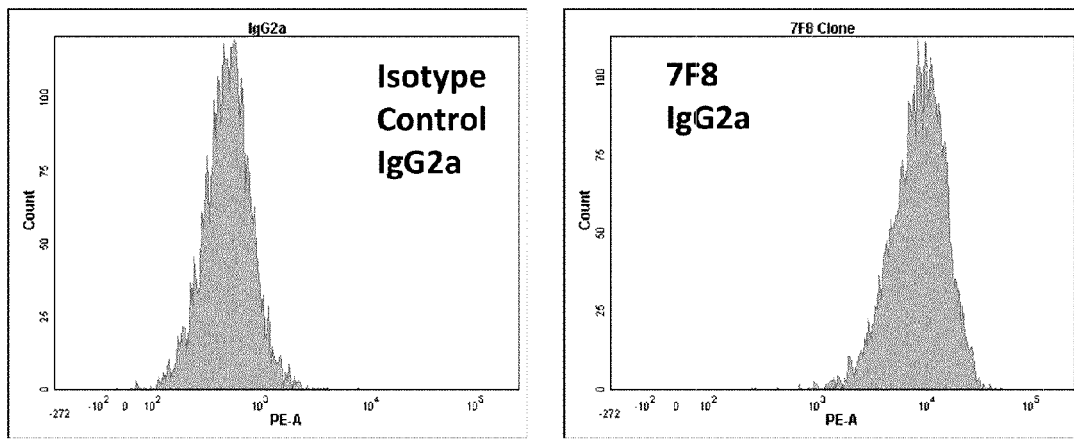
Figure 18A:
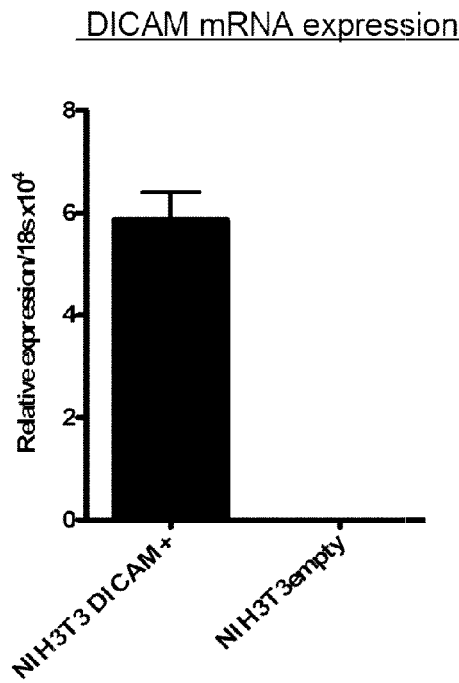
FIGS. 18A to 18E show the characterization of anti-DICAM monoclonal antibody clones 1B2 and 9E9. NIH3T3 cells were transfected with human DICAM-encoding vector (pCMV6-neo-DICAM) or with empty vector (pCMV6-neo). Stably transfected clones were selected and expanded using Geneticin G418.
Figure 18B:
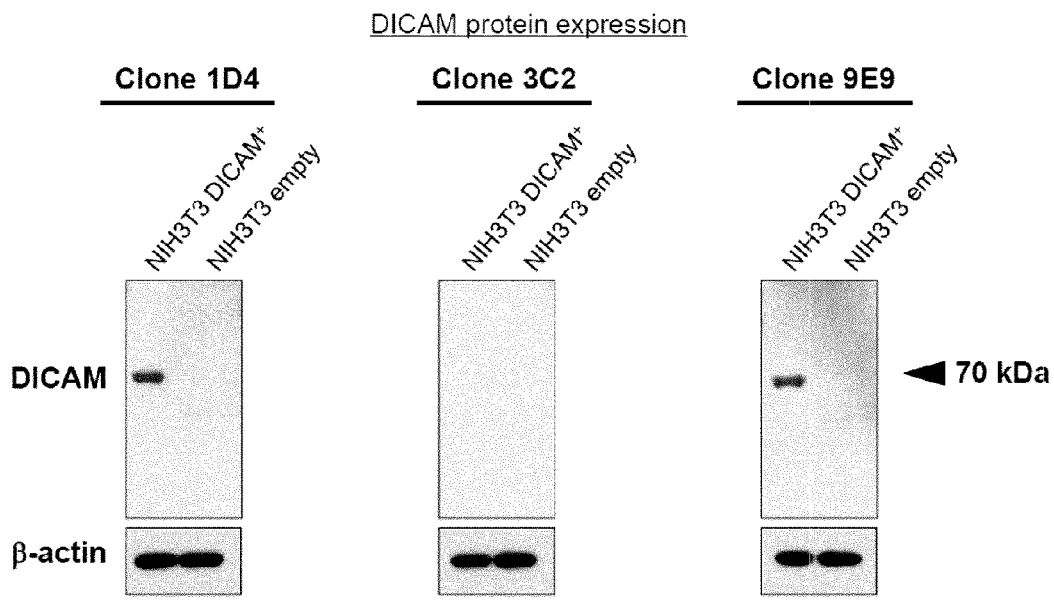
Figure 18C:
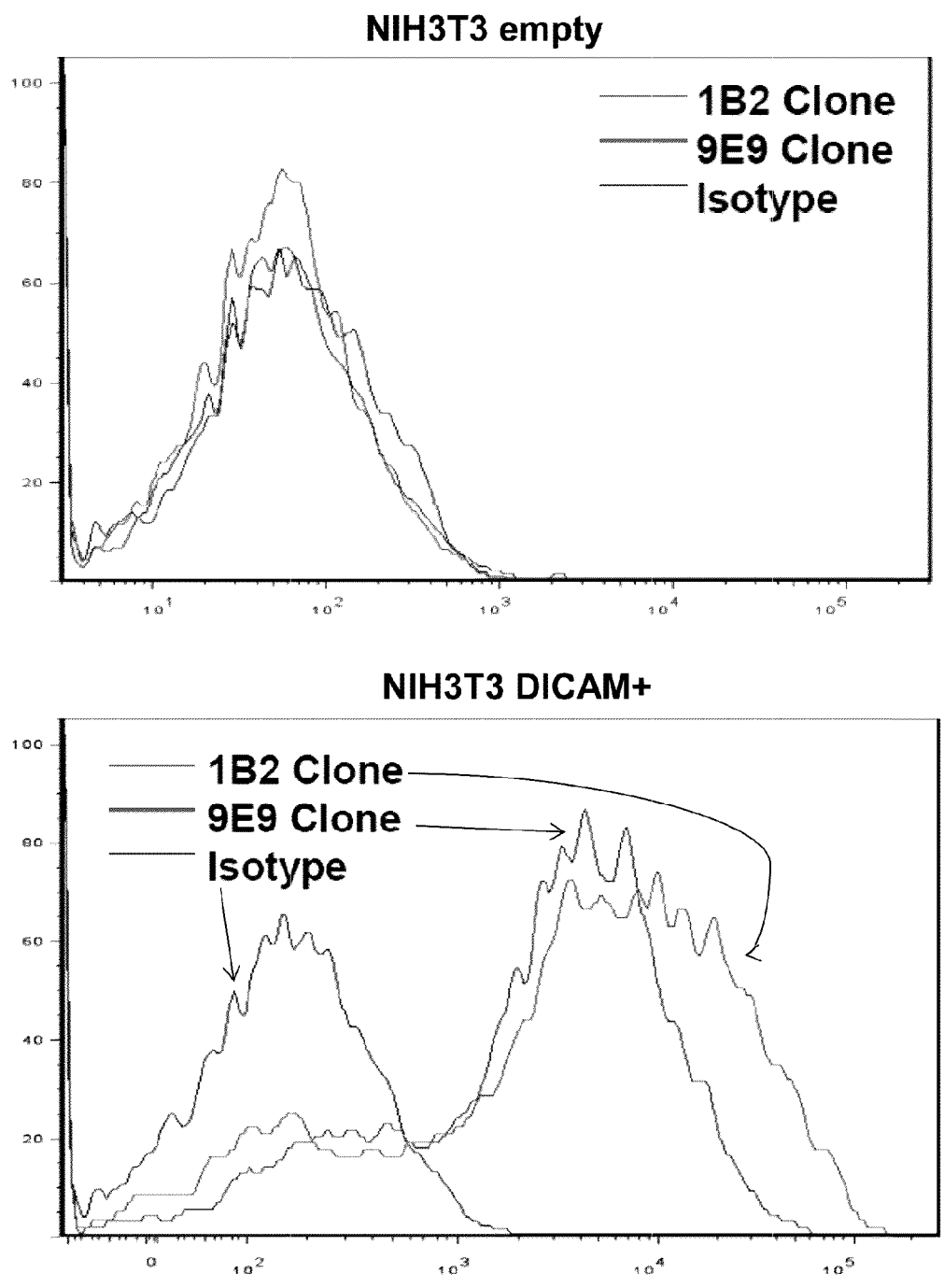
Figure 18D:
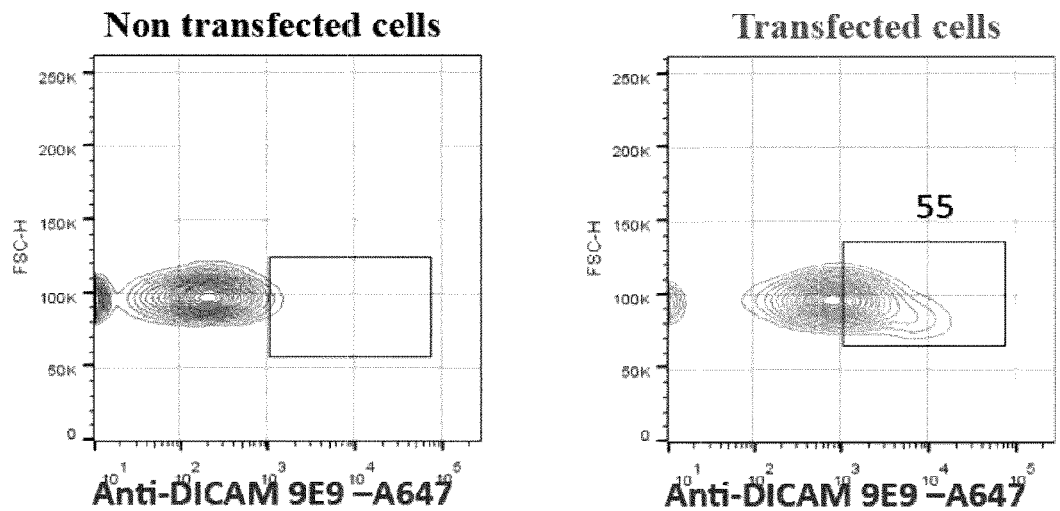
Figure 18E:
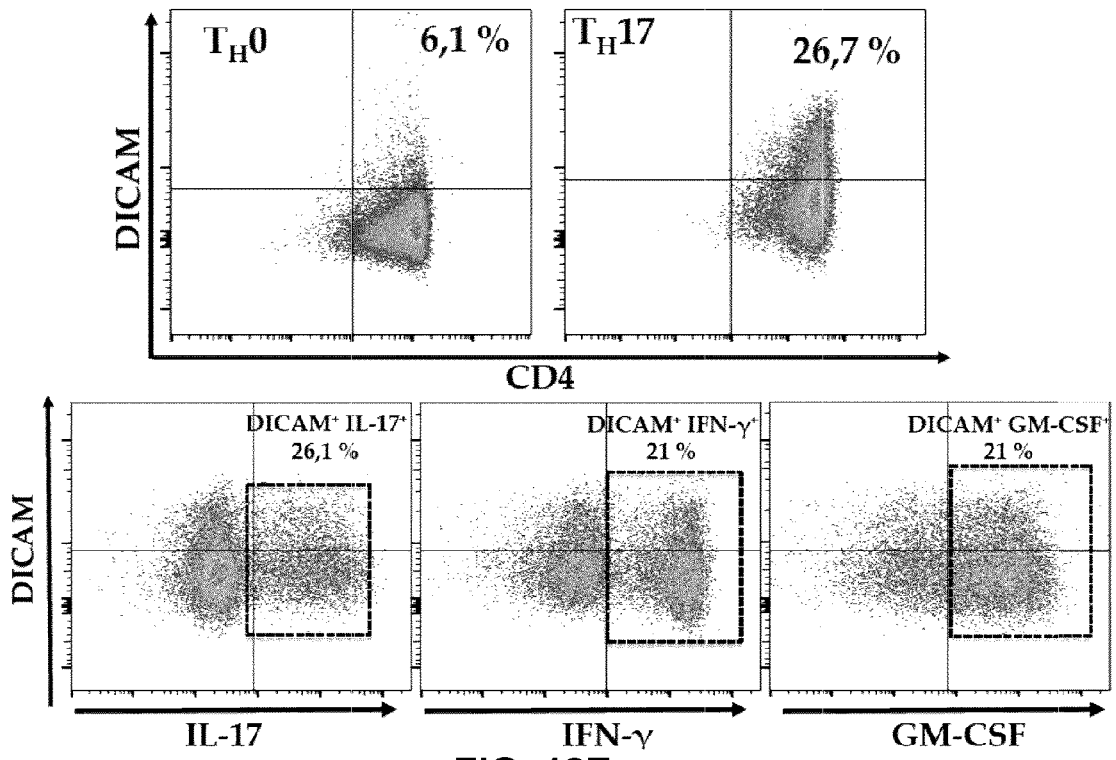

As shown in FIG. 15, the anti-DICAM antibodies from hybridoma clones 2C11, 2H12, 9E9 and 1B2 (generated using the N-terminal 57-71 epitope), as well as hybridoma clone 1 D9 (generated using the C-terminal 372-385 epitope) are able to detect, by Western blot, DICAM expressed by THP1 cells. FIGS. 16A and 16B show that anti-DICAM antibodies from clones 2C11, 2H12, 9E9 and 1B2 generated using the 57-71 epitope are able to detect, by flow cytometry, DICAM expressed at the surface of THP1 cells. FIGS. 17A to 17C show that anti-DICAM antibodies from clone 7F8, but not those from clones 1 D9 and 4B8, generated using the 372-385 epitope, permits to detect DICAM expressed at the surface of THP1 cells by flow cytometry. FIG. 18B shows the Western Blot analysis of the expression of DICAM by NIH3T3 cells transfected or not with a DICAM-encoding vector, using the supernatants of anti-DICAM hybridoma clones 1D4, 3C2 and 9E9. FIG. 18C shows that anti-DICAM hybridoma clones 1B2 and 9E9 detect cell surface expression of DICAM by NIH3T3 cells transfected with a DICAM-encoding vector. FIGS. 18D and 18E show the flow cytometric detection of DICAM at the surface of i) NS0 cells transfected with DICAM (FIG. 18D) and in vitro-generated $T_H17$ lymphocytes (FIG. 18E) using purified monoclonal antibody clone 9E9 conjugated to the fluorescent dye CF657.

EXAMPLE 8

Sequencing of Monoclonal Antibody (mAb) Clones 9E9 and 3C2

The sequences of the anti-DICAM antibodies expressed by hybridoma clones 9E9 and 3C2 was determined. The DNA sequences of eight each of clones 3C2 and 9E9 heavy chain, as well as eight each of clones 3C2 and CHUM 9E9 kappa chain variable regions, were obtained.

Of the 8 PCR positive 9E9 kappa chain clones sequenced, 7 of the resulting sequences had ORFs which came back as positive matches for a murine kappa chain in a BLAST search. Of these 7, 6 contained the exact same nucleotide sequence for the variable region, from the putative ATG start codon to the beginning of the consensus kappa chain constant region (underlined in FIG. 25A). For the last sequence, there were 8 nucleotide substitutions at the 5' of the variable region when compared to the other six sequences. Therefore, it was determined that the sequence given by the 6 identical sequences represents the consensus sequence. This consensus sequence (FIG. 25A) was translated into the amino acid sequence shown in FIG. 25B.

Of the 8 PCR positive 9E9 IgG1 heavy chain clones sequenced, 7 of the resulting sequences had open reading frames (ORFs) which came back as positive matches for mouse IgG1 chain in a BLAST search. Six of the seven sequences contained the exact same nucleotide sequence for the variable region, from the putative ATG start codon to the beginning of consensus IgG1 constant region (underlined in FIG. 25C). This consensus sequence (FIG. 25C) provided the longest ORF found in the total sequenced area, which was translated into the amino acid sequence shown in FIG. 25D. The last sequence was the same as the consensus sequence except for 1 nucleotide difference, which changed a "T" to a "C" (in bold and italics in FIG. 25C). This nucleotide change caused a change in the amino acid sequence from an "F" to an "L"

Of the 8 PCR positive 3C2 kappa (light) chain clones sent for sequencing, 6 of the resulting sequences had ORFs which came back as positive matches for a murine kappa chain in a BLAST search. Of these 6, two contained the exact same nucleotide sequence for the variable region except for one silent substitution (T to C, in bold and italics in FIG. 27A), from the putative ATG start codon to the beginning of the consensus kappa chain constant region (underlined in FIG. 27A). For the other four sequences, nucleotide substitutions 5' of the constant region produced a "TAA" stop codon, causing the translated sequence to be truncated. Therefore, it is determined that the sequence given by the two complete sequences is the consensus sequence. This consensus sequence (FIG. 27A) was translated into the amino acid sequence shown in FIG. 27B.

Of the 8 PCR positive 3C2 IgG2b heavy chain clones sequenced, 6 of the resulting sequences had open reading frames (ORFs) which came back as positive matches for mouse IgG2b chain in a BLAST search. Five of the six sequences contained the exact same nucleotide sequence for the variable region, from the putative ATG start codon to the beginning of consensus IgG2b constant region (underlined in FIG. 27C). This consensus sequence (FIG. 27C) provided the longest ORF found in the total sequenced area, which was translated into the amino acid sequence shown in FIG. 27D. One of the sequence was the same as the consensus sequence except for 1 nucleotide difference, which changed a "T" to a "C" (in bold and italics in FIG. 27C). This nucleotide change caused a change in the amino acid sequence from a "Y" to a "H" (in bold and italics in FIG. 27D).

EXAMPLE 9

Figure 19A:
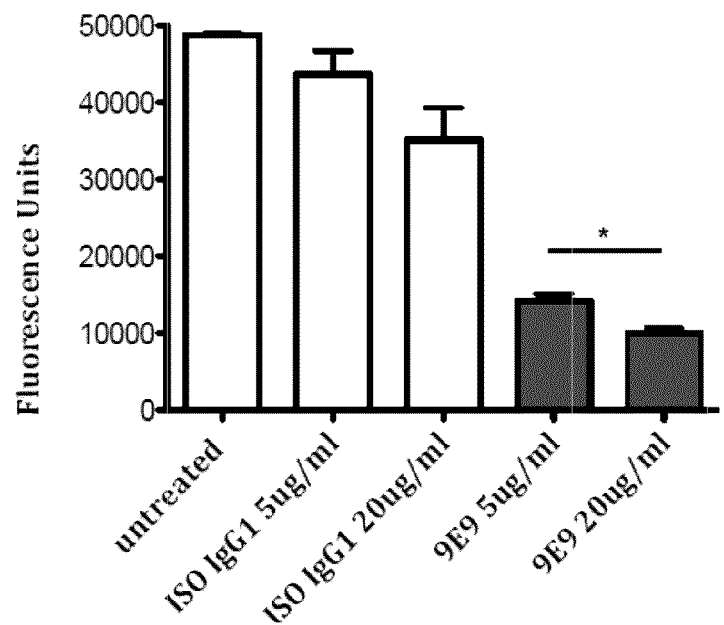
FIGS. 19A to 19C show that DICAM blockade using monoclonal antibody (mAb) clone 9E9, but not mAb clones 2C11, 1B2, or 2H12, restricts the adhesion of $T_H17$ lymphocytes to αVβ3 integrin in a cell-based ELISA. $T_H17$ lymphocytes were stained with Carboxyfluorescein succinimidyl ester (CFSE) and pre-treated with isotype control or anti-DICAM blocking Ab (each 5 µg/ml and 20 µg/ml). $T_H17$ lymphocytes stained with CFSE were allowed to bind to a plate coated with recombinant αVβ3 integrin (10 µg/ml) for 3 h at 37° C. After five washes, CFSE fluorescence was assessed and cells bound to the plate were manually counted.
Figure 19B:
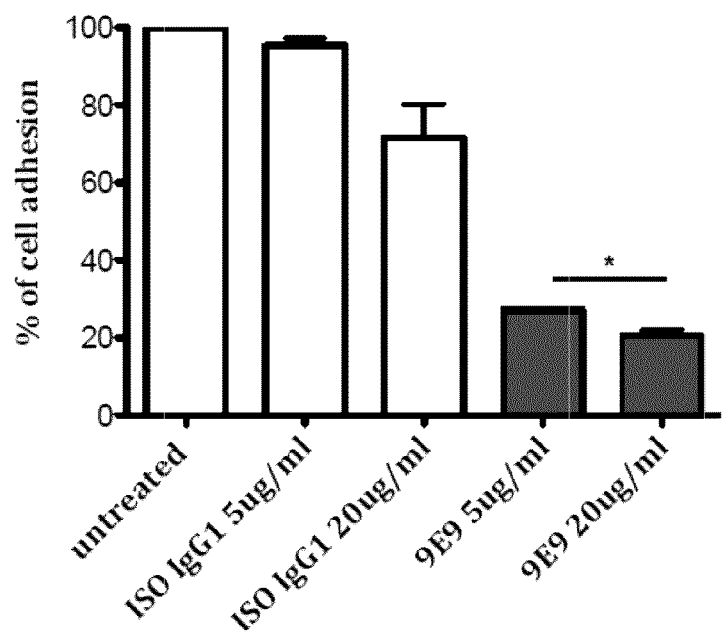
Figure 19C:
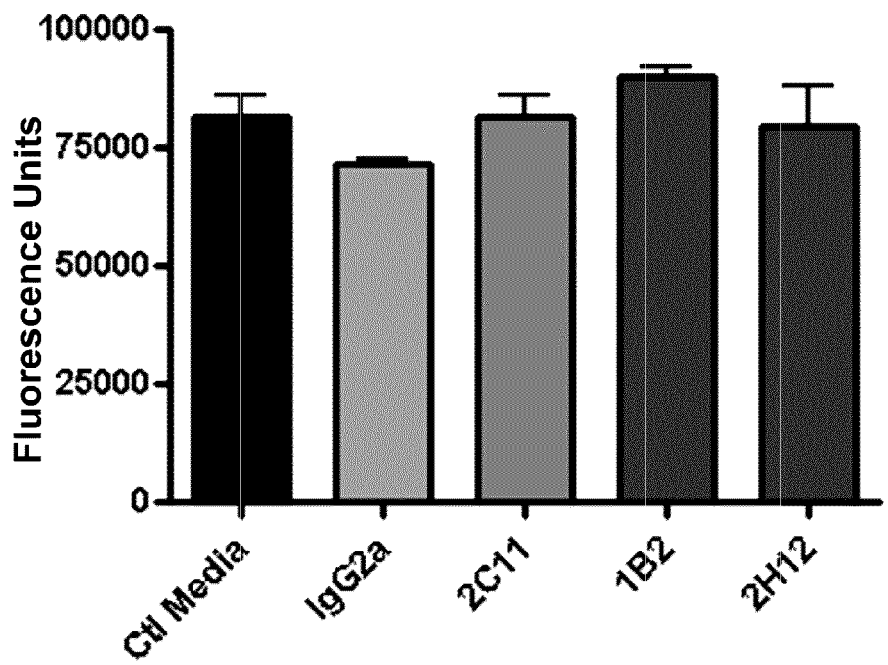

Effect of DICAM Blockade Using Monoclonal Antibody (mAb) Clone 9E9 on the Adhesion and Migration of $T_H17$ Lymphocytes FIGS. 19A and 19B show that DICAM blockade using monoclonal antibody (mAb) clone 9E9 restricts the adhesion of $T_H17$ lymphocytes to αVβ3 integrin in a cell-based ELISA. In contrast, mAb clones 1B2, 2C11 and 2H12 do not block the adhesion of $T_H17$ cells to αVβ3 integrin (FIG. 19C).

Figure 20A:
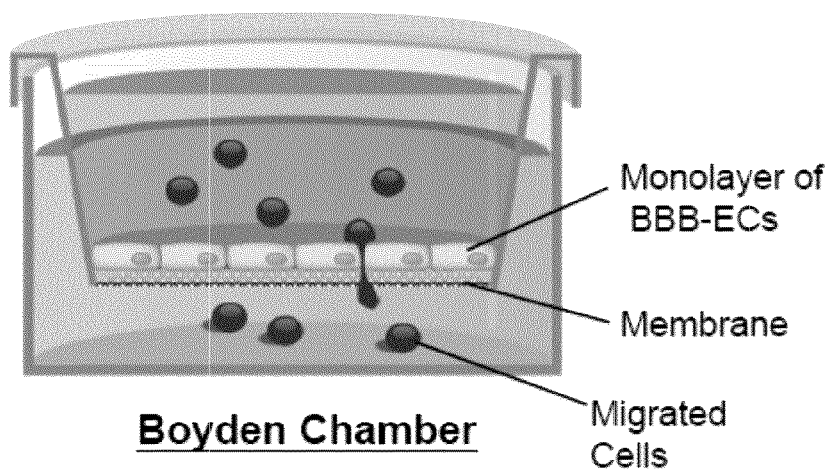
FIGS. 20A to 20E show that DICAM blockade using mAb clone 9E9 restricts the migration of $T_H17$ lymphocytes across the human blood-brain barrier (BBB).
Figure 20B:
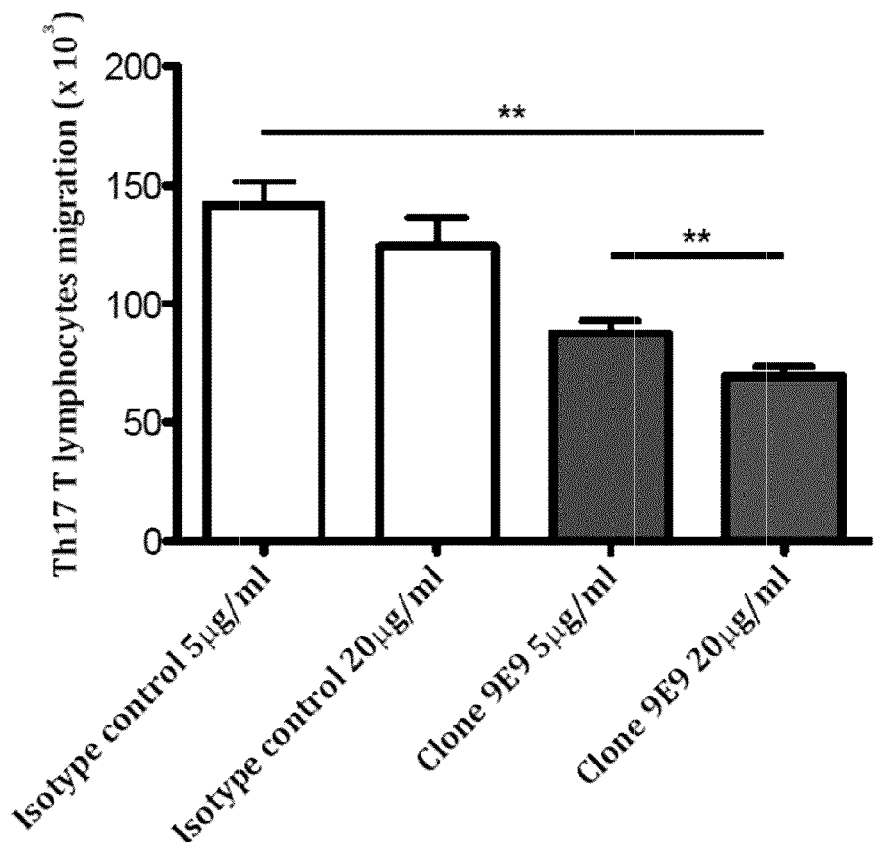
Figure 20C:
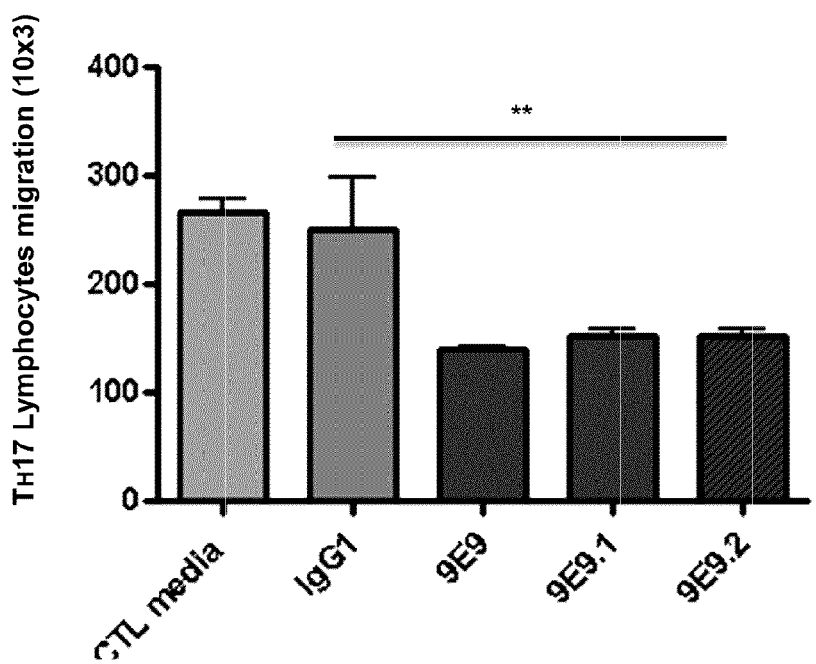
Figure 20D:
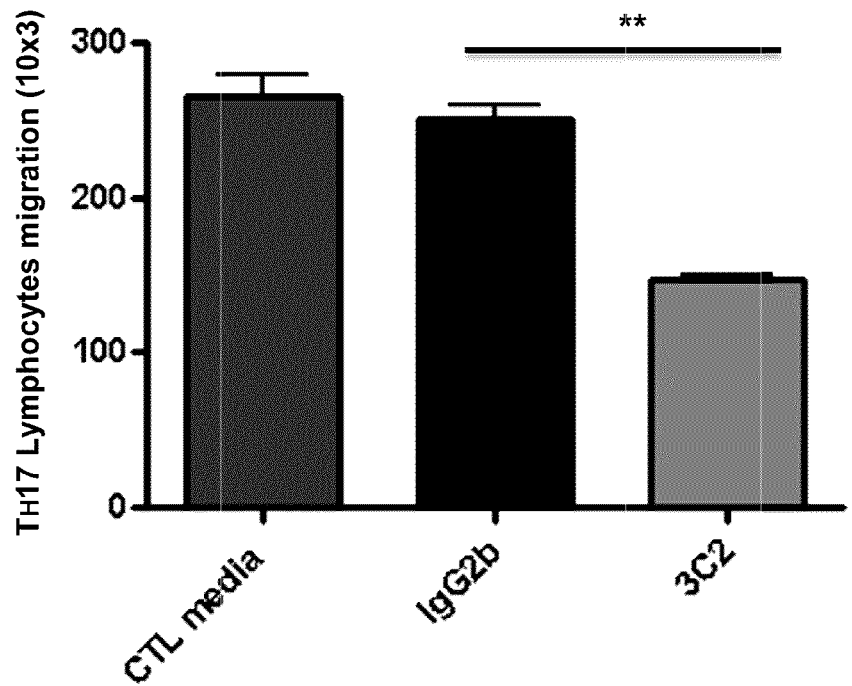
Figure 20E:
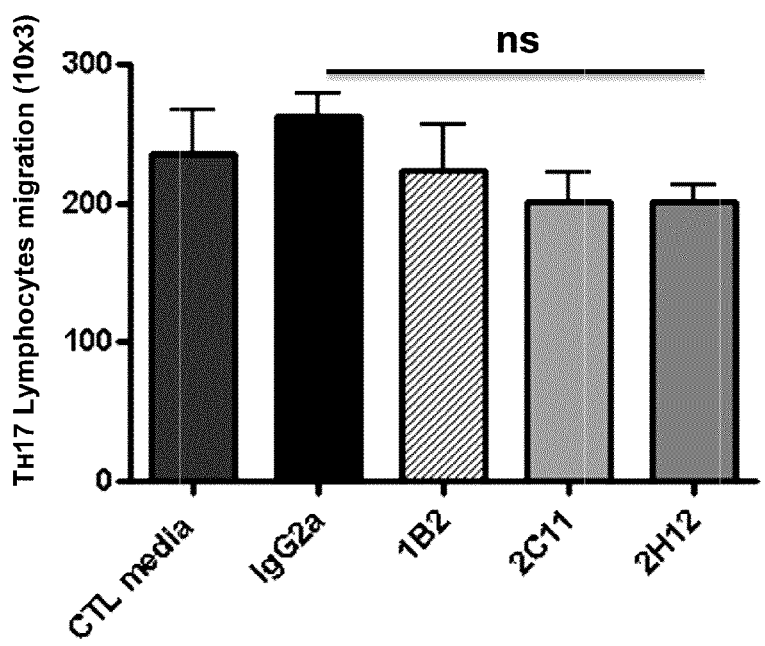

FIG. 20B shows that DICAM blockade using mAb clone 9E9 restricts the migration of $T_H17$ lymphocytes across the human BBB in the modified Boyden chamber assay shown in FIG. 20A. MAb subclones 9E9.1 and 9E9.2 (FIG. 20C) and clone 3C2 (FIG. 20D), but not mAb clones 1B2, 2C11 and 2H12, significantly restrict the migration of $T_H17$ lymphocytes across the human BBB. Thus, mAb clones 9E9 and 3C2, as well as subclones 9E9.1 and 9E9.2, neutralize DICAM-mediated migration of $T_H17$ lymphocytes across the human BBB.

Table III below summarizes the results obtained with the mAb clones described herein.

TABLE III

| Clone name | Epitope | Western blot | Flow cytometry | Migration | Adhesion |
|---|---|---|---|---|---|
| 7F8 | C-term | − | +++ | nt | nt |
| 1D9 | C-term | − | − | nt | nt |
| 4B8 | C-term | − | − | nt | nt |
| 1D4 | C-term | ++ | ++ | − | nt |
| 2H12 | N-term | +++ | ++ | − | − |
| 1B2 | N-term | +++ | ++ | − | − |
| 9E9 | N-term | ++ | +++ | +++ | +++ |
| 9E9.1 | N-term | nt | +++ | +++ | nt |
| 9E9.2 | N-term | nt | +++ | +++ | nt |
| 2C11 | N-term | +++ | +++ | − | − |
| 3C2 | N-term | − | − | +++ | − | nt = not tested

Figure 29A:
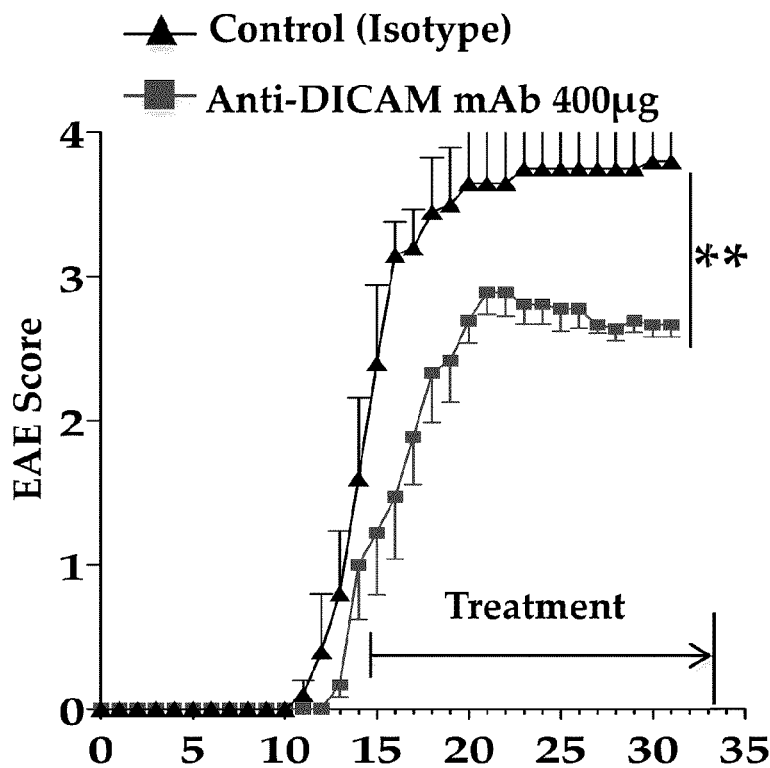
FIG. 29A shows the effect of anti-DICAM clone 9E9 on the clinical course of EAE mice. Female C57/BL6J mice were immunized subcutaneously with 200 μg of MOG$_{35-55}$ (MEVGWYRSPFSRVVHLYRNGK, SEQ ID NO: 33; Sheldon Biotechnology Centre) in a 100 μl emulsion of incomplete Freund's adjuvant supplemented with 4 mg/ml *Mycobacterium tuberculosis* (Fisher Scientific®), and injected intraperitoneally with *Pertussis* toxin (400 ng, Sigma-Aldrich®) on day 0 and 2 post-immunization (dpi). Monoclonal anti-DICAM antibody 9E9 (200 μg, squares) or control IgG1 mAb (triangles) were injected intraperitoneally at 14, 16, 18, 20, 22, 24, 26, 30, 32 and 34 dpi. n=14 animals per group. The EAE clinical grading was as follows: 0=normal; 1=paralyzed tail; 2=loss of coordinated movement and hindlimb paresis; 3=paralysis of one hindlimb (monoparalysis); 4=paralysis of both hindlimbs (paraparalysis); and 5=paralysis of hindlimbs and forelimbs (requires sacrifice).
Figure 29B:
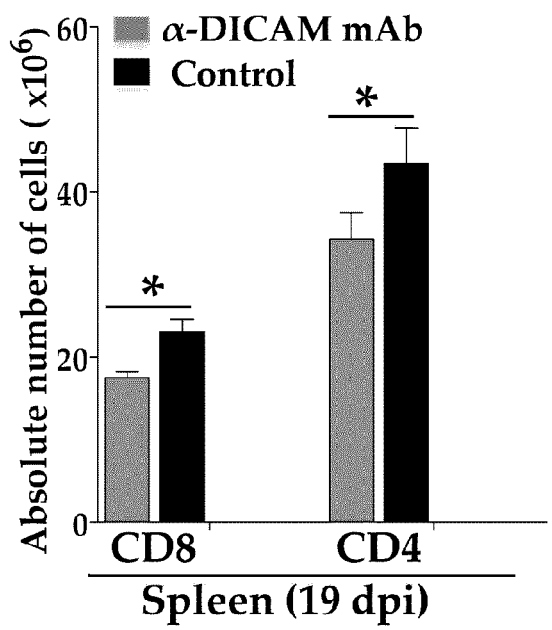
FIGS. 29B to 29D show the absolute numbers of CD4 and CD8 T lymphocytes in spleen, lymph nodes and CNS (spinal cord and brain), respectively, of EAE mice at 19 dpi as assessed by flow cytometry. n=2-4 animals/condition. ns=not significant, *$P<0.05$.
Figure 29C:
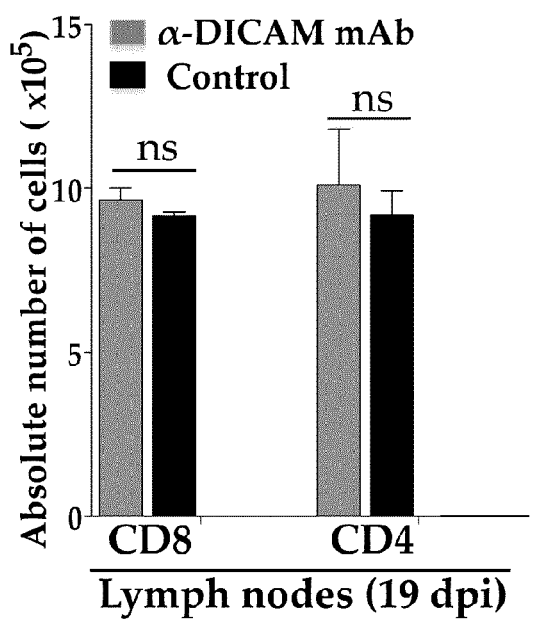
Figure 29D:
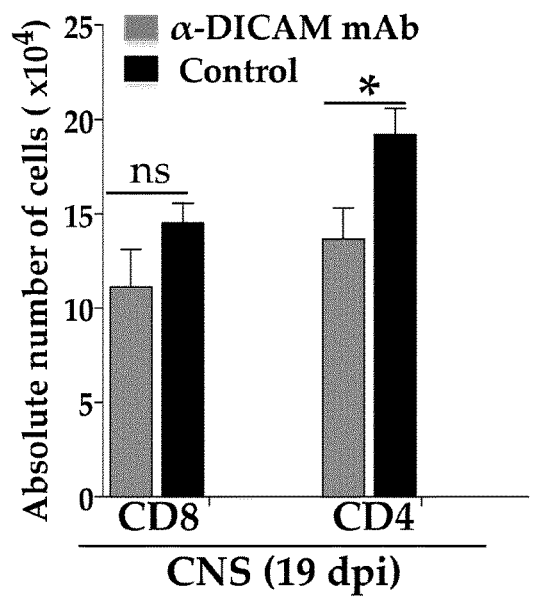
Figure 29E:
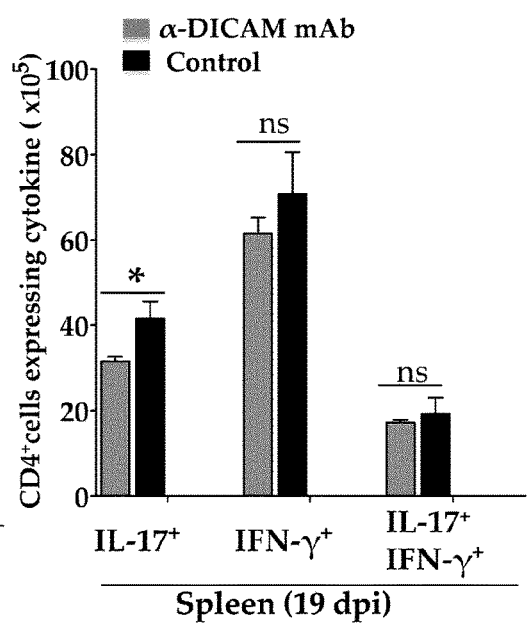
FIGS. 29E to 29G show the expression of IL-17 and IFNγ by CD4⁺ T lymphocytes from spleen, lymph nodes and CNS (spinal cord and brain), respectively, of EAE mice treated with mAb clone 9E9 or isotype control at 19 dpi, as assessed by flow cytometry. n=2-4 animals/condition. ns=not significant, *$P<0.05$.
Figure 29F:
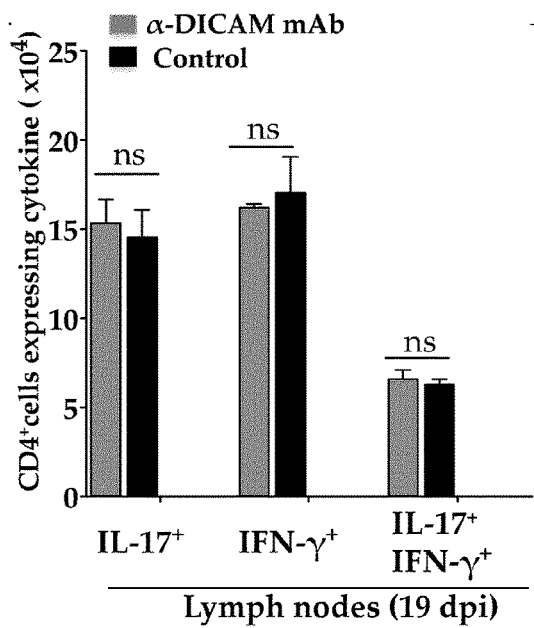
Figure 29G:
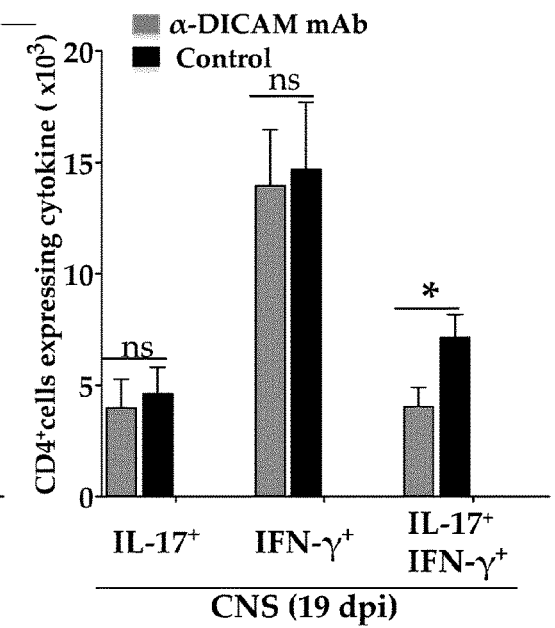

Effect of DICAM Blockade Using Monoclonal Antibody (mAb) Clone 9E9 on the Clinical Course of EAE Mice It was next assessed whether functional blockade of DICAM using mAb clone 9E9 could impact on autoimmune neuroinflammation in vivo. The results presented in FIG. 29A show that administration of mAb clone 9E9 after the onset of EAE (14 dpi) significantly reduces the clinical score of EAE mice, an animal model of a neuroinflammatory disease (multiple sclerosis), relative to administration of an isotype IgG1 control mAb. Treatment with mAb clone 9E9 also decreased the absolute number of CD4$^+$ T lymphocytes in the CNS of EAE mice sacrificed 19 dpi (FIG. 29D). Although T lymphocyte activation in the peripheral compartment was not impaired in 9E9-treated animals (FIGS. 29E and F), the absolute number of CD4$^+$ T lymphocytes expressing IL-17 and IFN-γ (pro-inflammatory CD4$^+$ T lymphocytes), as assessed by flow cytometry, was significantly lower in the CNS of EAE-affected animals treated, relative to isotype control-treated animals, 19 dpi (FIG. 29G). These results show that the anti-DICAM antibody blocked the migration/recruitment of inflammatory, IFN-γ-producing $T_H17$ lymphocytes into the CNS of EAE mice, and significantly improved the clinical course of the disease, thus providing evidence that antibody-mediated DICAM blockade may be useful for the treatment of inflammatory or autoimmune diseases.

Although the present invention has been described hereinabove by way of specific embodiments thereof, it can be modified, without departing from the spirit and nature of the subject invention as defined in the appended claims.

The invention claimed is:

1. An antibody or an antigen-binding fragment thereof that specifically binds to an epitope, located within a domain corresponding to residues 57- 71-of SEQ ID NO:18, wherein the antibody or antigen-binding fragment thereof comprises (a) the combination of light chain and heavy chain complementary determining regions (CDRs) set forth in Table 1:

TABLE I

| Region | Numbering Scheme | Sequence | SEQ ID NO: |
|---|---|---|---|
| CDR-L1 | Kabat | SASSSVSYMH-- | 1 |
|  | Chothia | SASSSVSYMH-- | 1 |
|  | AbM | SASSSVSYMH-- | 1 |
|  | Contact | ------SYMHWY | 2 |
| CDR-L2 | Kabat | ----STSNLAS | 3 |
|  | Chothia | ----STSNLAS | 3 |
|  | AbM | ----STSNLAS | 3 |
|  | Contact | LLIYSTSNLAS | 4 |
| CDR-L3 | Kabat | HQWSSYRT | 5 |
|  | Chothia | HQWSSYRT | 5 |
|  | AbM | HQWSSYRT | 5 |
|  | Contact | HQWSSYR- | 6 |
| CDR-H1 | Kabat | -----SYAMS | 7 |
|  | Chothia | GFTFISY--- | 8 |
|  | AbM | GFTFISYAMS | 9 |
|  | Contact | ----ISYAMS | 10 |
| CDR-H2 | Kabat | ---TISSGGSYTYYPHSVKG | 11 |
|  | Chothia | ------SSGGSY-------- | 12 |
|  | AbM | ---TISSGGSYTY------- | 13 |
|  | Contact | WVATISSGGSYTY------ | 14 |
| CDR-H3 | Kabat | --LDGPSYAMDY | 15 |
|  | Chothia | --LDGPSYAMDY | 15 |
|  | AbM | --LDGPSYAMDY | 15 |
|  | Contact | ARLDGPSYAMD- | 16; | or (b) the combination of light chain and heavy chain CDRs set o in Table II:

TABLE II

| Region | Numbering Scheme | Sequence | SEQ ID NO: |
|---|---|---|---|
| CDR-L1 | Kabat | RASKSVSTSGYSYIH-- | 36 |
|  | Chothia | RASKSVSTSGYSYIH-- | 36 |
|  | AbM | RASKSVSTSGYSYIH-- | 36 |
|  | Contact | ------STSGYSYIHWY | 37 |
| CDR-L2 | Kabat | ----LASNLES | 38 |
|  | Chothia | ----LASNLES | 38 |
|  | AbM | ----LASNLES | 38 |
|  | Contact | LLIYLASNLE- | 39 |
| CDR-L3 | Kabat | QHSRELPLT | 40 |
|  | Chothia | QHSRELPLT | 40 |
|  | AbM | QHSRELPLT | 40 |
|  | Contact | QHSRELPL- | 41 |
| CDR-H1 | Kabat | -----TFGVGVS | 42 |
|  | Chothia | GFSLSTFGV--- | 43 |
|  | AbM | GFSLSTFGVS | 44 |
|  | Contact | ----STFGVGVS | 45 |
| CDR-H2 | Kabat | ---HIFWDDDKHYNPSLKS | 46 |
|  | Chothia | ------FWDDD--------- | 47 |
|  | AbM | ---HIFWDDDKH------- | 48 |
|  | Contact | WLAHIFWDDDKH------ | 49 |
| CDR-H3 | Kabat | --GNYYASGYFFDY | 50 |
|  | Chothia | --GNYYASGYFFDY | 50 |
|  | AbM | --GNYYASGYFFDY | 50 |
|  | Contact | AQGNYYASGYFFDY | 51. |

2. The antibody or antigen-binding fragment thereof according to claim 1, wherein the antibody or antigen-binding fragment thereof blocks or inhibits the binding of DICAM to αVβ3 integrin.

3. The antibody or antigen-binding fragment thereof according to claim 1, wherein the antibody or antigen-binding fragment thereof blocks or inhibits the migration of $T_H 17$ lymphocytes across a vascular epithelium or endothelium.

4. The antibody or antigen-binding fragment thereof according to claim 3, wherein the vascular epithelium or endothelium is the blood-brain barrier.

5. The antibody or antigen-binding fragment thereof according to claim 1, wherein the antibody or antigen-binding fragment thereof comprises a light chain variable region comprising residues 23 to 129 of SEQ ID NO:26 and a heavy chain variable region comprising residues 20 to 137 of SEQ ID NO:28.

6. The antibody or antigen-binding fragment thereof according to claim 1, wherein the antibody or antigen-binding fragment thereof comprises a light chain variable region comprising residues 21 to 133 of SEQ NO:30 and a heavy chain variable region comprising residues 20 to 141 of SE NO:32.

7. The antibody or antigen-binding fragment thereof according to claim 1, which is a monoclonal antibody.

8. The antibody or antigen-binding fragment thereof according to claim 1, which is a recombinant antibody or antigen-binding fragment thereof.

9. The antibody or antigen-binding fragment thereof according to claim 1, wherein said antibody or antigen-binding fragment thereof comprises a detectable label attached thereto.

10. A composition comprising the antibody or antigen-binding fragment thereof according to claim 1, and an excipient.

11. The composition of claim 10, wherein said composition is a pharmaceutical composition, and said excipient is a pharmaceutically-acceptable excipient.

12. A method for treating multiple sclerosis in a subject in need thereof, said method comprising administering to said subject an effective amount of the antibody or antigen-binding fragment thereof according to claim 1.

13. The antibody or antigen-binding fragment thereof according to claim 1, wherein the antibody or antigen-binding fragment thereof comprises the CDR-L1, CDR-L2, CDR-L3, CDR-H1, CDR-H2 and CDR-H3 set forth in Table I.

14. The antibody or antigen-binding fragment thereof according to claim 13, Which is a humanized antibody or antigen-binding fragment thereof.

15. The antibody or antigen-binding fragment thereof according to claim 8, wherein the recombinant antibody is a humanized antibody.

16. A method for treating multiple sclerosis in a subject in need thereof, said method comprising administering to said subject an effective amount of the antibody or antigen-binding fragment thereof according to claim 13.

17. A method for treating multiple sclerosis in a subject in need thereof, said method comprising administering to said subject an effective amount of the antibody or antigen-binding fragment thereof according to claim 14.

* * * * *

SEQUENCE LISTING

```
<160> NUMBER OF SEQ ID NOS: 53

<210> SEQ ID NO 1
<211> LENGTH: 10
<212> TYPE: PRT
<213> ORGANISM: Mus musculus

<400> SEQUENCE: 1

Ser Ala Ser Ser Ser Val Ser Tyr Met His
1               5                   10

<210> SEQ ID NO 2
<211> LENGTH: 6
<212> TYPE: PRT
<213> ORGANISM: Mus musculus

<400> SEQUENCE: 2

Ser Tyr Met His Trp Tyr
1               5

<210> SEQ ID NO 3
<211> LENGTH: 7
<212> TYPE: PRT
<213> ORGANISM: Mus musculus

<400> SEQUENCE: 3

Ser Thr Ser Asn Leu Ala Ser
1               5

<210> SEQ ID NO 4
```

```
<211> LENGTH: 11
<212> TYPE: PRT
<213> ORGANISM: Mus musculus

<400> SEQUENCE: 4

Leu Leu Ile Tyr Ser Thr Ser Asn Leu Ala Ser
1               5                   10

<210> SEQ ID NO 5
<211> LENGTH: 8
<212> TYPE: PRT
<213> ORGANISM: Mus musculus

<400> SEQUENCE: 5

His Gln Trp Ser Ser Tyr Arg Thr
1               5

<210> SEQ ID NO 6
<211> LENGTH: 7
<212> TYPE: PRT
<213> ORGANISM: Mus musculus

<400> SEQUENCE: 6

His Gln Trp Ser Ser Tyr Arg
1               5

<210> SEQ ID NO 7
<211> LENGTH: 5
<212> TYPE: PRT
<213> ORGANISM: Mus musculus

<400> SEQUENCE: 7

Ser Tyr Ala Met Ser
1               5

<210> SEQ ID NO 8
<211> LENGTH: 7
<212> TYPE: PRT
<213> ORGANISM: Mus musculus

<400> SEQUENCE: 8

Gly Phe Thr Phe Ile Ser Tyr
1               5

<210> SEQ ID NO 9
<211> LENGTH: 10
<212> TYPE: PRT
<213> ORGANISM: Mus musculus

<400> SEQUENCE: 9

Gly Phe Thr Phe Ile Ser Tyr Ala Met Ser
1               5                   10

<210> SEQ ID NO 10
<211> LENGTH: 6
<212> TYPE: PRT
<213> ORGANISM: Mus musculus

<400> SEQUENCE: 10

Ile Ser Tyr Ala Met Ser
1               5

<210> SEQ ID NO 11
<211> LENGTH: 17
<212> TYPE: PRT
```

<213> ORGANISM: Mus musculus

<400> SEQUENCE: 11

Thr Ile Ser Ser Gly Gly Ser Tyr Thr Tyr Tyr Pro His Ser Val Lys
1               5                   10                  15
Gly

<210> SEQ ID NO 12
<211> LENGTH: 6
<212> TYPE: PRT
<213> ORGANISM: Mus musculus

<400> SEQUENCE: 12

Ser Ser Gly Gly Ser Tyr
1               5

<210> SEQ ID NO 13
<211> LENGTH: 10
<212> TYPE: PRT
<213> ORGANISM: Mus musculus

<400> SEQUENCE: 13

Thr Ile Ser Ser Gly Gly Ser Tyr Thr Tyr
1               5                   10

<210> SEQ ID NO 14
<211> LENGTH: 13
<212> TYPE: PRT
<213> ORGANISM: Mus musculus

<400> SEQUENCE: 14

Trp Val Ala Thr Ile Ser Ser Gly Gly Ser Tyr Thr Tyr
1               5                   10

<210> SEQ ID NO 15
<211> LENGTH: 10
<212> TYPE: PRT
<213> ORGANISM: Mus musculus

<400> SEQUENCE: 15

Leu Asp Gly Pro Ser Tyr Ala Met Asp Tyr
1               5                   10

<210> SEQ ID NO 16
<211> LENGTH: 11
<212> TYPE: PRT
<213> ORGANISM: Mus musculus

<400> SEQUENCE: 16

Ala Arg Leu Asp Gly Pro Ser Tyr Ala Met Asp
1               5                   10

<210> SEQ ID NO 17
<211> LENGTH: 2312
<212> TYPE: DNA
<213> ORGANISM: Homo sapiens

<400> SEQUENCE: 17
aatagcttga aactggaagg cagagactta gagccgagtg ggacaaagcc tggggctggg      60 cggggggccat ggcgctgcca tcccgaatcc tgctttggaa acttgtgctt ctgcagagct    120
ctgctgttct cctgcactca gggtcctcgg taccgccgc tgctggcagc tccgtggtgt     180
ccgagtccgc ggtgagctgg gaggcgggcg cccgggcggt gctgcgctgc cagagcccgc    240

```
gcatggtgtg gacccaggac cggctgcacg accgccagcg cgtgctccac tgggacctgc    300
gcggccccgg gggtggcccc gcgcggcgcc tgctggactt gtactcggcg ggcgagcagc    360
gcgtgtacga ggcgcgggac cgcggccgcc tggagctctc ggcctcggcc ttcgacgacg    420
gcaacttctc gctgctcatc cgcgcggtgg aggagacgga cgcggggctg tacacctgca    480
acctgcacca tcactactgc cacctctacg agagcctggc cgtccgcctg aggtcaccg     540 acggcccccc ggccacccccc gcctactggg acggcgagaa ggaggtgctg gcggtggcgc   600
gcggcgcacc cgcgcttctg acctgcgtga accgcgggca cgtgtggacc gaccggcacg    660
tggaggaggc tcaacaggtg gtgcactggg accggcagcc gcccggggtc ccgcacgacc    720
gcgcggaccg cctgctggac ctctacgcgt cgggcgagcg ccgcgcctac gggcccctt    780 ttctgcgcga ccgcgtggct gtgggcgcgg atgcctttga gcgcggtgac ttctcactgc    840
gtatcgagcc gctggaggtc gccgacgagg gcacctactc ctgccacctg caccaccatt    900
actgtggcct gcacgaacgc cgcgtcttcc acctgacggt cgccgaaccc cacgcggagc    960 cgccccccg ggctctccg gcaacggct ccagccacag cggcgcccca ggcccagacc      1020
ccacactggc gcgcggccac aacgtcatca atgtcatcgt ccccgagagc cgagcccact    1080
tcttccagca gctgggctac gtgctggcca cgctgctgct cttcatcctg ctactggtca    1140
ctgtcctcct ggccgccgc aggcgccgcg gaggctacga atactcggac cagaagtcgg     1200
gaaagtcaaa ggggaaggat gttaacttgg cggagttcgc tgtggctgca ggggaccaga    1260
tgctttacag gagtgaggac atccagctag attacaaaaa caacatcctg aaggagaggg    1320
cggagctggc ccacagcccc ctgcctgcca agtacatcga cctagacaaa gggttccgga    1380
aggagaactg caaatagga ggccctgggc tcctggctgg gccagcagct gcacctctcc     1440
tgtctgtgct cctcggggca tctcctgatg ctccggggct caccccctt ccagcggctg    1500 gtcccgcttt cctggaattt ggcctggcg tatgcagagg ccgcctccac acccctctcc    1560
caggggcttg gtggcagcat agcccccacc cctgcggcct ttgctcacgg gtggccctgc    1620 ccaccctgg cacaaccaaa atcccactga tgcccatcat gccctcagac ccttctgggc    1680
tctgcccgct gggggcctga agacattcct ggaggacact cccatcagaa cctggcagcc    1740
ccaaaactgg ggtcagcctc agggcaggag tcccactcct ccagggctct gctcgtccgg    1800
ggctgggaga tgttcctgga ggaggacact cccatcagaa cttggcagcc ttgaagttgg    1860
ggtcagcctc ggcaggagtc ccactcctcc tggggtgctg cctgccaccg agagctcccc    1920
cacctgtacc accatgtggg actccaggca ccatctgttc tccccaggga cctgctgact    1980
tgaatgccag cccttgctcc tctgtgttgc tttgggccac ctggggctgc acccctgcc     2040 cttctctgc cccatcccta ccctagcctt gctctcagcc accttgatag tcactgggct    2100
ccctgtgact tctgacccctg acaccctcc cttggactct gcctgggctg gagtctaggg    2160
ctggggctac atttggcttc tgtactggct gaggacaggg gagggagtga agttggtttg    2220
gggtggcctg tgttgccact ctcagcaccc cacatttgca tctgctggtg gacctgccac    2280
catcacaata aagtccccat ctgattttta ga                                  2312
```

<210> SEQ ID NO 18
<211> LENGTH: 442
<212> TYPE: PRT
<213> ORGANISM: Homo sapiens

<400> SEQUENCE: 18

-continued

```
Met Ala Leu Pro Ser Arg Ile Leu Leu Trp Lys Leu Val Leu Leu Gln
 1               5                  10                  15

Ser Ser Ala Val Leu Leu His Ser Gly Ser Ser Val Pro Ala Ala Ala
            20                  25                  30

Gly Ser Ser Val Val Ser Glu Ser Ala Val Ser Trp Glu Ala Gly Ala
            35                  40                  45

Arg Ala Val Leu Arg Cys Gln Ser Pro Arg Met Val Trp Thr Gln Asp
 50                  55                  60

Arg Leu His Asp Arg Gln Arg Val Leu His Trp Asp Leu Arg Gly Pro
 65                  70                  75                  80

Gly Gly Gly Pro Ala Arg Arg Leu Leu Asp Leu Tyr Ser Ala Gly Glu
                85                  90                  95

Gln Arg Val Tyr Glu Ala Arg Asp Arg Gly Arg Leu Glu Leu Ser Ala
            100                 105                 110

Ser Ala Phe Asp Asp Gly Asn Phe Ser Leu Leu Ile Arg Ala Val Glu
            115                 120                 125

Glu Thr Asp Ala Gly Leu Tyr Thr Cys Asn Leu His His Tyr Cys
            130                 135                 140

His Leu Tyr Glu Ser Leu Ala Val Arg Leu Glu Val Thr Asp Gly Pro
145                 150                 155                 160

Pro Ala Thr Pro Ala Tyr Trp Asp Gly Glu Lys Glu Val Leu Ala Val
                165                 170                 175

Ala Arg Gly Ala Pro Ala Leu Leu Thr Cys Val Asn Arg Gly His Val
                180                 185                 190

Trp Thr Asp Arg His Val Glu Glu Ala Gln Gln Val Val His Trp Asp
            195                 200                 205

Arg Gln Pro Pro Gly Val Pro His Asp Arg Ala Asp Arg Leu Leu Asp
            210                 215                 220

Leu Tyr Ala Ser Gly Glu Arg Arg Ala Tyr Gly Pro Leu Phe Leu Arg
225                 230                 235                 240

Asp Arg Val Ala Val Gly Ala Asp Ala Phe Glu Arg Gly Asp Phe Ser
                245                 250                 255

Leu Arg Ile Glu Pro Leu Glu Val Ala Asp Glu Gly Thr Tyr Ser Cys
            260                 265                 270

His Leu His His His Tyr Cys Gly Leu His Glu Arg Arg Val Phe His
            275                 280                 285

Leu Thr Val Ala Glu Pro His Ala Glu Pro Pro Arg Gly Ser Pro
290                 295                 300

Gly Asn Gly Ser Ser His Ser Gly Ala Pro Gly Pro Asp Pro Thr Leu
305                 310                 315                 320

Ala Arg Gly His Asn Val Ile Asn Val Ile Val Pro Glu Ser Arg Ala
                325                 330                 335

His Phe Phe Gln Gln Leu Gly Tyr Val Leu Ala Thr Leu Leu Leu Phe
            340                 345                 350

Ile Leu Leu Leu Val Thr Val Leu Leu Ala Ala Arg Arg Arg Gly
            355                 360                 365

Gly Tyr Glu Tyr Ser Asp Gln Lys Ser Gly Lys Ser Lys Gly Lys Asp
            370                 375                 380

Val Asn Leu Ala Glu Phe Ala Val Ala Ala Gly Asp Gln Met Leu Tyr
385                 390                 395                 400

Arg Ser Glu Asp Ile Gln Leu Asp Tyr Lys Asn Asn Ile Leu Lys Glu
                405                 410                 415

Arg Ala Glu Leu Ala His Ser Pro Leu Pro Ala Lys Tyr Ile Asp Leu
```

```
                420              425              430
Asp Lys Gly Phe Arg Lys Glu Asn Cys Lys
        435              440

<210> SEQ ID NO 19
<211> LENGTH: 2008
<212> TYPE: DNA
<213> ORGANISM: Homo sapiens

<400> SEQUENCE: 19
acttagagcc gagtgggaca aagcctgggg ctgggcgggg gccatggcgc tgccatcccg     60
aatcctgctt tggaaacttg tgcttctgca gagctctgct gttctcctgc actcagggtc    120
ctcggtaccc gccgctgctg gcagctccgt ggtgtccgag tccgcggtga gctgggaggc    180
gggcgcccgg gcggtgctgc gctgccagag cccgcgcatg gtgtggaccc aggaccggct    240
gcacgaccgc cagcgcgtgc tccactggga cctgcgcggc cccggggtg ccccgcgcg    300
gcgcctgctg gacttgtact cggcgggcga gcagcgcgtg tacgaggcgc gggaccgcgg    360
ccgcctggag ctctcggcct cggccttcga cgacggcaac ttctcgctgc tcatccgcgc    420
ggtggaggag acggacgcgg ggctgtacac ctgcaacctg caccatcact actgccacct    480
ctacgagagc ctggccgtcc gcctggaggt caccgacggc cccccggcca ccccgccta    540
ctgggacggc gagaaggagg tgctggcggt ggcgcgcggc gcacccgcgc ttctgacctg    600
cgtgaaccgc gggcacgtgt ggaccgaccg gcacgtggag gaggctcaac aggtggtgca    660
ctgggaccgg cagccgcccg ggtcccgca cgaccgcgcg accgcctgc tggacctcta    720
cgcgtcgggc gagcgccgcg cctacgggcc cttttctg cgcgaccgcg tggctgtggg    780
cgcggatgcc tttgagcgcg gtgacttctc actgcgtatc gagccgctgg aggtcgccga    840
cgagggcacc tactcctgcc acctgcacca ccattactgt ggcctgcacg aacgccgcgt    900
cttccacctg acggtcgccg aaccccacgc ggagccgccc ccgggggct ctccgggcaa    960
cggctccagc cacagcggcg ccccaggccc agaccccaca ctggcgcgcg ccacaacgt   1020
catcaatgtc atcgtccccg agagccgagc ccacttcttc cagcagctgg gctacgtgct   1080
ggccacgctg ctgctcttca tcctgctact ggtcactgtc ctcctggccg ccgcaggcg   1140
ccgcggaggc tacgaatact cggaccagaa gtcgggaaag tcaaagggga aggatgttaa   1200
cttggcggag ttcgctgtgg ctgcagggga ccagatgctt tacaggagtg aggacatcca   1260
gctagcctcc tctcctccca cagattacaa aacaacatc ctgaaggaga gggcggagct   1320
ggcccacagc cccctgcctg ccaagtacat cgacctagca aaagacccct ctgggctctg   1380
cccgctgggg gcctgaagac attcctggag gacactccca tcagaacctg cagccccaa    1440
aactggggtc agcctcaggg caggagtccc actcctccag ggctctgctc gtccgggct   1500
gggagatgtt cctggaggag gacactccca tcagaacttg cagccttga agttggggtc   1560
agcctcggca ggagtcccac tcctcctggg gtgctgcctg ccaccgagag ctcccccacc   1620
tgtaccacca tgtgggactc caggcaccat ctgttctccc cagggacctg ctgacttgaa   1680
tgccagccct tgctcctctg tgttgctttg ggccacctgg ggctgcaccc cctgcccttt   1740
ctctgcccca tccctaccct agccttgctc tcagccacct tgatagtcac tgggctcct   1800
gtgacttctg accctgacac ccctcccttg gactctgcct gggctggagt ctagggctgg   1860
ggctacattt ggcttctgta ctggctgagg acagggagg gagtgaagtt ggtttggggt   1920
ggcctgtgtt gccactctca gcaccccaca tttgcatctg ctggtggacc tgccaccatc   1980
```
acaataaagt ccccatctga tttttaga 2008

<210> SEQ ID NO 20
<211> LENGTH: 450
<212> TYPE: PRT
<213> ORGANISM: Homo sapiens

<400> SEQUENCE: 20

```
Met Ala Leu Pro Ser Arg Ile Leu Leu Trp Lys Leu Val Leu Leu Gln
1               5                   10                  15

Ser Ser Ala Val Leu Leu His Ser Gly Ser Ser Val Pro Ala Ala Ala
            20                  25                  30

Gly Ser Ser Val Val Ser Glu Ser Ala Val Ser Trp Glu Ala Gly Ala
        35                  40                  45

Arg Ala Val Leu Arg Cys Gln Ser Pro Arg Met Val Trp Thr Gln Asp
    50                  55                  60

Arg Leu His Asp Arg Gln Arg Val Leu His Trp Asp Leu Arg Gly Pro
65                  70                  75                  80

Gly Gly Gly Pro Ala Arg Arg Leu Leu Asp Leu Tyr Ser Ala Gly Glu
                85                  90                  95

Gln Arg Val Tyr Glu Ala Arg Asp Arg Gly Arg Leu Glu Leu Ser Ala
            100                 105                 110

Ser Ala Phe Asp Asp Gly Asn Phe Ser Leu Leu Ile Arg Ala Val Glu
        115                 120                 125

Glu Thr Asp Ala Gly Leu Tyr Thr Cys Asn Leu His His His Tyr Cys
    130                 135                 140

His Leu Tyr Glu Ser Leu Ala Val Arg Leu Glu Val Thr Asp Gly Pro
145                 150                 155                 160

Pro Ala Thr Pro Ala Tyr Trp Asp Gly Glu Lys Glu Val Leu Ala Val
                165                 170                 175

Ala Arg Gly Ala Pro Ala Leu Leu Thr Cys Val Asn Arg Gly His Val
            180                 185                 190

Trp Thr Asp Arg His Val Glu Glu Ala Gln Gln Val Val His Trp Asp
        195                 200                 205

Arg Gln Pro Pro Gly Val Pro His Asp Arg Ala Asp Arg Leu Leu Asp
    210                 215                 220

Leu Tyr Ala Ser Gly Glu Arg Arg Ala Tyr Gly Pro Leu Phe Leu Arg
225                 230                 235                 240

Asp Arg Val Ala Val Gly Ala Asp Ala Phe Glu Arg Gly Asp Phe Ser
                245                 250                 255

Leu Arg Ile Glu Pro Leu Glu Val Ala Asp Glu Gly Thr Tyr Ser Cys
            260                 265                 270

His Leu His His His Tyr Cys Gly Leu His Glu Arg Arg Val Phe His
        275                 280                 285

Leu Thr Val Ala Glu Pro His Ala Glu Pro Pro Arg Gly Ser Pro
    290                 295                 300

Gly Asn Gly Ser Ser His Ser Gly Ala Pro Gly Pro Asp Pro Thr Leu
305                 310                 315                 320

Ala Arg Gly His Asn Val Ile Asn Val Ile Val Pro Glu Ser Arg Ala
                325                 330                 335

His Phe Phe Gln Gln Leu Gly Tyr Val Leu Ala Thr Leu Leu Leu Phe
            340                 345                 350

Ile Leu Leu Leu Val Thr Val Leu Leu Ala Ala Arg Arg Arg Gly
        355                 360                 365
```

-continued

```
Gly Tyr Glu Tyr Ser Asp Gln Lys Ser Gly Lys Ser Lys Gly Lys Asp
    370             375                 380
Val Asn Leu Ala Glu Phe Ala Val Ala Ala Gly Asp Gln Met Leu Tyr
385             390                 395                 400
Arg Ser Glu Asp Ile Gln Leu Ala Ser Ser Pro Pro Thr Asp Tyr Lys
                405                 410                 415
Asn Asn Ile Leu Lys Glu Arg Ala Glu Leu Ala His Ser Pro Leu Pro
            420                 425                 430
Ala Lys Tyr Ile Asp Leu Asp Lys Asp Pro Ser Gly Leu Cys Pro Leu
        435                 440                 445
Gly Ala
    450

<210> SEQ ID NO 21
<211> LENGTH: 2731
<212> TYPE: DNA
<213> ORGANISM: Homo sapiens

<400> SEQUENCE: 21
aagaaggctg gcggtgtttc ctcttagagg ggagaaactc agcctgggta ggagacccag        60
ccccacgcag ggaaaactgt gctaacgctt ccgatgtgcg tggcaggtgc ggcggcggcg       120
aatacggttt gtcctcgagc ctaaccctgt ctgtgttggt gtcagcagtg ccccccctac       180
cacacacaca gggtccctgg cgtcccaaga ccactcctgg cagccccgcc actggctgcg       240
cctggaagcc gcgtcctcag gcctcgcctg gcatttgctg tcacagaggt tgcttccttg       300
ggtccgtccg tcctcgcccc tccagcctgg gcgcccccg accctgtct cattccctcc        360 accacatgca gcacagtcca ggaggctggg gtccaagagg ccatggctg caccccggct        420 tagtgctgag tccccagtgc ccagcaagcc tggcacccag gaggtggtca gcaaacgctt       480
ctgaacgaca ggaagtggga ctcttcagcc atcgatgatc cgctgtgcgg ccacaggctc       540
tgctgttctc ctgcactcag ggtcctcggt acccgccgct gctggcagct ccgtggtgtc       600
cgagtccgcg gtgagctggg aggcgggcgc ccgggcggtg ctgcgctgcc agagcccgcg       660
catggtgtgg acccaggacc ggctgcacga ccgccagcgc gtgctccact gggacctgcg       720
cggccccggg ggtggccccg cgcggcgcct gctggacttg tactcggcgg gcgagcagcg       780
cgtgtacgag gcgcgggacc gcggccgcct ggagctctcg gcctcggcct tcgacgacgg       840
caacttctcg ctgctcatcc gcgcggtgga ggagacggac gcggggctgt acacctgcaa       900
cctgcaccat cactactgcc acctctacga gagcctggcc gtccgcctgg aggtcaccga       960
cggccccccg gccaccccg cctactggga cggcgagaag gaggtgctgg cggtggcgcg      1020
cggcgcaccc gcgcttctga cctgcgtgaa ccgcgggcac gtgtggaccg accggcacgt      1080
ggaggaggct caacaggtgg tgcactggga ccggcagccg cccggggtcc cgcacgaccg      1140
cgcggaccgc ctgctggacc tctacgcgtc gggcgagcgc cgcgcctacg gccccttttt      1200
tctgcgcgac cgcgtggctg tgggcgcgga tgcctttgag cgcggtgact tctcactgcg      1260
tatcgagccg ctggaggtcg ccgacgaggg cacctactcc tgccacctgc accaccatta      1320
ctgtggcctg cacgaacgcc gcgtcttcca cctgacggtc gccgaacccc acgcggagcc      1380 gccccccgg ggctctccgg gcaacggctc cagccacagc ggcgccccag gcccagaccc       1440
cacactggcg cgcggccaca acgtcatcaa tgtcatcgtc cccgagagcc gagcccactt      1500
cttccagcag ctgggctacg tgctggccac gctgctgctc ttcatcctgc tactggtcac      1560
tgtcctcctg gccgcccgca ggcgccgcgg aggctacgaa tactcggacc agaagtcggg      1620
```

-continued

```
aaagtcaaag gggaaggatg ttaacttggc ggagttcgct gtggctgcag gggaccagat    1680
gctttacagg agtgaggaca tccagctaga ttacaaaaac aacatcctga aggagagggc    1740
ggagctggcc cacagccccc tgcctgccaa gtacatcgac ctagacaaag ggttccggaa    1800
ggagaactgc aaatagggag gccctgggct cctggctggg ccagcagctg cacctctcct    1860
gtctgtgctc ctcggggcat ctcctgatgc tccggggctc accccccttc agcggctgg    1920 tcccgctttc ctggaatttg gcctgggcgt atgcagaggc cgcctccaca cccctctccc    1980
aggggcttgg tggcagcata gcccccaccc ctgcggcctt tgctcacggg tggccctgcc    2040 caccccctggc acaaccaaaa tcccactgat gcccatcatg ccctcagacc cttctgggct    2100
ctgcccgctg ggggcctgaa gacattcctg gaggacactc ccatcagaac tggcagcccc    2160
caaaactggg gtcagcctca gggcaggagt cccactcctc cagggctctg tcgtccggg    2220 gctgggagat gttcctggag gaggacactc ccatcagaac ttggcagcct tgaagttggg    2280
gtcagcctcg gcaggagtcc cactcctcct ggggtgctgc ctgccaccga gagctccccc    2340
acctgtacca ccatgtggga ctccaggcac catctgttct ccccagggac ctgctgactt    2400
gaatgccagc ccttgctcct ctgtgttgct ttgggccacc tggggctgca ccccctgccc    2460
tttctctgcc ccatccctac cctagccttg ctctcagcca ccttgatagt cactgggctc    2520
cctgtgactt ctgaccctga caccccctccc ttggactctg cctgggctgg agtctagggc    2580
tggggctaca tttggcttct gtactggctg aggacagggg agggagtgaa gttggtttgg    2640
ggtggcctgt gttgccactc tcagcacccc acatttgcat ctgctggtgg acctgccacc    2700
atcacaataa agtccccatc tgatttttag a                                   2731
```

<210> SEQ ID NO 22
<211> LENGTH: 433
<212> TYPE: PRT
<213> ORGANISM: Homo sapiens

<400> SEQUENCE: 22

```
Met Ile Arg Cys Ala Ala Thr Gly Ser Ala Val Leu Leu His Ser Gly
1               5                   10                  15

Ser Ser Val Pro Ala Ala Ala Gly Ser Ser Val Ser Glu Ser Ala
                20                  25                  30

Val Ser Trp Glu Ala Gly Ala Arg Ala Leu Arg Cys Gln Ser Pro
            35                  40                  45

Arg Met Val Trp Thr Gln Asp Arg Leu His Asp Arg Gln Val Leu
        50                  55                  60

His Trp Asp Leu Arg Gly Pro Gly Gly Gly Pro Ala Arg Arg Leu Leu
65                  70                  75                  80

Asp Leu Tyr Ser Ala Gly Glu Gln Arg Val Tyr Glu Ala Arg Asp Arg
                85                  90                  95

Gly Arg Leu Glu Leu Ser Ala Ser Ala Phe Asp Asp Gly Asn Phe Ser
                100                 105                 110

Leu Leu Ile Arg Ala Val Glu Glu Thr Asp Ala Gly Leu Tyr Thr Cys
            115                 120                 125

Asn Leu His His Tyr Cys His Leu Tyr Glu Ser Leu Ala Val Arg
        130                 135                 140

Leu Glu Val Thr Asp Gly Pro Pro Ala Thr Pro Ala Tyr Trp Asp Gly
145                 150                 155                 160

Glu Lys Glu Val Leu Ala Val Ala Arg Gly Ala Pro Ala Leu Leu Thr
                165                 170                 175
```

```
Cys Val Asn Arg Gly His Val Trp Thr Asp Arg His Val Glu Glu Ala
            180                 185                 190
Gln Gln Val Val His Trp Asp Arg Gln Pro Pro Gly Val Pro His Asp
        195                 200                 205
Arg Ala Asp Arg Leu Leu Asp Leu Tyr Ala Ser Gly Glu Arg Arg Ala
    210                 215                 220
Tyr Gly Pro Leu Phe Leu Arg Asp Arg Val Ala Val Gly Ala Asp Ala
225                 230                 235                 240
Phe Glu Arg Gly Asp Phe Ser Leu Arg Ile Glu Pro Leu Glu Val Ala
                245                 250                 255
Asp Glu Gly Thr Tyr Ser Cys His Leu His His Tyr Cys Gly Leu
            260                 265                 270
His Glu Arg Arg Val Phe His Leu Thr Val Ala Glu Pro His Ala Glu
        275                 280                 285
Pro Pro Pro Arg Gly Ser Pro Gly Asn Gly Ser Ser His Ser Gly Ala
    290                 295                 300
Pro Gly Pro Asp Pro Thr Leu Ala Arg Gly His Asn Val Ile Asn Val
305                 310                 315                 320
Ile Val Pro Glu Ser Arg Ala His Phe Phe Gln Gln Leu Gly Tyr Val
                325                 330                 335
Leu Ala Thr Leu Leu Leu Phe Ile Leu Leu Leu Val Thr Val Leu Leu
            340                 345                 350
Ala Ala Arg Arg Arg Arg Gly Gly Tyr Glu Tyr Ser Asp Gln Lys Ser
        355                 360                 365
Gly Lys Ser Lys Gly Lys Asp Val Asn Leu Ala Glu Phe Ala Val Ala
    370                 375                 380
Ala Gly Asp Gln Met Leu Tyr Arg Ser Glu Asp Ile Gln Leu Asp Tyr
385                 390                 395                 400
Lys Asn Asn Ile Leu Lys Glu Arg Ala Glu Leu Ala His Ser Pro Leu
                405                 410                 415
Pro Ala Lys Tyr Ile Asp Leu Asp Lys Gly Phe Arg Lys Glu Asn Cys
            420                 425                 430
Lys

<210> SEQ ID NO 23
<211> LENGTH: 2231
<212> TYPE: DNA
<213> ORGANISM: Homo sapiens

<400> SEQUENCE: 23
atgtcctcgg accttcttgt ccctccaagg gtgcggtcac caccctccc caggcctgac      60
cggtgagggg ctgggcctct gctcccacac tgcccctccc cagcaggcca gcaacgatgg     120
gggaggccaa ggggcccggc aggagccaga ggggcggtc cccagaccgt agacaggccc     180
aggcctccgt gatgtcaccg cgggtgctaa ggagggggag ggggtagggc tgttttctg      240
gagagagact tagagccgag tgggacaaag cctggggctg gcgggggcc atggcgctgc     300
catcccgaat cctgctttgg aaacttgtgc ttctgcagag ctctgctgtt ctcctgcact    360
cagcggtgga ggagacggac gcggggctgt acacctgcaa cctgcaccat cactactgcc    420
acctctacga gagcctggcc gtccgcctgg aggtcaccga cggcccccg gccacccccg     480
cctactggga cggcgagaag gaggtgctgg cggtggcgcg cggcgcaccc gcgcttctga    540
cctgcgtgaa ccgcgggcac gtgtggaccg accggcacgt ggaggaggct caacaggtgg    600
```

```
tgcactggga ccggcagccg cccggggtcc cgcacgaccg cgcggaccgc ctgctggacc    660
tctacgcgtc gggcgagcgc cgcgcctacg ggccccttt  tctgcgcgac cgcgtggctg    720
tgggcgcgga tgcctttgag cgcggtgact tctcactgcg tatcgagccg ctggaggtcg    780
ccgacgaggg cacctactcc tgccacctgc accaccatta ctgtggcctg cacgaacgcc    840
gcgtcttcca cctgacggtc gccgaacccc acgcggagcc gccccccgg  ggctctccgg    900
gcaacggctc cagccacagc ggcgcccag  gcccagaccc cacactggcg cgcggccaca    960
acgtcatcaa tgtcatcgtc cccgagagcc gagcccactt cttccagcag ctgggctacg   1020
tgctggccac gctgctgctc ttcatcctgc tactggtcac tgtcctcctg gccgcccgca   1080
ggcgccgcgg aggctacgaa tactcggacc agaagtcggg aaagtcaaag gggaaggatg   1140
ttaacttggc ggagttcgct gtggctgcag ggaccagat  gctttacagg agtgaggaca   1200
tccagctaga ttacaaaaac aacatcctga aggagagggc ggagctggcc cacagccccc   1260
tgcctgccaa gtacatcgac ctagacaaag ggttccggaa ggagaactgc aaatagggag   1320
gccctgggct cctggctggg ccagcagctg cacctctcct gtctgtgctc ctcggggcat   1380
ctcctgatgc tccggggctc accccccttc agcggctgg  tcccgctttc ctggaatttg   1440
gcctgggcgt atgcagaggc cgcctccaca ccctctccc  aggggcttgg tggcagcata   1500
gcccccaccc ctgcggcctt tgctcacggg tggccctgcc caccctggc  acaaccaaaa   1560
tcccactgat gccatcatg  ccctcagacc cttctgggct ctgcccgctg ggggcctgaa   1620
gacattcctg gaggacactc ccatcagaac ctggcagccc caaaactggg gtcagcctca   1680
gggcaggagt cccactcctc cagggctctg ctcgtccggg gctgggagat gttcctggag   1740
gaggacactc ccatcagaac ttggcagcct tgaagttggg gtcagcctcg gcaggagtcc   1800
cactcctcct ggggtgctgc ctgccaccga gagctccccc acctgtacca ccatgtggga   1860
ctccaggcac catctgttct ccccagggac ctgctgactt gaatgccagc ccttgctcct   1920
ctgtgttgct ttgggccacc tggggctgca cccctgccc  tttctctgcc ccatccctac   1980
cctagccttg ctctcagcca ccttgatagt cactgggctc cctgtgactt ctgaccctga   2040
cacccctccc ttggactctg cctgggctgg agtctagggc tggggctaca tttggcttct   2100
gtactggctg aggacagggg agggagtgaa gttggtttgg ggtggcctgt gttgccactc   2160
tcagcacccc acatttgcat ctgctggtgg acctgccacc atcacaataa agtccccatc   2220
tgattttag  a                                                        2231
```

<210> SEQ ID NO 24
<211> LENGTH: 341
<212> TYPE: PRT
<213> ORGANISM: Homo sapiens

<400> SEQUENCE: 24

Met Ala Leu Pro Ser Arg Ile Leu Leu Trp Lys Leu Val Leu Leu Gln
1               5                   10                  15

Ser Ser Ala Val Leu Leu His Ser Ala Val Glu Glu Thr Asp Ala Gly
            20                  25                  30

Leu Tyr Thr Cys Asn Leu His His Tyr Cys His Leu Tyr Glu Ser
        35                  40                  45

Leu Ala Val Arg Leu Glu Val Thr Asp Gly Pro Pro Ala Thr Pro Ala
    50                  55                  60

Tyr Trp Asp Gly Glu Lys Glu Val Leu Ala Val Ala Arg Gly Ala Pro
65                  70                  75                  80

-continued

```
Ala Leu Leu Thr Cys Val Asn Arg Gly His Val Trp Thr Asp Arg His
                85                  90                  95

Val Glu Glu Ala Gln Gln Val Val His Trp Asp Arg Gln Pro Pro Gly
            100                 105                 110

Val Pro His Asp Arg Ala Asp Arg Leu Leu Asp Leu Tyr Ala Ser Gly
        115                 120                 125

Glu Arg Arg Ala Tyr Gly Pro Leu Phe Leu Arg Asp Arg Val Ala Val
    130                 135                 140

Gly Ala Asp Ala Phe Glu Arg Gly Asp Phe Ser Leu Arg Ile Glu Pro
145                 150                 155                 160

Leu Glu Val Ala Asp Glu Gly Thr Tyr Ser Cys His Leu His His His
                165                 170                 175

Tyr Cys Gly Leu His Glu Arg Arg Val Phe His Leu Thr Val Ala Glu
            180                 185                 190

Pro His Ala Glu Pro Pro Arg Gly Ser Pro Gly Asn Gly Ser Ser
        195                 200                 205

His Ser Gly Ala Pro Gly Pro Asp Pro Thr Leu Ala Arg Gly His Asn
    210                 215                 220

Val Ile Asn Val Ile Val Pro Glu Ser Arg Ala His Phe Phe Gln Gln
225                 230                 235                 240

Leu Gly Tyr Val Leu Ala Thr Leu Leu Leu Phe Ile Leu Leu Leu Val
                245                 250                 255

Thr Val Leu Leu Ala Ala Arg Arg Arg Arg Gly Gly Tyr Glu Tyr Ser
            260                 265                 270

Asp Gln Lys Ser Gly Lys Ser Lys Gly Lys Asp Val Asn Leu Ala Glu
        275                 280                 285

Phe Ala Val Ala Ala Gly Asp Gln Met Leu Tyr Arg Ser Glu Asp Ile
    290                 295                 300

Gln Leu Asp Tyr Lys Asn Asn Ile Leu Lys Glu Arg Ala Glu Leu Ala
305                 310                 315                 320

His Ser Pro Leu Pro Ala Lys Tyr Ile Asp Leu Asp Lys Gly Phe Arg
                325                 330                 335

Lys Glu Asn Cys Lys
            340

<210> SEQ ID NO 25
<211> LENGTH: 405
<212> TYPE: DNA
<213> ORGANISM: Mus musculus
<220> FEATURE:
<221> NAME/KEY: CDS
<222> LOCATION: (1)..(405)

<400> SEQUENCE: 25 atg gat ttt cag gtg cag att ttc agc ttc ctg cta atc agt gcc tca      48
Met Asp Phe Gln Val Gln Ile Phe Ser Phe Leu Leu Ile Ser Ala Ser
1               5                   10                  15 gtc ata atg tcc aga gga caa att gtt ctc acc cag tct cca gca atc      96
Val Ile Met Ser Arg Gly Gln Ile Val Leu Thr Gln Ser Pro Ala Ile
                20                  25                  30 atg tct gca ttt cta ggg gag gag atc acc cta acc tgc agt gcc agc     144
Met Ser Ala Phe Leu Gly Glu Glu Ile Thr Leu Thr Cys Ser Ala Ser
            35                  40                  45 tcg agt gta agt tac atg cac tgg tac cag cag aag tca ggc act tct     192
Ser Ser Val Ser Tyr Met His Trp Tyr Gln Gln Lys Ser Gly Thr Ser
    50                  55                  60 ccc aaa ctc ttg att tat agc aca tcc aac ctg gct tct gga gtc cct     240
```

```
Pro Lys Leu Leu Ile Tyr Ser Thr Ser Asn Leu Ala Ser Gly Val Pro
 65                  70                  75                  80 tct cgc ttc agt ggc agt ggg tct ggg acc ttt tat tct ctc aca atc       288
Ser Arg Phe Ser Gly Ser Gly Ser Gly Thr Phe Tyr Ser Leu Thr Ile
                     85                  90                  95 agc agt gtg gag gct gaa gat gct gcc gat tat tac tgc cat cag tgg       336
Ser Ser Val Glu Ala Glu Asp Ala Ala Asp Tyr Tyr Cys His Gln Trp
                100                 105                 110 agt agt tat cgg acg ttc ggt gga ggc acc aag ctg gaa atc aaa agg       384
Ser Ser Tyr Arg Thr Phe Gly Gly Gly Thr Lys Leu Glu Ile Lys Arg
            115                 120                 125 gct gat gct gca cca act gta                                           405
Ala Asp Ala Ala Pro Thr Val
            130                 135

<210> SEQ ID NO 26
<211> LENGTH: 135
<212> TYPE: PRT
<213> ORGANISM: Mus musculus

<400> SEQUENCE: 26

Met Asp Phe Gln Val Gln Ile Phe Ser Phe Leu Leu Ile Ser Ala Ser
  1               5                  10                  15

Val Ile Met Ser Arg Gly Gln Ile Val Leu Thr Gln Ser Pro Ala Ile
                 20                  25                  30

Met Ser Ala Phe Leu Gly Glu Glu Ile Thr Leu Thr Cys Ser Ala Ser
             35                  40                  45

Ser Ser Val Ser Tyr Met His Trp Tyr Gln Gln Lys Ser Gly Thr Ser
         50                  55                  60

Pro Lys Leu Leu Ile Tyr Ser Thr Ser Asn Leu Ala Ser Gly Val Pro
 65                  70                  75                  80

Ser Arg Phe Ser Gly Ser Gly Ser Gly Thr Phe Tyr Ser Leu Thr Ile
                 85                  90                  95

Ser Ser Val Glu Ala Glu Asp Ala Ala Asp Tyr Tyr Cys His Gln Trp
                100                 105                 110

Ser Ser Tyr Arg Thr Phe Gly Gly Gly Thr Lys Leu Glu Ile Lys Arg
            115                 120                 125

Ala Asp Ala Ala Pro Thr Val
            130                 135

<210> SEQ ID NO 27
<211> LENGTH: 453
<212> TYPE: DNA
<213> ORGANISM: Mus musculus
<220> FEATURE:
<221> NAME/KEY: CDS
<222> LOCATION: (1)..(453)

<400> SEQUENCE: 27 atg aac ttt gtg ctc agc ctg att ttc ctt gcc ctc att tta aaa ggt        48
Met Asn Phe Val Leu Ser Leu Ile Phe Leu Ala Leu Ile Leu Lys Gly
  1               5                  10                  15 gtc cag tgt gaa gtg cag ctg gtg gag tct ggg gga ggc tta gtg aag        96
Val Gln Cys Glu Val Gln Leu Val Glu Ser Gly Gly Gly Leu Val Lys
                 20                  25                  30 cct gga ggg tcc ctg aaa ctc tcc tgt gca gcc tct gga ttc act ttc       144
Pro Gly Gly Ser Leu Lys Leu Ser Cys Ala Ala Ser Gly Phe Thr Phe
             35                  40                  45 att agc tat gcc atg tct tgg gtt cgc cag act ccg gag aag agg ctg       192
Ile Ser Tyr Ala Met Ser Trp Val Arg Gln Thr Pro Glu Lys Arg Leu
```

```
gag tgg gtc gca acc att agt agt ggt ggt agt tac acc tac tat cca    240
Glu Trp Val Ala Thr Ile Ser Ser Gly Gly Ser Tyr Thr Tyr Tyr Pro
65                  70                  75                  80 cac agt gtg aag ggt cga ttc acc atc tcc aga gac aat gcc agg aac    288
His Ser Val Lys Gly Arg Phe Thr Ile Ser Arg Asp Asn Ala Arg Asn
                85                  90                  95 acc ctg tac ctg caa atg agc agt ctg agg tct gag gac acg gcc atg    336
Thr Leu Tyr Leu Gln Met Ser Ser Leu Arg Ser Glu Asp Thr Ala Met
            100                 105                 110 tat tac tgt gca aga ctg gat ggt ccc tca tat gct atg gac tac tgg    384
Tyr Tyr Cys Ala Arg Leu Asp Gly Pro Ser Tyr Ala Met Asp Tyr Trp
        115                 120                 125 ggt caa gga acc tca gtc acc gtc tcc tca gcc aaa acg aca ccc cca    432
Gly Gln Gly Thr Ser Val Thr Val Ser Ser Ala Lys Thr Thr Pro Pro
130                 135                 140 tct gtc tat cca ctg gcc cct                                        453
Ser Val Tyr Pro Leu Ala Pro
145                 150

<210> SEQ ID NO 28
<211> LENGTH: 151
<212> TYPE: PRT
<213> ORGANISM: Mus musculus

<400> SEQUENCE: 28

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ile Ser Tyr Ala Met Ser Trp Val Arg Gln Thr Pro Glu Lys Arg Leu
    50                  55                  60

Glu Trp Val Ala Thr Ile Ser Ser Gly Gly Ser Tyr Thr Tyr Tyr Pro
65                  70                  75                  80

His Ser Val Lys Gly Arg Phe Thr Ile Ser Arg Asp Asn Ala Arg Asn
                85                  90                  95

Thr Leu Tyr Leu Gln Met Ser Ser Leu Arg Ser Glu Asp Thr Ala Met
            100                 105                 110

Tyr Tyr Cys Ala Arg Leu Asp Gly Pro Ser Tyr Ala Met Asp Tyr Trp
        115                 120                 125

Gly Gln Gly Thr Ser Val Thr Val Ser Ser Ala Lys Thr Thr Pro Pro
130                 135                 140

Ser Val Tyr Pro Leu Ala Pro
145                 150

<210> SEQ ID NO 29
<211> LENGTH: 417
<212> TYPE: DNA
<213> ORGANISM: Mus musculus
<220> FEATURE:
<221> NAME/KEY: CDS
<222> LOCATION: (1)..(417)

<400> SEQUENCE: 29 atg gag aca gac aca ctc ctg tta tgg gta ctg ctg ctc tgg gtt cca    48
Met Glu Thr Asp Thr Leu Leu Leu Trp Val Leu Leu Leu Trp Val Pro
1               5                   10                  15
```

| | |
|---|---|
| ggt tcc act ggt gac att gtg ctg aca cag tct cct gct tcc tta act<br>Gly Ser Thr Gly Asp Ile Val Leu Thr Gln Ser Pro Ala Ser Leu Thr<br>            20                     25                     30 | 96 |
| gta tct ctg ggg cag agg gcc acc atc tca tgc agg gcc agc aaa agt<br>Val Ser Leu Gly Gln Arg Ala Thr Ile Ser Cys Arg Ala Ser Lys Ser<br>  35                         40                     45 | 144 |
| gtc agt aca tct ggc tat agt tat ata cac tgg tac caa cag aaa cca<br>Val Ser Thr Ser Gly Tyr Ser Tyr Ile His Trp Tyr Gln Gln Lys Pro<br>50                      55                     60 | 192 |
| gga cag cca ccc aaa ctc ctc atc tat ctt gca tcc aac cta gaa tct<br>Gly Gln Pro Pro Lys Leu Leu Ile Tyr Leu Ala Ser Asn Leu Glu Ser<br>65                     70                    75                   80 | 240 |
| ggg gtc cct gcc agg ttc agt ggc agt ggg tct ggg aca gac ttc acc<br>Gly Val Pro Ala Arg Phe Ser Gly Ser Gly Ser Gly Thr Asp Phe Thr<br>                  85                     90                     95 | 288 |
| ctc aac atc cat cct gtg gag gag gag gat gct gca acc tat tac tgt<br>Leu Asn Ile His Pro Val Glu Glu Glu Asp Ala Ala Thr Tyr Tyr Cys<br>                      100                  105                110 | 336 |
| cag cac agt agg gag ctt ccg ctc acg ttc ggt gct ggg acc aag ctg<br>Gln His Ser Arg Glu Leu Pro Leu Thr Phe Gly Ala Gly Thr Lys Leu<br>        115                      120                  125 | 384 |
| gag ctg aaa cgg gct gat gct gca cca act gta<br>Glu Leu Lys Arg Ala Asp Ala Ala Pro Thr Val<br>        130                      135 | 417 |

<210> SEQ ID NO 30
<211> LENGTH: 139
<212> TYPE: PRT
<213> ORGANISM: Mus musculus

<400> SEQUENCE: 30

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Ile His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Leu Pro Leu Thr Phe Gly Ala Gly Thr Lys Leu
        115                 120                 125

Glu Leu Lys Arg Ala Asp Ala Ala Pro Thr Val
    130                 135

<210> SEQ ID NO 31
<211> LENGTH: 462
<212> TYPE: DNA
<213> ORGANISM: Mus musculus
<220> FEATURE:
<221> NAME/KEY: CDS
<222> LOCATION: (1)..(462)

<400> SEQUENCE: 31

| | |
|---|---|
| atg gac agg ctt act tcc tca ttc cta ctc ctg att gtt cct gtc tat | 48 |

```
Met Asp Arg Leu Thr Ser Ser Phe Leu Leu Leu Ile Val Pro Val Tyr
1               5                   10                  15 gtc cta tcc cag gtt act ctg aaa gag tct ggc cct ggg ata ttg cag      96
Val Leu Ser Gln Val Thr Leu Lys Glu Ser Gly Pro Gly Ile Leu Gln
            20                  25                  30 ccc tcc cag acc ctc agt ctg act tgt tct ttc tct ggg ttt tca ctg     144
Pro Ser Gln Thr Leu Ser Leu Thr Cys Ser Phe Ser Gly Phe Ser Leu
        35                  40                  45 agc act ttt ggt gtg ggt gtg agc tgg att cgt cag cct tca ggg aat     192
Ser Thr Phe Gly Val Gly Val Ser Trp Ile Arg Gln Pro Ser Gly Asn
    50                  55                  60 ggt ctg gag tgg ctg gca cac att ttt tgg gat gat gac aag cac tat     240
Gly Leu Glu Trp Leu Ala His Ile Phe Trp Asp Asp Asp Lys His Tyr
65                  70                  75                  80 aac cca tcc ttg aag agc cgg ctc aca atc tcc aag gat acc tcc aac     288
Asn Pro Ser Leu Lys Ser Arg Leu Thr Ile Ser Lys Asp Thr Ser Asn
                85                  90                  95 aac cag gtt ttc ctc aag atc acg act gtg gac act gca gat act gcc     336
Asn Gln Val Phe Leu Lys Ile Thr Thr Val Asp Thr Ala Asp Thr Ala
            100                 105                 110 aca tac tac tgt gct caa ggg aat tac tac gct agt ggt tac ttc ttt     384
Thr Tyr Tyr Cys Ala Gln Gly Asn Tyr Tyr Ala Ser Gly Tyr Phe Phe
        115                 120                 125 gac tac tgg ggc caa ggc acc act ctc aca gtc tcc tca gcc aaa aca     432
Asp Tyr Trp Gly Gln Gly Thr Thr Leu Thr Val Ser Ser Ala Lys Thr
    130                 135                 140 aca ccc cca tca gtc tat cca ctg gcc cct                             462
Thr Pro Pro Ser Val Tyr Pro Leu Ala Pro
145                 150

<210> SEQ ID NO 32
<211> LENGTH: 154
<212> TYPE: PRT
<213> ORGANISM: Mus musculus

<400> SEQUENCE: 32

Met Asp Arg Leu Thr Ser Ser Phe Leu Leu Leu Ile Val Pro Val Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Phe Gly Val Gly Val Ser Trp Ile Arg Gln Pro Ser Gly Asn
    50                  55                  60

Gly Leu Glu Trp Leu Ala His Ile Phe Trp Asp Asp Asp Lys His Tyr
65                  70                  75                  80

Asn Pro Ser Leu Lys Ser Arg Leu Thr Ile Ser Lys Asp Thr Ser Asn
                85                  90                  95

Asn Gln Val Phe Leu Lys Ile Thr Thr Val Asp Thr Ala Asp Thr Ala
            100                 105                 110

Thr Tyr Tyr Cys Ala Gln Gly Asn Tyr Tyr Ala Ser Gly Tyr Phe Phe
        115                 120                 125

Asp Tyr Trp Gly Gln Gly Thr Thr Leu Thr Val Ser Ser Ala Lys Thr
    130                 135                 140

Thr Pro Pro Ser Val Tyr Pro Leu Ala Pro
145                 150

<210> SEQ ID NO 33
```

```
<211> LENGTH: 21
<212> TYPE: PRT
<213> ORGANISM: Mus musculus

<400> SEQUENCE: 33

Met Glu Val Gly Trp Tyr Arg Ser Pro Phe Ser Arg Val Val His Leu
1               5                   10                  15

Tyr Arg Asn Gly Lys
            20

<210> SEQ ID NO 34
<211> LENGTH: 15
<212> TYPE: PRT
<213> ORGANISM: Homo sapiens

<400> SEQUENCE: 34

Pro Arg Met Val Trp Thr Gln Asp Arg Leu His Asp Arg Gln Arg
1               5                   10                  15

<210> SEQ ID NO 35
<211> LENGTH: 14
<212> TYPE: PRT
<213> ORGANISM: Homo sapiens

<400> SEQUENCE: 35

Tyr Ser Asp Gln Lys Ser Gly Lys Ser Lys Gly Lys Asp Val
1               5                   10

<210> SEQ ID NO 36
<211> LENGTH: 15
<212> TYPE: PRT
<213> ORGANISM: Mus musculus

<400> SEQUENCE: 36

Arg Ala Ser Lys Ser Val Ser Thr Ser Gly Tyr Ser Tyr Ile His
1               5                   10                  15

<210> SEQ ID NO 37
<211> LENGTH: 11
<212> TYPE: PRT
<213> ORGANISM: Mus musculus

<400> SEQUENCE: 37

Ser Thr Ser Gly Tyr Ser Tyr Ile His Trp Tyr
1               5                   10

<210> SEQ ID NO 38
<211> LENGTH: 7
<212> TYPE: PRT
<213> ORGANISM: Mus musculus

<400> SEQUENCE: 38

Leu Ala Ser Asn Leu Glu Ser
1               5

<210> SEQ ID NO 39
<211> LENGTH: 10
<212> TYPE: PRT
<213> ORGANISM: Mus musculus

<400> SEQUENCE: 39

Leu Leu Ile Tyr Leu Ala Ser Asn Leu Glu
1               5                   10
```

```
<210> SEQ ID NO 40
<211> LENGTH: 9
<212> TYPE: PRT
<213> ORGANISM: Mus musculus

<400> SEQUENCE: 40

Gln His Ser Arg Glu Leu Pro Leu Thr
1               5

<210> SEQ ID NO 41
<211> LENGTH: 8
<212> TYPE: PRT
<213> ORGANISM: Mus musculus

<400> SEQUENCE: 41

Gln His Ser Arg Glu Leu Pro Leu
1               5

<210> SEQ ID NO 42
<211> LENGTH: 7
<212> TYPE: PRT
<213> ORGANISM: Mus musculus

<400> SEQUENCE: 42

Thr Phe Gly Val Gly Val Ser
1               5

<210> SEQ ID NO 43
<211> LENGTH: 9
<212> TYPE: PRT
<213> ORGANISM: Mus musculus

<400> SEQUENCE: 43

Gly Phe Ser Leu Ser Thr Phe Gly Val
1               5

<210> SEQ ID NO 44
<211> LENGTH: 10
<212> TYPE: PRT
<213> ORGANISM: Mus musculus

<400> SEQUENCE: 44

Gly Phe Ser Leu Ser Thr Phe Gly Val Ser
1               5                   10

<210> SEQ ID NO 45
<211> LENGTH: 8
<212> TYPE: PRT
<213> ORGANISM: Mus musculus

<400> SEQUENCE: 45

Ser Thr Phe Gly Val Gly Val Ser
1               5

<210> SEQ ID NO 46
<211> LENGTH: 16
<212> TYPE: PRT
<213> ORGANISM: Mus musculus

<400> SEQUENCE: 46

His Ile Phe Trp Asp Asp Asp Lys His Tyr Asn Pro Ser Leu Lys Ser
1               5                   10                  15

<210> SEQ ID NO 47
<211> LENGTH: 5
```

<212> TYPE: PRT
<213> ORGANISM: Mus musculus

<400> SEQUENCE: 47

Phe Trp Asp Asp Asp
1               5

<210> SEQ ID NO 48
<211> LENGTH: 9
<212> TYPE: PRT
<213> ORGANISM: Mus musculus

<400> SEQUENCE: 48

His Ile Phe Trp Asp Asp Asp Lys His
1               5

<210> SEQ ID NO 49
<211> LENGTH: 12
<212> TYPE: PRT
<213> ORGANISM: Mus musculus

<400> SEQUENCE: 49

Trp Leu Ala His Ile Phe Trp Asp Asp Asp Lys His
1               5                   10

<210> SEQ ID NO 50
<211> LENGTH: 12
<212> TYPE: PRT
<213> ORGANISM: Mus musculus

<400> SEQUENCE: 50

Gly Asn Tyr Tyr Ala Ser Gly Tyr Phe Phe Asp Tyr
1               5                   10

<210> SEQ ID NO 51
<211> LENGTH: 14
<212> TYPE: PRT
<213> ORGANISM: Mus musculus

<400> SEQUENCE: 51

Ala Gln Gly Asn Tyr Tyr Ala Ser Gly Tyr Phe Phe Asp Tyr
1               5                   10

<210> SEQ ID NO 52
<211> LENGTH: 16
<212> TYPE: PRT
<213> ORGANISM: Artificial
<220> FEATURE:
<223> OTHER INFORMATION: antigen peptides

<400> SEQUENCE: 52

Pro Arg Met Val Trp Thr Gln Asp Arg Leu His Asp Arg Gln Arg Cys
1               5                   10                  15

<210> SEQ ID NO 53
<211> LENGTH: 15
<212> TYPE: PRT
<213> ORGANISM: Artificial
<220> FEATURE:
<223> OTHER INFORMATION: antigen peptides

<400> SEQUENCE: 53

Cys Tyr Ser Asp Gln Lys Ser Gly Lys Ser Lys Gly Lys Asp Val
1               5                   10                  15

UNITED STATES PATENT AND TRADEMARK OFFICE
CERTIFICATE OF CORRECTION

PATENT NO. : 10,428,144 B2
APPLICATION NO. : 15/537768
DATED : October 1, 2019
INVENTOR(S) : Prat et al.

It is certified that error appears in the above-identified patent and that said Letters Patent is hereby corrected as shown below:

In the Specification

Column 1, Line 65: Please correct "IFNβ-1b" to read -- IFNβ-Ib --

Column 6, Line 4: Please insert a paragraph break in between "thereof." and "44."

Column 7, Line 24: Please correct "CD8$^{30}$" to read -- CD8$^+$ --

Column 14, Line 40: Please correct "I33" to read -- β3 --

Column 17, Line 64: Please correct "AZAPII" to read -- λZAPII --

Column 21, Line 49: Please correct "K and A" to read -- κ and λ --

Column 21, Line 55: Please correct "IgGI" to read -- IgG1 --

Column 27, Line 43: Please correct "IFN-y-secreting" to read -- IFNγ-secreting --

Column 27, Line 50: Please correct "IFN-γ" to read -- IFNγ --

Column 28, Line 5: Please correct "IFN-γ-secreting" to read -- IFNγ-secreting --

Column 32, Line 11: Please correct "pg of myelin" to read -- µg of myelin --

Column 32, Line 44: Please correct "I-glutamine" to read -- l-glutamine --

Column 32, Line 62: Please correct "IFN-γ" to read -- IFNγ --

Column 34, Line 57: Please correct "(30 pg)" to read -- (30 µg) --

Signed and Sealed this
Thirty-first Day of March, 2020

Andrei Iancu
*Director of the United States Patent and Trademark Office*

CERTIFICATE OF CORRECTION (continued)
U.S. Pat. No. 10,428,144 B2

Column 35, Line 12: Please correct "1 D4" to read -- 1D4 --

Column 35, Line 12: Please correct "1 D9" to read -- 1D9 --

Column 35, Line 64: Please correct "4 h30" to read -- 4h30 --

Column 36, Lines 17-18: Please connect the paragraph between "followed by" and "Bonferroni"

Column 37, Line 42: Please correct "1 D9" to read -- 1D9 --

Column 40, Line 19: Please correct "IFN-γ" to read -- IFNγ --

In the Claims

Column 78, Line 49, Claim 14: Please correct "Which" to read -- which --